US007256028B2

(12) United States Patent
Winther et al.

(10) Patent No.: US 7,256,028 B2
(45) Date of Patent: Aug. 14, 2007

(54) METHODS FOR SCREENING COMPOUNDS THAT MODULATE LIPID METABOLISM

(75) Inventors: Michael David Winther, Vancouver (CA); Leah Christine Knickle, Kentville (CA); Martin Haardt, Coldbrook (CA); Stephen John Allen, New Minas (CA); Andre Ponton, St. Hubert (CA); Roberto Justo De Antueno, Coldbrook (CA); D. Kenneth Jenkins, Coldbrook (CA); Solomon O. Nwaka, Coldbrook (CA)

(73) Assignee: Xenon Genetics Inc., Vancouver, British Colombia (CA)

( * ) Notice: Subject to any disclaimer, the term of this patent is extended or adjusted under 35 U.S.C. 154(b) by 337 days.

(21) Appl. No.: 10/415,232

(22) PCT Filed: Oct. 26, 2001

(86) PCT No.: PCT/CA01/01520

§ 371 (c)(1),
(2), (4) Date: Nov. 24, 2003

(87) PCT Pub. No.: WO02/34940

PCT Pub. Date: May 2, 2002

(65) Prior Publication Data

US 2004/0096435 A1    May 20, 2004

Related U.S. Application Data

(60) Provisional application No. 60/243,009, filed on Oct. 26, 2000.

(51) Int. Cl.
*C12N 9/02* (2006.01)
*C12N 15/09* (2006.01)
(52) U.S. Cl. ................ 435/189; 435/252.3; 435/320.1; 435/136; 435/69.2; 536/23.2
(58) Field of Classification Search ................ 435/189, 435/252.3, 320.1, 136, 69.2; 536/23.2
See application file for complete search history.

(56) References Cited

U.S. PATENT DOCUMENTS 6,432,684 B1 * 8/2002 Mukerji et al. ............. 435/136

FOREIGN PATENT DOCUMENTS

| WO | WO93/05182 | 3/1993 |
|----|------------|--------|
| WO | WO 00/20603 | 4/2000 |
| WO | WO 00/40705 | 7/2000 |
| WO | WO 00/53770 | 9/2000 |
| WO | WO 01/70993 | 9/2001 |

OTHER PUBLICATIONS

Sequence search alignment between USP 6,432,684—Accession No. ABS71838 and Applicants' SEQ ID No. 1.*
Sequence search alignment between US Patent 6,432,684—SEQ ID No. 12 and Applicants' SEQ ID No. 3].*
T. Aki, et al., "Molecular Cloning and Functional Characterization of Rat Δ-6 Fatty Acid Desaturase," Biochemical and Biophysical Research Communications, vol. 255, pp. 575-579 (1999).
K. Anderson, et al., "Five-Lipoxygenase Inhibitors Reduce PANC-1 Survival: The Mode of Cell Death and Synergism of MK886 with Gamma Linolenic Acid," Anticancer Research 18:791-800 (1998).
M. Arisaka, et al., "Prostaglandin Metabolism in Children With Diabetes Mellitus. I. Plasma Prostaglandin $E_2$, $F_{2\alpha}$, $TXB_2$, and Serum Fatty Acid Levels," Journal of Pediatric Gastroenterology and Nutrition, vol. 5:878-882 (1986).
J. Booyens, et al., "Chronic Arachidonic Acid Eicosanoid Imbalance: A Common Feature in Coronary Artery Disease, Hypercholesterolemia, Cancer and Other Important Diseases," Medical Hypotheses 18:53-60 (1985).
R. Brenner, et al., "Effect of Arachidonic Acid in the Alloxan-Diabetic Rat," American Journal of Physiology vol. 215, No. 1, pp. 63-70 (Jul. 1968).
P. Calder, "Immunoregulatory and Anti-inflammatory Effects of n-3 Polyunsaturated Fatty Acids," Brazilian Journal of Medical and Biological Research 31:467-490 (1998).
G. Calviello, et al., "Dietary Supplementation with Eicosapentaenoic and Docosahexaenoic Acid Inhibits Growth of Morris Hepatocarcinoma 3924A in Rats: Effects on Proliferation and Apoptosis," Int. J. Cancer, vol. 75, pp. 699-705 (1998).
S. Chavali, et al., "Decreased Production of Interleukin-6 and Prostaglandin $E_2$ Associated with Inhibition of Δ-5 Desaturation of ω6 Fatty Acids in Mice Fed Safflower Oil Diets Supplemented with Sesamol," Prostaglandins, Leukotrienes and Essential Fatty Acids, vol. 61, No. 6, pp. 347-352 (1999).
H. Cho, et al., "Cloning, Expression, and Nutritional Regulation of the Mammalian Δ-6 Desaturase," The Journal of Biological Chemistry, vol. 274, No. 1, pp. 471-477 (1999).

(Continued)

*Primary Examiner*—Tekchand Saidha
(74) *Attorney, Agent, or Firm*—Howrey LLP

(57) ABSTRACT

Drug screening assays useful in the discovery of pharmaceutically active compounds for use in the treatment of diseases involving abnormal lipid metabolism including diabetic neuropathy are taught. In particular, the control region of delta-5-desaturase gene is taught as a target for the drug screening methods, which serve to identify nucleotides, proteins, compounds and/or other pharmacological agents, which modulate the activity of desaturase enzymes or regulate the level of expression of the desaturase genes. Cell-based and cell lysate assays are taught for detecting components that interact with the desaturase enzymes and modify fatty acid profiles. In addition, cell-based and cell lysate assays are used to identify functional and regulatory elements controlling expression of the desaturase genes as well as to screen for components that modulate the transcriptional activity of the desaturase genes. Also taught is the gene for rat delta-5-desaturase.

6 Claims, 15 Drawing Sheets

OTHER PUBLICATIONS

H. Cho, et al., "Cloning, Expression, and Fatty Acid Regulation of the Human Δ-5 Desaturase," The Journal of Biological Chemistry, vol. 274, No. 52, pp. 37335-37339 (1999).

T. Coste, et al., "Beneficial Effects of Gamma Linolenic Acid Supplementation on Nerve Conduction Velocity, Na+, K+ ATPase Activity, and Membrane Fatty Acid Composition in Sciatic Nerve of Diabetic Rats," J. Nutr. Biochem, 10:411-420 (1999).

C. Curtis, et al., "n-3 Fatty Acids Specifically Modulate Catabolic Factors Involved in Articular Cartilage Degradation," The Journal of Biological Chemistry, vol. 275, No. 2, pp. 721-724 (2000).

A. Dang, et al., "Effect of Dietary Fats on Fatty Acid Composition and Δ5 Desaturase in Normal and Diabetic Rats," Lipids, vol. 24, No. 10, pp. 882-889 (1989).

U. Das, "Essential Fatty Acid Metabolism in Patients With Essential Hypertension Diabetes Mellitus and Coronary Heart Disease," Prostaglandins Leukotrienes and Essential Fatty Acids, vol. 52, pp. 387-391 (1995).

P. Dobner, et al., "Low-density Lipoproteins Supply Phospholipid-Bound Arachidonic Acid for Platelet Eicosanoid Production," American Physiological Society, vol. 275, pp. E777-E784 (1998).

P. du Toit, et al., "The Effect of Gamma-Linolenic Acid and Eicosapentaenoic Acid on Urokinase Activity," Prostaglandins Leukotrienes and Essential Fatty Acids, vol. 51, pp. 121-124 (1994).

F. Faas, et al., "Altered Fatty Acid Desaturation and Microsomal Fatty Acid Composition in the Streptozotocin Diabetic Rat," Lipids, 15:953-961 (1980).

J. Falconer, et al., "Effect of Eicosapentaenoic Acid and Other Fatty Acids on the Growth in Vitro of Human Pancreatic Cancer Cell Lines," J. Cancer, 69:826-832 (1994).

Y. Fujiwara, et al., "Immunochemical Evidence for the Enzymatic Difference of $\Delta^6$-Desaturase from $\Delta^9$- and $\Delta^5$-Desaturase in Rat Liver Microsomes," Biochemical and Biophysical Research Communications, vol. 110, No. 1, pp. 36-41 (1983).

J. Gadek, et al., "Effect of Enteral Feeding with Eicosapentaenoic Acid, Gamma-linolenic Acid, and Antioxidants in Patients with Acute Respiratory Distress Syndrome," Critical Care Medicine, vol. 27, No. 8, pp. 1409-1420 (1999).

A. Hansen, "Serum Lipid Changes and Therapeutic Effects of Various Oil in Infantile Eczema" Proc. Soc. Exp. Biol. Med., vol. 31, pp. 1160-1161 (1933).

L. Harbige, "Dietary n-6 and n-3 Fatty Acids in Immunity and Autoimmune Disease," Proceedings of the Nutrition Society, vol. 57, pp. 555-562 (1998).

M. James,et al., "Dietary Polyunsaturated Fatty Acids and Inflammatory Mediator Production," American Journal Clin., vol. 71 (supple):343S-348S (2000).

W. Jiang, et al., "Regulation of the Expressing of E-Caherin on Human Cancer Cells by γ-Lionolenic Acid (GLA)," Cancer Research, vol. 55, pp. 5043-5048 (1995).

W. Jiang, et al., "Inhibition of Hepatocyte Growth Factor-Induced Motility and In Vitro Invasion of Human Colon Cancer Cells by Gamma-Linolenic Acid," British Journal of Cancer, vol. 71, pp. 744-752 (1995).

W. Jiang, et al., "Gamma Linolenic Acid Regulates Gap Junction Communication In Endothelial Cells and Their Interaction With Tumor Cells," Prostaglandins, Leukotorienes and Essential Fatty Acids, vol. 56, No. 4, pp. 307-316 (1997).

W. Jiang, et al., "The effect of n-6 Polyunsaturated Fatty Acids on the Expression of nm-23 in Human Cancel Cells," British Journal of Cancer, vol. 77, No. 5, pp. 731-738 (1998).

W. Jiang, et al., "Peroxisome Proliferator Activated Receptor-γ(PRAR-γ) Mediates the Action of Gamma Linolenic Acid in Breast Cancer Cells," Prostaglandins, Leukotrienes and Essential Fatty Acids, vol. 62, No. 2, pp. 119-127 (2000).

P. Julu, "Influences of Evening Primrose Oil on Lipid Metabolism and Functions of Sensory Nerves in Diabetic Rats: Role of the Metabolic Pool of Essential Fatty Acids," AOCS Press, III., U.S.A., pp. 168-175 (1998).

H. Kawashima, et al., "Nicardipine and Nifedipine Inhibit Fatty Acid Desaturases in Rat Liver Microsomes," Biosci. Biotech. Biochem., vol. 60, No. 10, pp. 1672-1676 (1996).

H. Keen, et al., "Treatment of Diabetic Neuropathy with γ-Linolenic Acid," Diabetes Care, vol. 16, pp. 8-15 (Jan. 1993).

W. Khan, et al., "Arachidonic Acid and Free Fatty Acids as Second Messengers and The Role of Protein Kinase C," Cellular Signalling, vol. 7, No. 3, pp. 171-184 (1995).

P. Lai, et al., "Cell Cylce Arrest and Induction of Apoptosis in Pancreatic Cancer Cells Exposed to Eicosapentaenoic Acid In Vitro," British Journal of Cancer, vol. 74, pp. 1375-1383 (1996).

A. Leonard, et al., "cDNA Cloning and Characterization of Human $\Delta^5$-Desaturase Involved in the Biosynthesis of Arachidonic Acid," Biochem. J., vol. 347, pp. 719-724 (2000).

L. Lippiello, et al., "The Associate of Lipid Abnormalities With Tissue Pathology In Human Osteoarthritic Articular Cartilage," Metabolism, vol. 40, No. 6, pp. 571-576 (1991).

M. Manku, et al., "Essential Fatty Acids in the Plasma Phospholipids of Patients with Atopic Eczema," British Journal of Dermatology, vol. 110, pp. 643-648 (1984).

A. Marquardt, et al., "cDNA Cloning, Genomic Structure, and Chromosomal Localization of Three Members of the Human Fatty Acid Desaturase Family," Genomics, vol. 66, pp. 175-183 (2000).

P. Mayser, et al., "Omega-3 Fatty Acid-Based Lipid Infusion in Patients with Chronic Plaque Psoriasis: Results of a Double-blind and Randomized, Placebo-controlled, Multicenter Trial," Journal of the American Academy of Dermatology, vol. 38, No. 4, pp. 539-547 (1998).

V. Mimouni, et al., "Altered Desaturase Activities and Fatty Acid Composition in Liver Microsomes of Spontaneously Diabetic Wistar BB Rat," Biochimica et Biophysica Acta, vol. 1123, pp. 296-3302 (1992).

E. Navarro, et al., "Abnormal Fatty Acid Pattern in Rheumatoid Arthritis, A Rationale For Treatment with Marine and Botanical Lipids," The Journal of Rheumatology, vol. 27, pp. 298-303 (2000).

M. Obukowicz, et al., "Identification and Characterization of a Novel $\Delta^6/\Delta^5$ Fatty Acid Desaturase Inhibitor as a Potential Anti-Inflammatory Agent," Biochemical Pharmacology, vol. 55, pp. 1045-1058 (1998).

J. Plumb, et al., "Effect of Polyunsaturated Fatty Acids on the Drug Sensitivity of Human Tumor Cell Lines Resistant to either Cisplatin or Doxorubicin." British Journal of Cancer, vol. 67, pp. 728-733 (1993).

C. Russo, et al., "Increased Membrane Ratios of Metabolite to Precursor Fatty Acid in Essential Hypertension," Hypertension, vol. 4, pp. 1058-1063 (1997).

J. Seegers, et al., "Effects of Gamma-Linolenic Acid and Arachidonic Acid on Cell Cycle Progression and Apoptosis Induction in Normal and Transformed Cells," Prostaglandins, Leukotrienes and Essential Fatty Acids, vol. 56, No. 4, pp. 271-280 (1997).

S. Tadeka, et al., "Mechanism of Lipid Peroxidation in Cancer Cells in Response to γ-Linolenic Aid (GLA) Analyzed by GC-MS (I): Conjugated Dienes with Peroxyl (or Hydroperoxyl) Groups and Cell-Killing Effects," Anticancer Research, vol. 13, pp. 193-200 (1993).

T. Watanabe, et al., "The Effect of a Newly Developed Ointment Containing Eicosapentaenoic Acid and Docosahexaenoic Acid in The Treatment of Atopic Dermatitis," The Journal of Medical Investigation, vol. 46, pp. 173-177 (1999).

J. Weber, et al., "Greater Sensitivity of Human Multidrug-Resistant (mdr) Cancer Cells to Poly-Unsaturated Fatty Acids Than Their Non-mdr Counterparts," Journal of the National Cancer Institute, vol. 86, No. 8, (1994).

S. Wigmore, et al., "Down-Regulation of the Acute-Phase Response in Patients with Pancreatic Cancer Cachexia Receiving Oral Eicosapentaenoic Acid is Mediated Via Suppression of Interleukin-6," Clinical Science, vol. 92, pp. 215-221 (1997).

S. Wright, et al., "Oral Evening-Primrose-Seed Oil Improves Atopic Eczema," The Lancet, vol. 2, pp. 1120-1122 (1982).

GenBank Accession No. AAC23397.

GenBank Accession No. AF199596.

GenBank Accession No. AAF29378.

GenBank Accession No. AC004770.

EBI Accession No. AV722419.

* cited by examiner

```
-1357  CTCAGTGCTT GGGACAGTTA TGTTTCCTTT CCCTTTGAAG TGCCCAAATA CCAGTGTAAT
-1297  GAGAAATATG GCAGAGCCTG AGAGTTCAGA GCACAGGCCA GGGTCAAATC TCAGCCCTCC
-1237  ACTTACAAGC TGTGTGACAA AATAACCTCC CCCGGGCTCA GTTTCTTCAC TGTAAATTAG
-1177  GTTAATTGTT CCAACCTCAT AGGGTTGTTA GGAGAATTAA ATGAGTTAAG GTTTGCAAAA
-1117  CGCTAAGAAC AGTGCCTGGC ACACAGTAAG TGCTTTATAA AGTGTTTGTT GAATAAATAA
-1057  AATTTTGGAC CTAAACTCTG GGTCTCTTCA GGACTGCAAC AGCTTTGTAA CTGGCAACCC
 -997  CACTTTTAGG TGCGTTCCCA CTCCTCTAAA ACCCAGAGAT CTAAATGCCA AATCTCTCTG
 -937  CTTAAAAAGT CTCCCAGGGC TCCTAGGCGC CTCCAGGCTA GAACAGAAAT GCCTCAGCTT
 -877  GAAGACCCAG GCTTTTCAGG TGAAACACCT AAGGGTCAGG AGACGCTAGG ATCATCACTC
 -817  AAGGATCCCA GTGAATTTTT CCAAAATACA ATAAAAATAA AAACAAAAAG AGGCAAACAG
 -757  GGTTATAAAA ATTGTGGGGC ATTTTAAATG TTTCATTGAA CAAATTAAAG CATTAACAGC
 -697  CCTCCCCCAA CCACCACCAA GCCCAAGAGA CCGTAAATAT GCTGTTCACA AGATAACTGC
 -637  AACTTTCAAG GGCTCTCAGG CTGCTACTTC GGGCAGCACA ATTGGCGGCA CGACGTGGCA
 -577  AGCAGGCAGT AGTTTCCAAC CCTGGAGGGT CAGCGTCTGG AGACCCGGC CAAGGCATCC
 -517  ACAGCCTAAA GATGATGTCC GCGACCGCCC GGGCAGCCTC GTGCACGGAA AAACCTCAAC
 -457  CCCGGCCCCG CCCACCCTTC CTGCGGCCAC CCGCAGCCC TGGCCCCTCA GTCCATCCAC
 -397  TCCTGCAGCG CGGCCCCGCA CCCAGGGCCT GCACTAGAAC CGCTGTTCCT ACCGCGGCGC
 -337  CCCCTGGGAG CCAACGCCGC GATGCCCGCC TGACGTCAGG AAGTCGAATC CGGCGGCGAC
 -277  GCCTTTAGGG AGCCCGCGAG GGGGCGCGTG TTGGCAGCCC AGCTGTGAGT TGCCAAGAC
 -217  CCACCGGGGG ACGGGATCTC GCTCCCCGCG CCACGAGGCT CGGCCAATGG GAACGCGCGC
 -157  TGCGAGGCCC GCCGGTCTGC CCTGCGGTGC TGAAAACCCG GCGCGCAGGC GGCTGGCTCT
  -97  GGGCGCGCGC CAGCAAATCC ACTCCTGGAG CCCGCGGACC CCGAGCACGC GCCTGACAGC
  -37  CCCTGCTGGC CCGGCGCGCG GCGTCGCCAG GCCAGCT
```

FIGURE 1

| | | | | | | |
|---|---|---|---|---|---|---|
|ATGGCCCCCG|ACCCGGTGCA|GACCCCTGAC|CCGGCCTCCG|CCCAGCTCCG|CCAAATGCGC|60|
|TACTTTACTT|GGGAGGAGGT|GGCGCACGGC|TCCGGGAGGG|AGAAGGAGCG|ATGGCTCGTG|120|
|ATCGACCGGA|AGTGTACAA|CATCAGCGAC|TTCAGTCGCC|GCCACCCGGG|AGGCTCCCGG|180|
|GTCATCAGCC|ACTACGCTGG|TCAGGATGCC|ACGGATCCTT|TTGTGGCATT|CCACATTAAC|240|
|AAGGGCCTTG|TGAGAAAGTA|TATGAACTCT|CTTCTGATTG|GAGAGCTAGC|TCCGGAGCAG|300|
|CCCAGCTTTG|AACCCACCAA|GAATAAGGCG|CTCACTGATG|AATTCCGGGA|GCTGCGGGCC|360|
|ACAGTGGAGC|GAATGGGCCT|CATGAAAGCC|AACCATCTCT|TCTTCCTGTT|CTATCTGCTG|420|
|CACATCCTGC|TGCTGGACGT|GGCCCGCCTG|CTCACTCTTT|GGATCTTTTGG|AACTTCCTTG|480|
|GTGCCCTTCA|CCCTCTGTGC|AGTGCTGCTC|AGTACAGTTC|AGGCCCAGGC|AGGTTGGCTA|540|
|CAGCATGACT|TGGGCACCT|GTCCGTCTTC|AGCACCTCAA|CATGGAATCA|CCTGGTACAT|600|
|CATTTGTCA|TTGGCCACCT|GAAGGGGGC|CCAGCCAGCT|GGTGGAACCA|CATGCATTTC|660|
|CAGACCACG|CCAAGCCCAA|CTGCTTCCGC|AAAGACCCCG|ATATCAACAT|GCATCCCCTC|720|
|TTCTTCGCCC|TGGGGAAGGT|CCTTTTCTGTG|GAGCTTGGGA|AAGAAAAGAA|GAAGCACATG|780|
|CCATACAACC|ATCAGCACAA|GTACTTCTTC|CTGATTGGAC|CCCCAGCCTT|GCTGCCTCTC|840|
|TACTTCCAGT|GGTACATTTT|CTATTTGTT|GTTCAGCGGA|AGAAATGGGT|GGACTTGGCC|900|
|TGGATGCTCA|GCTTCTATGT|TCGTGTCTTC|TTCACTTACA|TGCCGCTGCT|GGGGCTGAAA|960|
|GGCCTCCTAT|GTCTTTTCTT|CATTGTCAGG|TTCCTGGAGA|GCAACTGGTT|TGTGTGGGTG|1020|
|ACGCAGATGA|ACCATATCCC|GATCATGACC|CAGTCAGCCT|GGAATGTGGA|CTGGGTCTCC|1080|
|ACCAGCTAC|AGGCAACCTG|CAACGTTCAC|TTCCCTACGA|TCAACAACTG|GTTCAGTGGC|1140|
|CACCTCAATT|TCCAGATTGA|ACACCACCTC|ACACACACA|TGCCACGACA|CAACTACCAC|1200|
|AAGGTGGCAC|CCCTGGTACA|ATCTCTGTGC|GCCAAGTACG|GCATCAAGTA|TGAGTCCAAG|1260|
|CCCCTGCTCA|CGGCCTTCGC|GGACATTGTT|TACTCCCTGA|AGGAGTCAGG|ACAGCTCTGG|1320|
|CTAGATGCCT|ATCTTCACCA|ATAA| | | |1344|

FIGURE 2

```
MAPDPVQTPD  PASAQLRQMR  YFTWEEVAHG  SGREKERWLV  IDRKVYNISD  FSRRHPGGSR   60
VISHYAGQDA  TDPFVAFHIN  KGLVRKYMNS  LLIGELAPEQ  PSFEPTKNKA  LTDEFRELRA  120
TVERMGLMKA  NHLFFLFYLL  HILLLDVAAW  LTLWIFGTSL  VPFTLCAVLL  STVQAQAGWL  180
QHDFGHLSVF  STSTWNHLVH  HFVIGHLKGA  PASWNHMHF   QHHAKPNCFR  KDPDINMHPL  240
FFALGKVLSV  ELGKEKKKHM  PYNHQHKYFF  LIGPPALLPL  YFQWYIFYFV  VQRKKWVDLA  300
WMLSFYVRVF  FTYMPLLGLK  GLLCLFFIVR  FLESNWFVNV  TQMNHIPMHI  DHDRNVDWVS  360
TQLQATCNVH  QSAFNNWFSG  HLNFQIEHHL  FPTMPRHNYH  KVAPLVQSLC  AKYGIKYESK  420
PLLTAFADIV  YSLKESGQLW  LDAYLHQ                                         448
```

FIGURE 3

```
MAPDPVAAET AAQGPTPRYF TWDEVAQRSG CEERWLVIDR KVYNISEFTR RHPGGSRVIS    60
HYAGQDATDP FVAFHINKGL VKKYMNSLLI GELSPEQPSF EPTKNKELTD EFRELRATVE   120
RMGLMKANHV FFLLYLLHIL LLDGAAWLTL WVFGTSFLPF LLCAVLLSAV QAQAGWLQHD   180
FGHLSVFSTS KWNHLLHHFV IGHLKGAPAS WWNHMHFQHH AKPNCFRKDP DINMHPFFFA   240
LGKILSVELG KQKKKYMPYN HQHKYFFLIG PPALLPLYFQ WYIFYFVIQR KKWVDLAWMI   300
TFYVRFFLTY VPLLGLKAFL GLFFIVRFLE SNWFVWVTQM NHIPMHIDHD RNMDWVSTQL   360
QATCNVHKSA FNDWFSGHLN FQIEHHLFPT MPRHNYHKVA PLVQSLCAKH GIEYQSKPLL   420
SAFADIIHSL KESGQLWLDA YLHQSRGPFE GKPIPNPLLG LDSTRTGHHH HHH          474
```

FIGURE 4

SEQUENCE LISTING

<160> NUMBER OF SEQ ID NOS: 15

<210> SEQ ID NO 1
<211> LENGTH: 1357
<212> TYPE: DNA
<213> ORGANISM: Homo sapiens

<400> SEQUENCE: 1

| | | | | | |
|---|---|---|---|---|---|
| ctcagtgctt | gggacagtta | tgtttccttt | ccctttgaag | tgcccaaata | ccagtgtaat | 60 |
| gagaaatatg | gcagagcctg | agagttcaga | gcacaggcca | gggtcaaatc | tcagccctcc | 120 |
| acttacaagc | tgtgtgacaa | aataacctcc | cccgggctca | gtttcttcac | tgtaaattag | 180 |
| gttaattgtt | ccaacctcat | agggttgtta | ggagaattaa | atgagttaag | gtttgcaaaa | 240 |
| cgctaagaac | agtgcctggc | acacagtaag | tgctttataa | agtgtttgtt | gaataaataa | 300 |
| aattttggac | ctaaactctg | gtctcttca | ggactgcaac | agctttgtaa | ctggcaaccc | 360 |
| cactttagg | tgcgttccca | ctcctctaaa | acccagagat | ctaaatgcca | aatctctctg | 420 |
| cttaaaaagt | ctcccagggc | tcctaggcgc | ctccaggcta | aacagaaat | gcctcagctt | 480 |
| gaagacccag | gcttttcagg | tgaaacacct | aagggtcagg | agacgctagg | atcatcactc | 540 |
| aaggatccca | gtgaattttt | ccaaaataca | ataaaaataa | aaacaaaaag | aggcaaacag | 600 |
| ggttataaaa | attgtggggc | atttaaatg | tttcattgaa | caaattaaag | cattaacagc | 660 |
| cctcccccaa | ccaccaccaa | gcccaagaga | ccgtaaatat | gctgttcaca | agataactgc | 720 |
| aactttcaag | ggctctcagg | ctgctacttc | gggcagcaca | attggcggca | cgacgtggca | 780 |
| agcaggcagt | agtttccaac | cctggagggt | cagcgtctgg | agaccccggc | caaggcatcc | 840 |
| acagcctaaa | gatgatgtcc | gcgaccgccc | gggcagcctc | gtgcacggaa | aaacctcaac | 900 |
| cccggcccg | cccaccccttc | ctgcggccac | cccgcagccc | tggcccctca | gtccatccac | 960 |
| tcctgcagcg | cggccccgca | cccagggcct | gcactagaac | cgctgttcct | accgcggcgc | 1020 |
| cccctgggag | ccaacgccgc | gatgcccgcc | tgacgtcagg | aagtcgaatc | cggcggcgac | 1080 |
| gcctttaggg | agcccgcgag | ggggcgcgtg | ttggcagccc | agctgtgagt | tgcccaagac | 1140 |
| ccaccggggg | acgggatctc | gctccccgcg | ccacgaggct | cggccaatgg | gaacgcgcgc | 1200 |
| tgcgaggccc | gccggtctgc | cctgcggtgc | tgaaaacccg | gcgcgcaggc | ggctggctct | 1260 |
| gggcgcgcgc | cagcaaatcc | actcctggag | cccgcggacc | ccgagcacgc | gcctgacagc | 1320 |
| ccctgctggc | ccggcgcgcg | gcgtcgccag | gccagct | | | 1357 |

<210> SEQ ID NO 2
<211> LENGTH: 1344
<212> TYPE: DNA
<213> ORGANISM: Rattus norvegicus

<400> SEQUENCE: 2

| | | | | | |
|---|---|---|---|---|---|
| atggccccg | acccggtgca | gaccctgac | ccggcctccg | cccagctccg | ccaaatgcgc | 60 |
| tactttactt | gggaggaggt | ggcgcacggc | tccgggaggg | agaaggagcg | atggctcgtg | 120 |
| atcgaccgga | aggtgtacaa | catcagcgac | ttcagtcgcc | gccacccggg | aggctcccgg | 180 |
| gtcatcagcc | actacgctgg | tcaggatgcc | acggatcctt | tgtggcatt | ccacattaac | 240 |
| aagggccttg | tgagaaagta | tatgaactct | cttctgattg | gagagctagc | tccggagcag | 300 |
| cccagctttg | aacccaccaa | gaataaggcg | ctcactgatg | aattccggga | gctgcgggcc | 360 |
| acagtggagc | gaatgggcct | catgaaagcc | aaccatctct | tcttcctgtt | ctatctgctg | 420 |

-continued

```
cacatcctgc tgctggacgt ggccgcctgg ctcactcttt ggatctttgg aacttccttg     480
gtgcccttca ccctctgtgc agtgctgctc agtacagttc aggcccaggc aggttggcta     540
cagcatgact ttgggcacct gtccgtcttc agcacctcaa catggaatca cctggtacat     600
cattttgtca ttggccacct gaaggggggcc ccagccagct ggtggaacca catgcatttc    660
cagcaccacg ccaagcccaa ctgcttccgc aaagaccccg atatcaacat gcatcccctc     720
ttcttcgccc tggggaaggt cctttctgtg agcttggga aagaaaagaa gaagcacatg      780
ccatacaacc atcagcacaa gtacttcttc ctgattggac ccccagcctt gctgcctctc     840
tacttccagt ggtacatttt ctattttgtt gttcagcgga agaaatgggt ggacttggcc     900
tggatgctca gcttctatgt tcgtgtcttc ttcacttaca tgccgctgct ggggctgaaa     960
ggcctcctat gtcttttctt cattgtcagg ttcctggaga gcaactggtt tgtgtgggtg    1020
acgcagatga accatatccc catgcacatt gatcatgacc ggaatgtgga ctgggtctcc    1080
acccagctac aggcaacctg caacgttcac cagtcagcct caacaactg gttcagtggc     1140 cacctcaatt tccagattga acaccactc ttccctacga tgccacgaca caactaccac     1200
aaggtggcac ccctggtaca atctctgtgc gccaagtacg gcatcaagta tgagtccaag    1260
cccctgctca cggccttcgc ggacattgtt tactccctga aggagtcagg acagctctgg    1320
ctagatgcct atcttcacca ataa                                           1344
```

<210> SEQ ID NO 3
<211> LENGTH: 447
<212> TYPE: PRT
<213> ORGANISM: Rattus norvegicus

<400> SEQUENCE: 3

```
Met Ala Pro Asp Pro Val Gln Thr Pro Asp Pro Ala Ser Ala Gln Leu
  1               5                  10                  15

Arg Gln Met Arg Tyr Phe Thr Trp Glu Val Ala His Gly Ser Gly
             20                  25                  30

Arg Glu Lys Glu Arg Trp Leu Val Ile Asp Arg Lys Val Tyr Asn Ile
         35                  40                  45

Ser Asp Phe Ser Arg Arg His Pro Gly Gly Ser Arg Val Ile Ser His
     50                  55                  60

Tyr Ala Gly Gln Asp Ala Thr Asp Pro Phe Val Ala Phe His Ile Asn
 65                  70                  75                  80

Lys Gly Leu Val Arg Lys Tyr Met Asn Ser Leu Leu Ile Gly Glu Leu
                 85                  90                  95

Ala Pro Glu Gln Pro Ser Phe Glu Pro Thr Lys Asn Lys Ala Leu Thr
            100                 105                 110

Asp Glu Phe Arg Glu Leu Arg Ala Thr Val Glu Arg Met Gly Leu Met
        115                 120                 125

Lys Ala Asn His Leu Phe Phe Leu Phe Tyr Leu Leu His Ile Leu Leu
    130                 135                 140

Leu Asp Val Ala Ala Trp Leu Thr Leu Trp Ile Phe Gly Thr Ser Leu
145                 150                 155                 160

Val Pro Phe Thr Leu Cys Ala Val Leu Leu Ser Thr Val Gln Ala Gln
                165                 170                 175

Ala Gly Trp Leu Gln His Asp Phe Gly His Leu Ser Val Phe Ser Thr
            180                 185                 190

Ser Thr Trp Asn His Leu Val His His Phe Val Ile Gly His Leu Lys
        195                 200                 205
```

```
Gly Ala Pro Ala Ser Trp Trp Asn His Met His Phe Gln His His Ala
    210                 215                 220
Lys Pro Asn Cys Phe Arg Lys Asp Pro Asp Ile Asn Met His Pro Leu
225                 230                 235                 240
Phe Phe Ala Leu Gly Lys Val Leu Ser Val Glu Leu Gly Lys Glu Lys
                245                 250                 255
Lys Lys His Met Pro Tyr Asn His Gln His Lys Tyr Phe Phe Leu Ile
                260                 265                 270
Gly Pro Pro Ala Leu Leu Pro Leu Tyr Phe Gln Trp Tyr Ile Phe Tyr
            275                 280                 285
Phe Val Val Gln Arg Lys Lys Trp Val Asp Leu Ala Trp Met Leu Ser
    290                 295                 300
Phe Tyr Val Arg Val Phe Thr Tyr Met Pro Leu Leu Gly Leu Lys
305                 310                 315                 320
Gly Leu Leu Cys Leu Phe Phe Ile Val Arg Phe Leu Glu Ser Asn Trp
                325                 330                 335
Phe Val Trp Val Thr Gln Met Asn His Ile Pro Met His Ile Asp His
                340                 345                 350
Asp Arg Asn Val Asp Trp Val Ser Thr Gln Leu Gln Ala Thr Cys Asn
            355                 360                 365
Val His Gln Ser Ala Phe Asn Asn Trp Phe Ser Gly His Leu Asn Phe
    370                 375                 380
Gln Ile Glu His His Leu Phe Pro Thr Met Pro Arg His Asn Tyr His
385                 390                 395                 400
Lys Val Ala Pro Leu Val Gln Ser Leu Cys Ala Lys Tyr Gly Ile Lys
                405                 410                 415
Tyr Glu Ser Lys Pro Leu Leu Thr Ala Phe Ala Asp Ile Val Tyr Ser
            420                 425                 430
Leu Lys Glu Ser Gly Gln Leu Trp Leu Asp Ala Tyr Leu His Gln
    435                 440                 445

<210> SEQ ID NO 4
<211> LENGTH: 473
<212> TYPE: PRT
<213> ORGANISM: Homo sapiens

<400> SEQUENCE: 4

Met Ala Pro Asp Pro Val Ala Ala Glu Thr Ala Ala Gln Gly Pro Thr
1               5                   10                  15
Pro Arg Tyr Phe Thr Trp Asp Glu Val Ala Gln Arg Ser Gly Cys Glu
            20                  25                  30
Glu Arg Trp Leu Val Ile Asp Arg Lys Val Tyr Asn Ile Ser Glu Phe
        35                  40                  45
Thr Arg Arg His Pro Gly Gly Ser Arg Val Ile Ser His Tyr Ala Gly
    50                  55                  60
Gln Asp Ala Thr Asp Pro Phe Val Ala Phe His Ile Asn Lys Gly Leu
65                  70                  75                  80
Val Lys Lys Tyr Met Asn Ser Leu Leu Ile Gly Glu Leu Ser Pro Glu
                85                  90                  95
Gln Pro Ser Phe Glu Pro Thr Lys Asn Lys Glu Leu Thr Asp Glu Phe
            100                 105                 110
Arg Glu Leu Arg Ala Thr Val Glu Arg Met Gly Leu Met Lys Ala Asn
        115                 120                 125
His Val Phe Phe Leu Leu Tyr Leu Leu His Ile Leu Leu Leu Asp Gly
```

-continued

```
                130                 135                 140
Ala Ala Trp Leu Thr Leu Trp Val Phe Gly Thr Ser Phe Leu Pro Phe
145                 150                 155                 160

Leu Leu Cys Ala Val Leu Leu Ser Ala Val Gln Ala Gln Ala Gly Trp
                165                 170                 175

Leu Gln His Asp Phe Gly His Leu Ser Val Phe Ser Thr Ser Lys Trp
                180                 185                 190

Asn His Leu Leu His His Phe Val Ile Gly His Leu Lys Gly Ala Pro
                195                 200                 205

Ala Ser Trp Trp Asn His Met His Phe Gln His Ala Lys Pro Asn
210                 215                 220

Cys Phe Arg Lys Asp Pro Asp Ile Asn Met His Pro Phe Phe Phe Ala
225                 230                 235                 240

Leu Gly Lys Ile Leu Ser Val Glu Leu Gly Lys Gln Lys Lys Lys Tyr
                245                 250                 255

Met Pro Tyr Asn His Gln His Lys Tyr Phe Phe Leu Ile Gly Pro Pro
                260                 265                 270

Ala Leu Leu Pro Leu Tyr Phe Gln Trp Tyr Ile Phe Tyr Phe Val Ile
                275                 280                 285

Gln Arg Lys Lys Trp Val Asp Leu Ala Trp Met Ile Thr Phe Tyr Val
290                 295                 300

Arg Phe Phe Leu Thr Tyr Val Pro Leu Leu Gly Leu Lys Ala Phe Leu
305                 310                 315                 320

Gly Leu Phe Phe Ile Val Arg Phe Leu Glu Ser Asn Trp Phe Val Trp
                325                 330                 335

Val Thr Gln Met Asn His Ile Pro Met His Ile Asp His Asp Arg Asn
                340                 345                 350

Met Asp Trp Val Ser Thr Gln Leu Gln Ala Thr Cys Asn Val His Lys
                355                 360                 365

Ser Ala Phe Asn Asp Trp Phe Ser Gly His Leu Asn Phe Gln Ile Glu
                370                 375                 380

His His Leu Phe Pro Thr Met Pro Arg His Asn Tyr His Lys Val Ala
385                 390                 395                 400

Pro Leu Val Gln Ser Leu Cys Ala Lys His Gly Ile Glu Tyr Gln Ser
                405                 410                 415

Lys Pro Leu Leu Ser Ala Phe Ala Asp Ile Ile His Ser Leu Lys Glu
                420                 425                 430

Ser Gly Gln Leu Trp Leu Asp Ala Tyr Leu His Gln Ser Arg Gly Pro
                435                 440                 445

Phe Glu Gly Lys Pro Ile Pro Asn Pro Leu Leu Gly Leu Asp Ser Thr
450                 455                 460

Arg Thr Gly His His His His His His
465                 470
```

<210> SEQ ID NO 5
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 5
cacgacgaat tccgtcgcca ggccagctat gg    32

<210> SEQ ID NO 6

```
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 6
cactatctcg agctgggcag ggtggctgtt gt                              32

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 7
cacgcgaagc ttaaaaatgg cccccgaccc gg                              32

<210> SEQ ID NO 8
<211> LENGTH: 44
<212> TYPE: DNA
<213> ORGANISM: Artificial Sequence
<220> FEATURE:
<223> OTHER INFORMATION: Description of Artificial Sequence:primer

<400> SEQUENCE: 8
cacgcgtcta gattattggt gaagataggc atctagccag cgct                 44

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence:primer

<400> SEQUENCE: 9
cacgcgtcta gattggtgaa gataggcatc tagccagagc tg                   42

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 10
cacgcgaagc ttaaaaatgg cccccgaccc gg                              32

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence:primer

<400> SEQUENCE: 11
cacgcgtcta gattattggt gaagataggc atctagccag cgct                 44

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 12
```

-continued

```
caccttacgg tcgatcacta                                                  20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 13
ctcagtgctt gggacagtta                                                  20

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 14
gacgagctcc tcagtgcttg ggacagttat gttt                                  34

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 15
gacgagctca gctggcctgg cga                                              23
```

METHODS FOR SCREENING COMPOUNDS THAT MODULATE LIPID METABOLISM

CROSS REFERENCE TO RELATED APPLICATIONS

This application is the National Stage of International Application No. PCT/CA01/01520 filed Oct. 26, 2001, which claims priority to U.S. Provisional Application No. 60/243,009, filed Oct. 26, 2000.

FIELD OF THE INVENTION

This invention relates to the identification of nucleotides, proteins, compounds and/or pharmacological agents that either inhibit or enhance the activity of fatty acid desaturase enzymes involved in lipid metabolism and/or effectively regulate the level of expression of the desaturase genes.

BACKGROUND OF THE INVENTION

Diabetes mellitus represents a collection of genetically determined disorders one of which is the altered metabolism of lipids associated with a deficiency of insulin or insulin resistance. Diabetics are prone to certain long-term complications. The range of medical problems includes cardiovascular disease, retinopathy, nephropathy, and neuropathy. The latter condition is a neuropathological disorder of the peripheral nervous system, which leads to a reduction in nerve conduction velocity in both motor and sensory nerves. The pathophysiology of diabetic peripheral neuropathy could be associated with the abnormal metabolism of essential fatty acids (Julu P., 1998, in *Essential Fatty Acids and Eicosanoids*, AOCS Press, Ill., U.S.A.,pp. 168-175). This abnormal or altered lipid metabolism is reflected in the lack of incorporation of n-6 fatty acids in membrane phospholipids (Coste et al., 1999, *J. Nutr. Biochem.*, 10: 411-420). Evidence from experimental diabetes studies in animals indicates that the biosynthesis of polyunsaturated fatty acids (PUFAs) by the desaturation and elongation systems is impaired. A multi-center clinical trial supported by Scotia Pharmaceuticals (UK) has demonstrated that providing n-6 fatty acids, such as gamma-linolenic acid (GLA), to patients with mild diabetic neuropathy alleviates the course of the disease (Keen et al., 1993, *Diabetes Care*, 16: 8-15).

PUFAs are also known to cause cell cycle arrest, induction of apoptosis, inhibition of mitosis (Seegers et al., 1997, *Prostaglandins Leukot. Essent. Fatty Acids*, 56: 271-280 and Lai et al., 1996, *Br. J. Cancer*, 74: 1375-1383) and cell proliferation (Calviello et al., 1998, *Int. J. Cancer*, 75: 699-705), reduction of tumor-endothelium adhesion, improvement of gap junction communications of the endothelium (Jiang et al., 1997, *Prostaglandins Leukot. Essent Fatty Acids*, 56: 307-316), inhibition of urokinases (du Toit et al., 1994, *Prostaglandins Leukot. Essent. Fatty Acids*, 51: 121-124) reduction of the effects of growth factors on cancer cells (Jiang et al., 1995b, *Br. J. Cancer*, 71: 744-752), reversion of multi-drug resistance (Weber et al., 1994, *J. Nat Cancer Inst.*, 86: 638-639), and increase of the cytotoxic effects of chemotherapeutic agents (Plumb et al., 1993, *Br. J. Cancer*, 67: 728-733 and Anderson et al., 1998, *Anticancer Res.*, 18: 791-800).

N-3 and n-6 fatty acids follow a similar route of metabolism and it is likely that individual enzymes act on similar substrates in both PUFA families. In the n-6 pathway dihomogammalinolenic acid (DGLA, 20:3n-6) is converted to arachidonic acid (AA, 20:4n-6) through desaturation by an enzyme known as delta-5-desaturase (D5D). This enzyme also produces eicosapentaenoic acid (EPA, 20:5n-3) from delta 8, 11, 14, 17 eicosatetraenoic (20:4n-3) in the n-3 pathway.

Delta-5-desaturase belongs to a subclass of enzymes known as "front-end" desaturases, which introduce double bonds into the acyl chain between the carboxyl group and an existing double bond. Delta-5-desaturase is an enzyme bound to the membrane of the endoplasmic reticulum, which is part of a system that consists of three major proteins associated with an electron transport chain (Fujiwara et al., 1983, *Biochem. Biophys. Res. Commmun*, 110: 36-41 and 1984, *Arch. Biochem. Biophys.*, 233: 402-407). The cloning, expression and fatty acid regulation of the human delta-5-desaturase has been previously described (Cho et al., 1999b, *J. Biol. Chem.*, 274: 37335-37339; Leonard et al., 2000, *Biochem. J.*, 347: 719-724 and Marquardt et al., 2000, *Genomics*, 66: 175-183).

Both arachidonic acid (AA) and eicosapentaenoic acid (EPA), direct products of delta-5-desaturase, have been proposed as key PUFAs associated with a variety of diseases. A chronic cellular imbalance between AA and EPA and their respective eicosanoid derivatives may have major health implications. This imbalance has been implicated in arterial hypertension, hypercholesterolemia, atherosclerotic heart disease, chronic inflammatory and autoimmune disorders, allergic eczema and other atopic disorders (Booyens et al., 1985, *Med. Hypotheses*, 18: 53-60). In this regard, the fatty acid analysis of a group of the plasma phospholipid fraction of patients with coronary heart disease revealed that the levels of AA, EPA, gamma-linolenic acid (GLA), and docosahexaenoic acid (DHA) are low. In patients with essential hypertension, linoleic acid (LA) and AA are also low. (Das U., 1995, *Prostaglandins Leukot. Essent Fatty Acids*, 52: 387-391). Furthermore, bioavailability of eicosanoid precursors, and in particular of AA, could affect several vascular functions and have a bearing on the pathogenesis or complications of hypertension (Russo et al., 1997, *Hypertension*, 4: 1058-1063). It has been also shown that the percentages of AA-containing species of phosphatidylcholine (PC) were lowered in the plasma of patients with hypercholesterolemia. The same PC species with AA were decreased in the patient's platelets (Dobner P, and Engelmann B., 1998, *Am. J. Physiol.*, 275: E777-E784).

In addition to serving as the precursor to eicosanoids and other bioactive molecules, AA may function as a second messenger (Khan et al., 1995, *Cell. Signal.*, 7: 171-184).

The proinflammatory eicosanoids prostaglandin $E_2$ and leukotriene $B_4$ are derived from AA, which is maintained at high cellular concentrations by the high n-6 and low n-3 polyunsaturated fatty acid content of the modern Western diet (James et al., 2000, *Am. J. Clin. Nutr.*, 71: 343S-348S). Recent results have suggested that by inhibiting delta-5-desaturation, the production of prostaglandin $E_2$ can be reduced with a concomitant reduction of inflammatory processes such as rheumatoid arthritis (Chavali S. R. and Forse R. A. 1999, *Prostaglandins Leukot Essent. Fatty Acids*, 61: 347-352; Navarro et al, 2000, *J. Rheumatol.*, 27: 298-303). Indeed, AA-derived eicosanoid are pro-inflammatory and regulate the functions of cells of the immune system. Consumption of fish oils leads to replacement of AA in cell membranes by EPA. This changes the amount and alters the balance of eicosanoids produced. Consumption of oils rich in EPA diminishes lymphocyte proliferation, T-cell-mediated cytotoxicity, natural killer cell activity, macrophage-mediated cytotoxicity, monocyte and neutrophil chemotaxis, major histocompatibility class II expression and antigen presentation, production of pro-inflammatory cytokines (interleukins 1 and 6, tumour necrosis factor) and adhesion molecule expression. (Calder P. C., 1998, *Braz. J. Med. Biol. Res.* 4: 467-490). In experimentally induced T-cell-mediated autoimmune disease, essential fatty acid-deficient diets or diets supplemented with n-3 fatty acids appear to augment disease, whereas n-6 fatty acids prevent or reduce the severity. The regulation of gene expression, signal transduction pathways, production of eicosanoids and cytokines, and the action of antioxidant enzymes are all mechanisms by which dietary n-6 and n-3 fatty acids may exert effects on the immune system and autoimmune disease. (Harbige L. S., 1998, *Proc. Nutr. Soc.*, 4: 555-562).

Patients with atopic dermatitis (eczema) have reduced levels of delta-5-desaturase products such as AA (Hansen A. E., 1933, *Proc. Soc. Exp. Biol. Med.*, 31: 1160-1161). These findings are consistent with the other studies in which eczema patients had low levels of serum AA (Manku et al., 1984, *Br. J. Dermatol.*, 110: 643-680). The therapeutic usefulness of n-6 PUFA supplementation in atopic eczema has been reported (Wright S. and Burton J. L., 1982, *Lancet*, 2: 1120-1122). These treatments are not restricted to n-6 PUFAs since beneficial effects have also been obtained using an ointment containing EPA and DHA (Watanabe T. and Kuroda Y., 1999, *J. Med. Invest.*, 46: 173-177).

Psoriasis is another disease associated with. It is a multifactorial skin disease characterized by a profound increase of free AA and its proinflammatory metabolites. Providing an alternative precursor (i.e. EPA) which competes with AA in the eicosanoid synthesis, the prominflammatory effect is reduced by inducing the production of less inflammatory and chemotactic derivatives with a concomitant reduction of the chronic plaque-type psoriasis (Mayser et al., 1998, *J. Am. Acad. Dermatol.* 38: 539-547).

Similarly, acute respiratory distress syndrome (ARDS) characterized by acute lung injury, is linked with excessive release of AA-derived inflammatory mediators and toxic oxygen radicals from activated intrapulmonary macrophages and neutrophils. Supplementation of nutritional formulas with combination of EPA and GLA which favors an anti-inflammatory state, is used as adjuvant therapy in the clinical management of patients with or at risk of developing ARDS (Gadek et al., 1999, *Crit. Care Med.* 27: 1409-1420).

There is also an association of lipid accumulation in general and AA, in particular, with histological severity of human joint pathology (Lippiello et al., 1991, *Metabolism* 40: 571-576). Recent findings demonstrate that n-3 fatty acid supplementation affects molecular mechanisms that regulate the expression of catabolic factors involved in articular cartilage degradation (ACD). This shows the beneficial role of n-3 PUFAs in mitigating the physiological parameters that cause and propagate arthritic disease (Curtis et al., 2000, *J. Biol. Chem.* 275: 721-724).

AA and EPA have varying effects on cancer in mammalian cells. Studies have shown that n-3 and n-6 PUFAs and/or their metabolites are able to modulate the expression of tumor suppressors (Jiang et al., 2000, *Prostaglandins Leukot. Essent Fatty Acids*, 62: 119-127), lead to antimetastatic mechanisms (Jiang et al., 1998a, *Br. J. Cancer*, 77: 731-738 and 1998b, *Biochem. Biophys. Res. Commun.*, 244: 414-420) and modulate the expression of cell adhesion molecules including E-cadherin, desmoglein and beta-catenin (Jiang et al., 1995, *Cancer Res.*, 55: 5043-5048 and Jiang et al., 2000, *Prostaglandins Leukot. Essent. Fatty Acids*, 62: 119-127).

In particular, EPA has been reported to significantly inhibit the growth of human pancreatic cancer cell lines in vitro (Falconer et al., 1994, *Br. J. Cancer*, 69: 826-832) and down-regulate the acute-phase response in patients with pancreatic cancer cachexia (Wigmore et al., 1997, *Clin. Sci.*, 92: 215-221). It has also been shown that following exposure to EPA, malignant cells generate much higher levels of potentially cytotoxic superoxide radicals and lipid peroxidation products (Takeda et al., 1993, *Anticancer Res.*, 13: 193-199).

Fungi, microalgae and rat liver microsomes have been used in different laboratories to test inhibitors of fatty acid delta-5-desaturase (Kawashima et al., 1996, *Biosci Biotech. Biochem.*, 60: 1672-1676 and Obukowicz et al., 1998, *Biochem. Pharmacol.*, 55: 1045-1058). However, these models which use different species are limited by the fact that they are not close enough to the desired target, i.e. the human delta-5-desaturase, for drug screening. Hence, it is desirable to develop an improved model and methodology for identifying-agents that modulate the activity of mammalian and, in particular, human fatty acid desaturases. The use of human delta-5-desaturase in whole cells, spheroplasts, and microsomes or as the purified enzyme from transformed yeast that overexpress the desaturase is a practical approach to test chemical libraries for modulators of the enzyme. The transformed yeast model also eliminates potential ethical concerns that may arise when human or mammalian tissues are used to obtain large amount of these enzymes for drug screening.

In this regard, an experimental model that can be manipulated to study the expression of genetic material isolated from humans and other species is needed to establish the role and function of these genes and their corresponding proteins in PUFA metabolism. This is particularly so in recognition of the fact that the relationship between a protein's unique role in a metabolic pathway and the expression of the gene encoding that protein is normally a well coordinated event such that subtle deviations can often lead to abnormal physiological processes. Moreover, such a system would facilitate the discovery and identification of candidate drug targets, which act at the DNA or protein level in order to correct abnormalities or imbalances in lipid metabolic changes associated with certain pathological conditions, such as diabetic neuropathy.

Towards developing such a system, it is critical to locate the control region for the delta-5-desaturase gene.

SUMMARY OF THE INVENTION

The present invention teaches an isolated nucleic acid comprising a DNA sequence selected from the group consisting of: (a) SEQ ID NO: 1; (b) a fragment of (a) having at least 15 nucleotides; (c) a sequence which is at least 90% homologous with (a), and; (d) a sequence which hybridizes to (a), (b) or (c) under stringent hybridization conditions. The invention includes a control region of a human delta-5-desaturase gene.

The present invention teaches an isolated nucleic acid comprising a DNA sequence selected from the group consisting of: (a) SEQ ID NO: 2; (b) a fragment of (a) having at least 15 nucleotides; (c) a sequence which is at least 90% homologous with (a), and; (d) a sequence which hybridizes to (a), (b) or (c) under stringent hybridization conditions. The invention includes a nucleotide sequence encoding a rat delta-5-desaturase gene.

The present invention teaches an isolated polypeptide comprising a polypeptide sequence selected from the group consisting of: (a) SEQ ID NO: 3; (b) a fragment of (a) having at least 15 nucleotides; (c) a sequence which is at least 90% homologous with (a) or its salt The invention includes a polypeptide sequence, which denotes a rat delta-5-desaturase protein.

The invention teaches a recombinant nucleic acid molecule comprising a control region of a mammalian delta-5-desaturase gene and a reporter gene, wherein the control region is transcriptionally linked to the reporter gene so as to effectively initiate, terminate or regulate transcription of the reporter gene The reporter gene can be selected from the group consisting of luciferase, chloramphenicol acetyl transferase (CAT), beta-galactosidase, alkaline phosphatase, placental alkaline phosphatase, glucuronide synthetase, green fluorescence protein (GFP) and human growth hormone.

The invention also teaches a vector construct containing the recombinant nucleic acid molecule of the invention, wherein the vector construct is capable of expressing the reporter gene to generate a reporter gene product that can be detected upon introduction of the vector construct into an appropriate host cell or host system. The invention further teaches a host cell or host system transformed or transfected with the vector construct. The host cell may be a mammalian cell or a human cell. The mammalian cell may be from the human cell lines, ZR-75-1 or HepG2.

The invention also teaches a method of screening for a modulator which is capable of modulating or regulating the transcriptional expression of a mammalian delta-5-desaturase gene, comprising the steps of: providing a host system containing a control region of mammalian delta-5-desaturase gene and a reporter gene operably associated with the control region, wherein the control region is effective to initiate, terminate or regulate a level of transcription of the reporter gene; contacting the host system with a test component; evaluating the level of transcription of the reporter gene, wherein a measurable difference in the level of transcription of the reporter gene in the presence of the test component compared to a control under identical conditions but in the absence of the test component is an indicator of an ability of the test component to transcriptionally modulate or regulate expression of the delta-5-desaturase gene; and selecting as the modulator the test component which exhibits said ability. The control region may have a DNA sequence represented by SEQ ID NO: 1, or a fragment thereof (see FIG. 1).

The invention further teaches a method of screening for a modulator which is capable of modulating the enzymatic activity of a functional mammalian delta-5-desaturase enzyme, comprising the steps of: providing a host system containing a nucleic acid sequence which encodes a mammalian delta-5-desaturase enzyme operably associated with a promoter region, wherein the promoter region is effective to initiate, terminate or regulate the level of expression of the nucleic acid sequence; contacting the host system with a test component; evaluating the enzymatic activity of the delta-5-desaturase, wherein a measurable difference in a level of lipid metabolite or associated cofactors in the presence of the test component compared to a control under identical conditions but in the absence of the test component is an indicator of the ability of the test component to modulate delta-5-desaturase enzyme activity; and selecting as the modulator a test component which exhibits said ability. The delta-5-desaturase enzyme may be from rat (SEQ ID NO: 3) or human.

The invention further teaches a method of screening for a modulator which is capable of modulating the enzymatic activity of a functional mammalian delta-5-desaturase enzyme, comprising the steps of: providing a host system the purified delta-5-desaturase protein, contacting the host system with a test component; evaluating the enzymatic activity of the delta-5-desaturase, wherein a measurable difference in a level of lipid metabolite or associated cofactors in the presence of the test component compared to a control under identical conditions but in the absence of the test component is an indicator of the ability of the test component to modulate delta-5-desaturase enzyme activity; and selecting as the modulator a test component which exhibits said ability. The delta-5-desaturase enzyme may be from mammalian (rat-SEQ ID NO: 3) or human.

The invention teaches a method of screening for a modulator according to any one of the screening methods of the invention, wherein the screening method is an assay for identifying test compounds that alter genes, gene products, proteins or compounds that are involved in modulating lipid metabolism and/or affect disease, including diabetic neuropathy.

The invention includes modulators identified by the screening methods of the invention. The modulator may be in a purified form. The invention includes pharmaceutical compositions comprising such a modulator and a pharmaceutically acceptable carrier or diluent.

The invention also teaches the use of a modulator or pharmaceutical composition comprising a modulator in purified form and a pharmaceutically acceptable carrier or diluent, identified according to any one of the screening methods of the invention, for the treatment of diseases, including those involving abnormal lipid metabolism, such as diabetic neuropathy.

The invention further teaches an isolated rat delta-5-desaturase gene (SEQ ID NO: 2), as well as a delta-5-desaturase protein having a linked tag sequence (see FIG. 4 for tagged human sequence), and includes a delta-5-desaturase protein, wherein the tag sequence is a V5 epitope or 6 histidine residues (6×His).

The invention further teaches a method of screening for a modulator which is capable of modulating the enzymatic activities of functional mammalian delta-5- and /or delta-6- enzymes within the same host system, comprising the steps of: providing a host system containing nucleic acid sequences which encode a mammalian delta-5- and delta-6-desaturase enzyme operably associated with a promoter regions, wherein the promoter regions are effective to initiate, terminate or regulate the level of expression of the nucleic acid sequence; contacting the host system with a test component; simultaneously evaluating the enzymatic activity of the delta-5-desaturase, wherein a measurable difference in a level of lipid metabolite or associated cofactors in the presence of the test component compared to a control under identical conditions but in the absence of the test component is an indicator of the ability of the test component to modulate delta-5-desaturase enzyme activity; and selecting as the modulator a test component which exhibits said ability. The delta-5-desaturase enzyme may be from rat (SEQ ID NO: 3) or human.

The invention further teaches the use of a modulator or pharmaceutical composition comprising a modulator in purified form and a pharmaceutically acceptable carrier or diluent, identified according to any one of the screening methods of the invention for the treatment of diseases involving fatty acid metabolism such as arterial hypertension, hypercholesterolemia, atherosclerotic heart disease, chronic inflammatory and autoimmune disorders, allergic eczema, and other atopic disorders.

BRIEF DESCRIPTION OF THE DRAWINGS

In the following description, the invention will be explained in detail with the aid of the accompanying figures, which illustrate preferred embodiments of the present invention and in which:

FIG. 1 shows the nucleic acid sequence of the human delta-5-desaturase (hD5D) control region from −1357 to −1 numbered relative to the translation initiation start codon, ATG (SEQ ID NO: 1);

FIG. 2 shows the nucleic acid sequence of the rat delta-5-desaturase (rD5D) coding portion of the fatty acid desaturase gene (SEQ ID NO: 2);

FIG. 3 shows the amino acid sequence of the rD5D enzyme (SEQ ID NO: 3);

FIG. 4 shows the amino acid sequence of the C-terminal tagged human D5D enzyme (SEQ ID NO: 4);

DETAILED DESCRIPTION OF EMBODIMENTS

Figure 5:
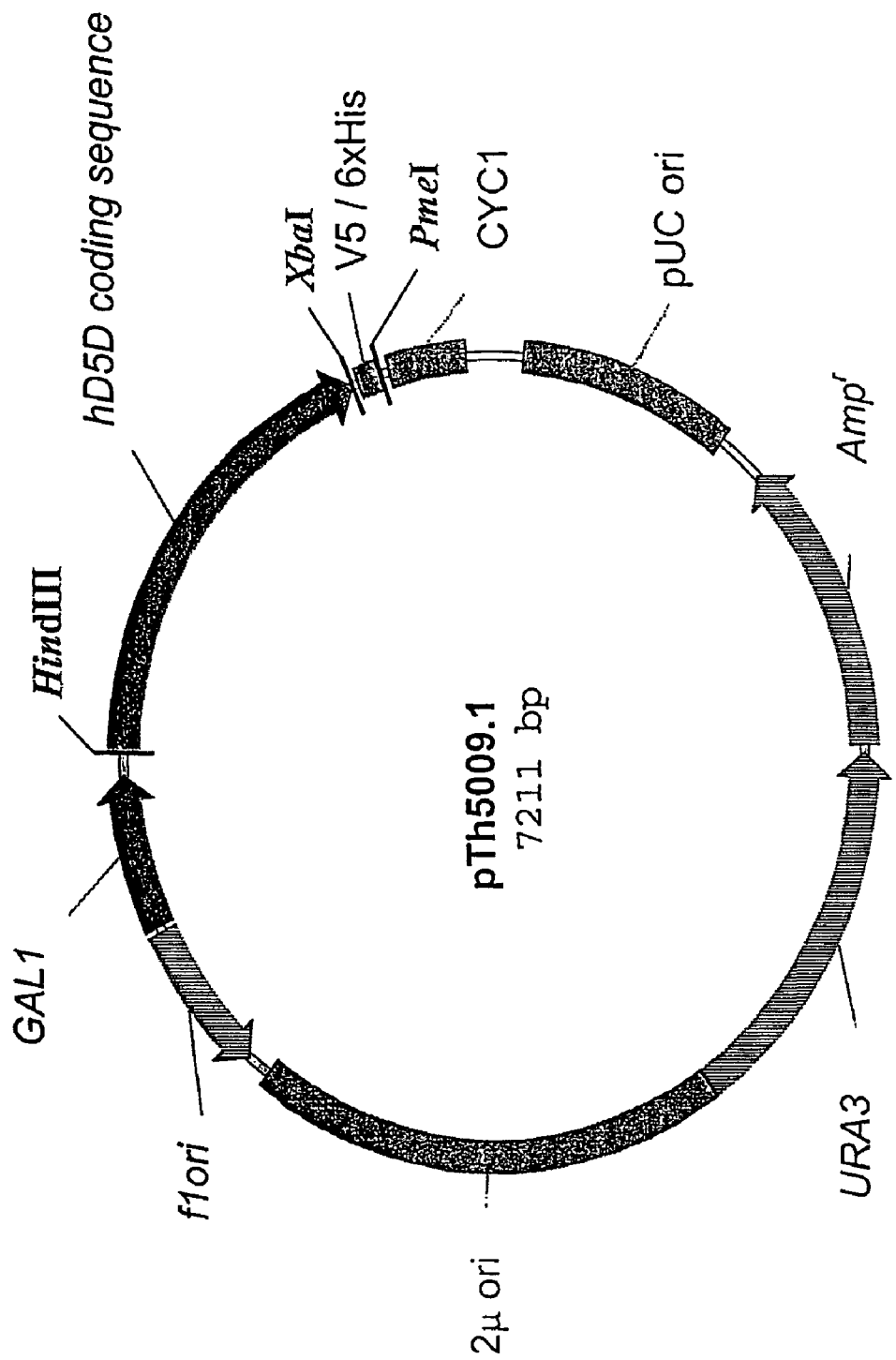
FIG. 5 is a schematic representation of plasmid pTh5009.1 (7211 bp) which contains the C-terminal tags. The human delta-5-desaturase coding sequence is shown between restriction sites for HindIII and XbaI.

The present invention evolved from observations that oral supplementation of naturally occurring fatty acids has had some therapeutic benefit in counteracting existing metabolic deficiencies prevalent in certain disease conditions. However, to address new strategies for therapeutic intervention, it was necessary to go beyond the measurement of lipid levels and lipid supplementation and directly measure actual enzyme activities and the regulation of expression of the genes from which these enzymes are encoded. While the pathways for the metabolic conversions of PUFAs are generally known, the human genes which are uniquely involved and responsible for expressing the various enzymes utilized along these pathways have hitherto been mostly uncharacterized. Presently, newly isolated human desaturase genes reveal sequence homology to other genes of known function but this information alone only provides an indication as to the possible types of relationships that might exist between these genes and the proteins they encode (Cho et al., 1999a, *J. Biol. Chem.*, 274: 471-477). Consequently, the isolation and identification of such useful portions of the genome (e.g. desaturase genes) leads to a need to develop the ability to more fully integrate this type of information with the biology of the cell or organism from which these genes are isolated.

In this regard, the present inventors have developed an experimental model, which can be manipulated to study the expression of genetic material isolated from humans and other species, to establish the role and function of these genes and their encoded proteins in PUFA metabolism. The relationship between a protein's unique role in a metabolic pathway and the expression of the gene encoding that protein is normally a well coordinated event such that subtle deviations can often lead to abnormal physiological processes. The present system thus facilitates the discovery and identification of candidate drugs, which act at the DNA or protein level in order to correct abnormalities or imbalances in lipid metabolic changes associated with certain pathological conditions, such as diabetic neuropathy.

The present invention is particularly directed to control of expression of mammalian delta-5-desaturase (D5D) enzyme and the use of its nucleic acid and amino acid sequences in expression vectors and host systems for drug screening methods. The inventors have isolated, cloned and identified the control region (i.e. promoter and other regulatory elements) for the human D5D gene. Genetic elements, which are responsible for controlling D5D gene expression, have thus been isolated independently of the desaturase gene encoding region (i.e. amino acid coding sequences) and are employed to assay for agents that modulate D5D gene expression. The drug screening methods provided herein are thus designed to identify test components which will modulate D5D activity or the level of D5D gene expression for their subsequent utilization in the treatment and/or prevention of certain pathological disorders, including those associated with abnormal lipid metabolism.

Accordingly, cloning the control region of the D5D gene provides a powerful tool for dissecting the role of D5D gene expression and inducing modifications thereof, which eliminate or control alterations associated with metabolic disorders. The identification and characterization of the promoter, enhancer and silencer regions of the D5D gene allows the present inventors to identify and understand the role of discrete regulatory elements located in the D5D control region as well as to discover potential pharmacological modulators of D5D gene expression.

D5D Control Region

Experimental work via reverse transcriptase-polymerase chain reaction (RT-PCR) showed that the intron/exon structure of hD5D (BC269730_2) as annotated for AC004770 in GenBank was essentially correct. Further investigation into this desaturase using 5'-RACE (rapid amplification of cDNA ends) on human liver cDNA revealed the presence of alternate splicing for this gene. This conclusion was arrived at by DNA sequencing the 5' end of a number of separate clones. It has been shown by others (Cho et al., 1999b, *J. Biol. Chem.*, 274: 37335-37339 and Leonard et al., 2000, *Biochem. J.*, 347: 719-724), as well as by the applicants, that hD5D is a gene encoding an active delta-5-desaturase.

In this regard, yeast cells were transformed with pTh5009.1 that contained the human D5D gene (see FIG. 5), or with pYES2/CT. The yeast transformed with pTh5009.1 converted 29% of DLL to AA whereas in the pYES2/CT-transformed yeast there was no such conversion. Such transformed yeast did not desaturate alpha-linolenic acid.

D5D was cloned by RT-PCR. Initially, cDNA was generated through reverse transcription of total RNA that was extracted from tissue expressing mammalian fatty acid desaturases using random primers (Perkin-Elmer). Subsequent amplification of desaturase cDNA was achieved by PCR using forward and reverse primers specifically designed to correspond to the coding sequence for the hD5D gene.

The oligonucleotide primers designed for amplification of mammalian desaturase cDNA may comprise one or more endonuclease recognition sites to facilitate cloning into an expression vector following amplification by PCR. In the present invention, the forward and reverse primers used for cloning the mammalian desaturase genes contain an EcoRI and a XhoI or a HindIII and a XbaI restriction site, respectively.

Optionally, an oligonucleotide primer may lack a translation initiation or termination codon so long as such codons are provided in the cloning vector, which must be operatively associated with the cDNA sequence encoding the mammalian desaturase (i.e. positioned upstream at the 5'-end or downstream at the 3'-end of the desaturase encoding sequence, respectively).

The translation initiation and termination codons can be provided within the forward and reverse primer sequences, respectively, the exception being that the primers used to create the tagged constructs lacked termination codons.

Examples of forward and reverse primers that are useful in cloning rD5D and hD5D cDNAs for insertion into expression vectors are listed below in Example 1.

A rD5D cDNA fragment spanning nucleotides +1 to +1344 was cloned by RT-PCR using total RNA extracted from rat liver tissue. The nucleotide sequence that encodes a functionally active rD5D is depicted in FIG. 2 (SEQ ID NO: 2). The rD5D protein is represented by the deduced amino acid sequence depicted in FIG. 3 (SEQ ID NO: 3).

An hD5D cDNA fragment spanning nucleotides +1 to +1335 was cloned from the human cell line Chang (ATCC No. CCL-13) by RT-PCR amplification of total RNA. The nucleotide sequence that encodes a functionally active hD5D is reported in GenBank Accession No. AF199596. The encoded hD5D is represented by the amino acid sequence reported in GenBank Accession No. AAF29378.

The hD5D control region was cloned from human leukocyte genomic DNA by PCR amplification. In a first PCR reaction, human genomic DNA prepared in the present inventors' laboratory served as template. According to GenBank Accession No. AC004770, synthetic reverse and forward primers starting at positions +126 of the hD5D CDS and position –1357 of the sequence upstream of the ATG respectively, were used to generate a fragment of 1483 bp.

The reverse and forward primers used in cloning the hD5D control region from nucleotide position +126 to –1357 from the translation initiation codon, ATG, are listed below in Example 2.

The PCR product corresponding to the expected fragment size was recovered, inserted into a TA cloning vector, preferably pCRII (Invitrogen), and then sequenced. Linearized cloning vectors for TA cloning contain a single 3' deoxythymidine (T) residue overhang to allow for efficient ligation of PCR products with 3' deoxyadenosine (A) overhangs. DNA products of PCR amplification contain a single 3' A overhang due to the nontemplate-dependent activity of Taq polymerases.

The pCRII/hD5D control region construct (pCh4012.1), contains 126 bp of hD5D CDS. The control region of hD5D referred to in the present invention starts at position –1 and ends at –1357 from the ATG. The size of the fragment is 1357 bp. The sequence is represented by SEQ ID NO:1 (FIG. 1).

Subcloning of the 1357 bp hD5D control region, into a reporter vector, following its insertion into the pCRII cloning vector was achieved by PCR amplification using a new set of forward and reverse primers. The PCR reaction also served to remove the 126 bp part of the hD5D CDS using the pCh4012.1 construct as template. The oligonucleotide primers used in subcloning the hD5D control region may advantageously comprise additional nucleotide sequences, which contain one or more endonuclease recognition sites to facilitate insertion and ligation into an expression vector following PCR amplification. In the present invention, the forward and reverse primers contain a SacI restriction site, at both ends. Optionally, an oligonucleotide primer may also contain a translation initiation codon (i.e. positioned downstream at the 5'-end of the reverse primer) which is operatively associated with a heterologous nucleic acid sequence encoding a gene product. In an embodiment of the present invention, the translation initiation codon is not provided within the reverse primer sequence but is supplied instead from the 5'-end of the heterologous nucleic acid sequence, which is ligated to the 3'-end of the control region.

Examples of forward and reverse primers that were used for cloning the hD5D control region from position –1357 to –1 from the translation initiation codon, ATG, are listed below in Example 3.

*Escherichia coil* is a preferred specific prokaryotic host for cloning and replicating the DNA sequence of the present invention. On the other hand, yeast, in particular *Saccharomyces cerevisiae*, is the preferred host used for expression of mammalian desaturase coding sequences.

Vector Construction

Accordingly, a vector construct of the present invention includes essential elements for its proliferation and selection in both eukaryotic and prokaryotic cells. Expression vectors of the invention include pYES2 and pYES2/CT (Invitrogen) which essentially comprise an origin of replication, an inducible promoter and two selectable marker genes. In particular, the pYES2/CT vector also contains a short DNA sequence that encodes for tags (e.g. V5/6×His epitopes) which allow the translated product, a tagged desaturase protein, to be easily identified and/or purified using commercially available antibodies and/or affinity chromatography columns. The pYES2 and pYES2/CT vectors, confer uracil prototrophy for selection in yeast, and a GAL1 galactose-inducible promoter for expression which is activated in the presence of galactose and situated upstream of the cloning site. Galactose-inducible promoters (GAL1, GAL7, and GAL10) have been extensively utilized for high level and regulated expression of proteins in yeast (Lue et al., 1987, *Mol. Cell. Biol.,* 7: 3446-3451 and Johnston M., 1987, *Microbiol. Rev.,* 51: 458-476). Transcription from the GAL promoters is activated by the GAL4 protein, which binds to the promoter region and activates transcription when galactose is present. In the absence of galactose, the antagonist GAL80 binds to GAL4 and prevents GAL4 from activating transcription. Addition of galactose prevents GAL80 from inhibiting activation by GAL4.

An expression vector may comprise a translation initiation or termination (e.g. stop) sequence oriented and operatively associated with the cDNA sequence encoding the mammalian desaturase (i.e. positioned upstream at the 5'-end or downstream at the 3'-end of the desaturase coding sequence, respectively). However, the translation initiation and termination codons may be already provided within the forward and reverse primer sequences, respectively, which are used to facilitate cloning of the mammalian desaturase genes into the pYES2 vector (see Example 1). Forward and reverse primers for cloning into pYES2/CT are designed to express a desaturase-V5/6×His tagged protein (see Example 1).

Host Systems

The invention provides a recombinant nucleic acid construct which contains a portion of a mammalian D5D gene including the amino acid coding region and which has a heterologous promoter capable of initiating transcription of a fatty acid desaturase gene. The amino acid coding region is derived from a human D5D gene. In particular, the invention provides a nucleic acid construct having a heterologous promoter region which is preferably induced, a nucleic acid sequence encoding a functional mammalian (e.g. human or rat) D5D and a termination region, whereby the promoter region is operably associated with the nucleic acid sequence so as to effectively control expression of the nucleic acid sequence. Alternatively, the recombinant nucleic acid construct may comprise a heterologous transcriptional termination region functional in a host system. The recombinant nucleic acid construct is cloned as part of an expression vector, which can then be inserted into a host system.

A polynucleotide encoding a mammalian (e.g. human or rat) D5D gene may be ligated to a heterologous sequence to encode a tagged protein. For screening of host systems that express D5D, it may be useful to encode a tagged desaturase protein that is recognized by a commercially available antibody. A tagged protein may also be engineered to contain a cleavage site located between a D5D coding sequence and the heterologous protein sequence, so that the fatty acid desaturase is cleaved and purified from the heterologous moiety.

Another aspect of the present invention is directed to a recombinant nucleic acid construct containing a control region of a mammalian D5D gene and a reporter gene. The control region is derived from a human D5D gene. The control region and the reporter sequence are operably linked so that the control region effectively initiates, terminates or regulates the transcription or translation of the reporter sequence. The recombinant nucleic acid construct is cloned as part of an expression vector, which is then inserted into a host system.

Accordingly, the host system is transformed/transfected by the nucleic acid construct containing the nucleic acid sequence of the D5D gene such that the promoter region and the termination region are operable and can, therefore, be used to achieve high level expression of a functionally active desaturase enzyme. A test component, which increases or decreases desaturase enzyme activity, is an enhancer or inhibitor, respectively. Consequently, defined test components can be used as a basis for the formulation or innovation of therapeutic agents to treat disease related to the level of active and regulated D5D enzyme in tissue.

The transformed/transfected host cell is identified by selection for a marker gene contained on the introduced vector construct The introduced marker gene, therefore, may confer antibiotic resistance, or encode an essential growth factor or enzyme, and permit growth on selective media when expressed in the transformed/transfected host. Typically, transformed/transfected hosts are selected due to their ability to grow on selective media Selective media may contain an antibiotic or lack an essential growth nutrient necessary for the growth of the untransformed/untransfected host. Transformation of *Escherichia coli* cells and yeast cells was determined through selection on ampicillin-containing medium and uracil-deficient medium, respectively, based on the selection marker genes (e.g. beta-lactamase and URA3) present in the pYES2 and pYES2/CT vectors.

A cell-free expression system is achieved by placing the nucleic acid construct, comprising the coding sequence for a functional mammalian desaturase described above, into an appropriate expression vector designed for in vitro use and carrying out in vitro transcription/translation in a cell lysate, such as mRNA-dependent rabbit reticulocyte lysate. If required, additional components may be incorporated into the system such as essential co-factors and amino acids. Microsomal systems have been used successfully for testing enzyme activity from a number of different sources such as animal organs including liver, brain, heart, etc. and microorganisms including yeast (de Antueno et al., 1994, *Lipids,* 29: 327-331; Todd et al., 1999, *Plant J.,* 17: 119-130; Nishi et al., 2000, *Biochim. Biophys. Acta,* 1490: 106-108).

A microsomal host system is achieved by transforming/transfecting the host system with the nucleic acid construct containing the coding sequence for a functional mammalian desaturase described above, and isolating microsomes (Ausubel et al., 1994-, *Current Protocols in Molecular Biology,* John Wiley & Sons, New York, N.Y.). In vitro transcription/translation is carried out by adding rabbit reticulocyte lysate and essential cofactors; labelled amino acids can be incorporated if desired. Such in vitro expression vectors may provide some or all of the expression signals necessary in the system used. These methods are well known in the art and the components of the system are commercially available. The reaction mixture is assayed directly for the polypeptide, for example by determining its specific enzymatic activity, or the synthesized polypeptide purified and then assayed for its specific enzymatic activity.

A cell system used in analyzing control regions which are involved in the regulation of the level of mammalian D5D gene expression is the mammalian cell lines ZR-75-1 (ATCC No. CRL-1500) or HepG2 (ATCC No. HB-8065).

Reporter genes which are widely utilized in such studies include, but are not limited to, enzymes such as luciferase, chloramphenicol acetyl transferase (CAT), beta-galactosidase, esterases, phosphatases, proteases and other proteins such as green fluorescence protein (GFP) and human growth hormone. In preferred embodiments, the reporter gene is either CAT or luciferase which will be detected through the level of specific enzymatic activity, which in turn correlates to the amount of enzyme that was made and hence, the level of expression of the reporter gene.

A reporter vector of the present invention, which includes essential elements for its operability in prokaryotic or eukaryotic cells, is pCAT-3-Basic (Promega Corp., WI.). The mammalian desaturase control region, derived from genomic DNA, is ligated by conventional methods in proper orientation (5' to 3') adjacent (5) to the start codon of the reporter gene with or without additional control elements. The region 3' to the coding sequence for the reporter gene contains a transcription termination and polyadenylation site, for example, the SV40 polyA site. The desaturase control region and reporter gene, which are operably linked in the reporter vector, are transformed into a cloning host, preferably E. coli. The host is cultured and the replicated vector recovered in order to prepare sufficient quantities of the recombinant construction for subsequent transfection into a second host, preferably the mammalian cell lines ZR-75-1 or HepG2.

Host Systems and Drug Screening

The invention includes methods for screening nucleotides, proteins, compounds or pharmacological agents, which enhance or inhibit D5D gene expression at the transcriptional level or modulate the D5D activity. To this end, cell-based, cell lysate and/or purified enzyme assays are used to detect these enhancing or inhibiting components.

D5D gene expression has been associated with diabetes and related disorders, arterial hypertension; hypercholesterolemia; atherosclerotic heart disease; chronic inflammatory disorders; autoimmune disorders; allergic eczema and other atopic disorders; inflammatory processes such as rheumatoid arthritis; diminished lymphocyte proliferation, T-cell-mediated cytotoxicity, natural killer cell activity, macrophage-mediated cytotoxicity, monocyte and neutrophil chemotaxis, major histocompatibility class II expression and antigen presentation, production of pro-inflammatory cytokines (interleukins 1 and 6, tumour necrosis factor) and adhesion molecule expression; eczema; psoriasis; acute respiratory distress syndrome (ARDS); articular cartilage degradation (ACD); and cancer.

A present inventors' human diabetic clinical trial has provided data indicating that AA and EPA were reduced in the plasma and red cell phospholipids of Type 1 diabetics. This study supports and expands a multi-center clinical trial sponsored by Scotia Pharmaceuticals in which enteral administration of n-6 PUFAs ameliorates neurophysiological parameters of mild diabetic neuropathy (Keen et al., 1993, *Diabetes Care,* 16: 8-15). Reduced levels of long chain n-6 fatty acids have been reported (Arisaka et al., 1986, *J. Paediatr. Gastroenterol Nutr.,* 5: 878-882; Tilvis R. S. and Miettinen T. A., 1985, *J. Clin. Endocrinol. Metab.,* 61: 741-745; and van Doormaal et al., 1988, *Diabetologia,* 31: 576-584). The level of DLL was not reduced in the Type 1 diabetic group, indicating that the reduction of AA may be due to reduced delta-5-desaturase activity.

In a present inventors' diabetic rat study, the plasma phospholipid AA content was reduced 31% and 27% in the 2 week and 7 week streptozotocin-induced diabetic rats, respectively. As in the human diabetic study, the DLL levels remained unchanged compared to controls, so the reduced levels of AA and EPA were consistent with a detected reduction in delta-5-desaturase activity. Reduced activity of the desaturase system in diabetes was first reported by Brenner et al., 1968, *Am. J. Physiol.,* 215: 63-70. Subsequently, this finding has been verified (Mimouni V. and Poisson J. P., 1992, *Biochinm. Biophys. Acta,* 1123: 296-302; Dang et al., 1989, *Lipids,* 24: 882-889; and Faas F. H. and Carter W. J., 1980, *Lipids,* 15: 953-961) and is considered to be a key factor in the development of secondary complications of diabetes. In the streptozotocin diabetic rat study, it was determined that the delta-5-desaturase activity in hepatic microsomes from diabetic rats was reduced by 37% compared to the control rats. These findings support the hypothesis that delta-5-desaturase is a potential drug target in diabetes and also a useful lipid metabolic compound for drug screening assays.

The present invention features a drug screening method for identifying nucleotides, proteins, compounds, and/or pharmacological agents which modulate or regulate the transcription of a mammalian D5D gene. This method includes (1) providing a novel nucleic acid construct having a control region of a mammalian desaturase gene and a heterologous nucleic acid sequence (e.g. a reporter gene), wherein the control region is operably associated with the nucleic acid sequence so that it effectively initiates, terminates or regulates the transcription of the nucleic acid sequence, all of which are introduced into a cell or cell lysate using an expression vector containing the novel nucleic acid construct, (2) contacting the cell or cell lysate with a test component, (3) determining whether the test component is capable of altering the level of transcription of the nucleic acid sequence, and (4) selecting those components which exhibit such activity. In this regard, the defined test components can be used as a basis for the formulation or innovation of therapeutic drugs to treat disease related to the level of D5D gene expression. Test components, which increase or decrease the level of transcription of the reporter sequence, are enhancers or inhibitors, respectively.

In particular, the present invention embodies a method for the identification of useful and functional portions of the D5D control region and various functional and regulatory elements within the control region, which are associated with the level of expression of the desaturase gene. Functional portions of the desaturase control region which result in altered levels of gene expression are determined through the manipulation (e.g. deletion, site-directed mutagenesis, etc.) of various segments of the region, as well as through the direct or indirect effect of modulators.

The host system for conducting the drug screening method can be eukaryotic cells, including fungal or mammalian cells. More specifically, an embodiment of the present invention relates to a drug screening assay using transformed yeast as whole cells, spheroplasts, cell homogenates, organelles (e.g. microsomes, etc.) or purified enzyme to identify candidate agents that modulate the enzymatic activity of a mammalian D5D. In an embodiment of the present invention the host yeast *Saccharomyces cerevisiae,* strain INVSc1 (Invitrogen, Calif.), is transformed with the yeast expression vectors, pYES2 or pYES2/ CT (Invitrogen), containing the mammalian D5D coding sequence. Yeast cells are selected for use in the present method because (1) they have not shown fatty acid delta-5-desaturase activity (Aki et al., 1999, *Biochem. Biophys. Res. Comma,* 255: 575-579), (2) their transcription and translation processes are similar, if not identical, to processes that occur in mammalian cells, and (3) they are often more amenable to genetic manipulation than mammalian cells, and they grow much more rapidly (Guthrie C. and Fink G., 1991, *Meth. Enzymol.,* 194). Thus, yeast cells provide an excellent model for eukaryotic gene expression and for studying the modulation of mammalian D5D activity.

When a host cell, such as a yeast cell, is transformed with a DNA construct according to the present invention, it is utilized in assays to identify test components that modulate desaturase activity. Test components that modulate D5D activity are identified by (1) contacting the transformed host cell with the test component for a fixed period of time, and (2) determining the level of lipid metabolite (i.e. the level of product produced from substrate) or associated cofactors within the treated cells. This level of metabolite in one cell can then be compared to the level of metabolite in the absence of the test component. The difference between the levels of metabolite, if any, indicates whether the test component of interest modulates D5D activity. Furthermore, the magnitude of the level of lipid metabolite generated between the treated and untreated cells provides a relative indication of the strength of that compound(s) as a modulator of desaturase activity. Rat liver microsomes are used in conjunction with the preferred host system to corroborate the strength of that compound(s) as a modulator of desaturase activity.

A drug screening assay is also carried out using mammalian cells as host systems to observe the regulation of D5D gene expression and identify test components that modulate the expression of a reporter gene driven by D5D gene control regions or regulatory elements. ZR-75-1 or HepG2 cell lines are preferably used as the host systems, which are transfected with the reporter vectors, pCAT-3-Basic (Promega) or pGL3-Basic (Promega) containing the mammalian D5D control sequence.

When a preferred host cell line, such as ZR-75-1, is transfected with a reporter DNA construct according to the present invention, it is utilized in assays to identify test components that modulate the level of gene transcription via functionally active regulatory elements/oligonucleotide sequences. Test components that alter the level of gene transcription can be identified by (1) contacting the transfected host cell with the test component for a fixed period of time, and (2) determining the level of gene expression (e.g. CAT activity) within the treated cells. This expression level is compared to that of the reporter gene in the absence of the compound(s). The difference between the levels of gene expression, if any, indicates whether the compound(s) of interest modifies the functionality of the DNA regulatory elements. Furthermore, the magnitude of the level of reporter product expressed between the treated and untreated cells provides a relative indication of the strength of that compound(s) as a modulator of the D5D gene transcription via transcriptional DNA regulatory elements.

In an embodiment, a high-throughput screening protocol is used to survey a large number of test compounds for their ability to modulate or regulate the transcription of a mammalian D5D gene through their effect on the desaturase control region. Accordingly, the design of the transcriptional system makes it possible to screen a large selection of components as potential therapeutic agents that alter D5D gene expression thereby increasing or decreasing tissue levels of a functional D5D enzyme, the physiological significance of which includes the normalization of lipid metabolites.

For the drug screening methods described herein, the host system may be a cell, tissue, organ, organism or any part thereof, which provides an environment or conditions that allow for, or enable, transcription and/or transcription followed by subsequent translation to yield a functional protein or polypeptide. Organisms would include animals such as mammals. In an embodiment of the invention, the drug screening methods are conducted in prokaryotic and eukaryotic cells. In embodiments of the invention, the eukaryotic cells include yeast cells and mammalian cells.

Potential antagonists include small organic molecules, peptides, polypeptides and antibodies that bind to a polynucleotide or polypeptide of the invention and thereby inhibit or extinguish its activity. Potential antagonists also may be small organic molecules, a peptide, a polypeptide such as a closely related protein or antibody that bind the same sites on a binding molecule, such as a binding molecule, without inducing delta-5-desaturase-induced activities, thereby preventing the action of delta-5-desaturase by interfering with substrate binding.

Potential antagonists include a small molecule, which bind to and occupy the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano et al., 1988, *EMBO J.*, 7: 3407-3412 for a description of these molecules). Selective modulators may include, for example, antibodies and other proteins or peptides which specifically bind to the delta-5-desaturase or delta-5-desaturase nucleic acid, oligonucleotides which specifically bind to delta-5-desaturase (see Patent Cooperation Treaty International Publication No. WO93/05182 published Mar. 18, 1993 which describes methods for selecting oligonucleotides which selectively bind to target biomolecules) or delta-5-desaturase nucleic acid (e.g. antisense oligonucleotides) and other non-peptide natural or synthetic compounds which specifically bind to the delta-5-desaturase or delta-5-desaturase nucleic acid.

Targets for the development of selective modulators include, for example: (1) the regions of the delta-5-desaturase which contact other proteins and/or localize the delta-5-desaturase within a cell and (2) the regions of the delta-5-desaturase which bind substrate.

Antibodies

With respect to protein-based testing, antibodies can be generated to the delta-5-desaturase gene product using standard immunological techniques, fusion proteins or synthetic peptides as described herein. Monoclonal antibodies can also be produced using now conventional techniques such as those described in Waldmann T. A., 1991, *Science*, 252: 1657-1662 and Harlow E. and Lane D. (eds.), 1988, *Antibodies: A Laboratory Manual*, Cold Harbour Press, Cold Harbour, N.Y. It will also be appreciated that antibody fragments, i.e. Fab' fragments, can be similarly employed. Immunoassays, for example ELISAs, in which the test sample is contacted with antibody and binding to the gene product detected, can provide a quick and efficient method of determining the presence and quantity of the fatty acid regulated gene product.

Thus, the present invention also provides polyclonal and/or monoclonal antibodies and fragments thereof, and immunologic binding equivalents thereof, against human and mammalian (e.g. rat) delta-5-desaturase, which are capable of specifically binding to the subject polypeptides and fragments thereof or to polynucleotide sequences from the subject polynucleotide region, particularly from the subject polypeptide locus or a portion thereof. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the subject polypeptide or fragment. Monoclonal antibodies may be made by injecting mice with the protein polypeptides, fusion proteins or fragments thereof. Monoclonal antibodies will be screened by ELISA and tested for specific immunoreactivity with subject polypeptide or fragments thereof (Harlow E. and Lane D. (eds.), 1988, *Antibodies: A Laboratory Manual*, Cold Harbour Press, Cold Harbour, N.Y.). These antibodies will be useful in assays as well as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art. For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical sites for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art (Harlow E. and Lane D. (eds.), 1988, *Antibodies: A Laboratory Manual*, Cold Harbour Press, Cold Harbour, N.Y., or Goding J. W., 1996, *Monoclonal Antibodies: Principles and Practice: Production and Application of Monoclonal Antibodies in Cell Biology, Biochemistry and Immunology*, 3$^{rd}$ edition, Academic Press, New York).

Monoclonal antibodies with affinities of $10^{-8}$ M$^{-1}$ or preferably $10^{-9}$ to $10^{-10}$ M$^{-1}$ or stronger will typically be made by standard procedures as described, e.g., in Harlow E. and Lane D. (eds.), 1988, *Antibodies: A Laboratory Manual*, Cold Harbour Press, Cold Harbour, N.Y. or Goding J. W., 1996, *Monoclonal Antibodies: Principles and Practice: Production and Application of Monoclonal Antibodies in Cell Biology, Biochemistry and Immunology*, 3$^{rd}$ edition, Academic Press, New York. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors (Huse et al., 1989, *Science*, 246: 1275-1281). The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionucleotides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced (see U.S. Pat. No. 4,816,567).

Drug Design

Modulation of delta-5-desaturase gene function can be accomplished by the use of therapeutic agents or drugs which can be designed to interact with different aspects of delta-5-desaturase control region structure or function. For example, a drug or antibody can bind to a structural fold of the control region to correct a defective structure. Alternatively, a drug might bind to a specific functional residue and increase its affinity for a substrate or cofactor. Efficacy of a drug or agent can be identified by a screening program in which modulation is monitored in vitro in cell systems in which a delta-5-desaturase gene protein is expressed. Alternatively, drugs can be designed to modulate delta-5-desaturase gene activity from knowledge of the structure and function correlations and from knowledge of the specific defect in the various NF1 mutant proteins (see Copsey D. N. and Delnatte S. Y. J., 1988, *Genetically Engineered Human Therapeutic Drugs*, Stockton Press, New York).

Gene Therapy

A variety of gene therapy approaches may be used in accordance with the invention to modulate expression of delta-5-desaturase in vivo. For example, antisense DNA molecules may be engineered and used to block delta-5-desaturase DNA in vivo. In another alternative, oligonucleotides designed to hybridize to the 5' region of the delta-5-desaturase control sequence and form triple helix structures may be used to block or reduce transcription of the delta-5-desaturase. In yet another alternative, nucleic acid encoding the full length wild-type delta-5-desaturase control region may be introduced in vivo into cells which otherwise would be unable to produce the wild-type delta-5-desaturase product in sufficient quantities or at all.

For example, in conventional replacement therapy, gene product or its functional equivalent is provided to the patient in therapeutically effective amounts. Delta-5-desaturase protein can be purified using conventional techniques such as those described in Deutcher, M. (editor), 1990, *Guide to Protein Purification. Meth. Enzymol.*: 182. Sufficient amounts of gene product or protein for treatment can be obtained, for example, through cultured cell systems or synthetic manufacture. Drug therapies which stimulate or replace the gene product can also be employed. Delivery vehicles and schemes can be specifically tailored to the particular protein or drug being administered.

Gene therapy using recombinant technology to deliver the gene into the patients cells or vectors, which will supply the patient with gene product in vivo, is also contemplated as within the scope of the present invention. Retroviruses have been considered a preferred vector for experiments in somatic gene therapy, with a high efficiency of infection and stable integration and expression (Orkin, et al., 1988, *Prog. Med. Genet.* 7: 130-142). For example, delta-5-desaturase cDNA can be cloned into a retroviral vector and driven from either its endogenous promoter of from the retroviral LTR (long terminal repeat). Other delivery systems which can be utilized include adeno-associated virus (AAV) (McLaughlin et al., 1988, *J. Virol.* 62: 1963-1973), vaccinia virus (Moss et al., 1987, *Annu. Rev. Immunol.* 5: 305-324), bovine papilloma virus (Rasmussen, et al.,1987, *Meth. Enzymol.* 139: 642-654), or member of the herpesvirus group such as Epstein-Barr virus (Margolskee, et al., 1988, *Mol. Cell. Biol.* 8: 2837-2847.

In another embodiment, the antisense, ribozyme and triple helix nucleotides are designed to inhibit the translation or transcription of delta-5-desaturase. To accomplish this, the oligonucleotides used should be designed on the basis of relevant sequences unique to delta-5-desaturase control region.

For example, and not by way of limitation, the oligonucleotides should not fall within those region where the nucleotide sequence of a subject polynucleotide is most homologous to that of other fatty acid enzyme polynucleotides, herein referred to as "unique regions".

In the case of antisense molecules, it is preferred that the sequence be chosen from the unique regions. It is also preferred that the sequence be at least 18 nucleotides in length in order to achieve sufficiently strong annealing to the target mRNA sequence to prevent translation of the sequence. Izant J. G. and Weintraub H., 1984, Cell, 36: 1007-1015; Rosenberg et al., 1985, Nature, 313: 703-706.

In the case of the "hammerhead" type of ribozymes, it is also preferred that the target sequences of the ribozymes be chosen from the unique regions. Ribozymes are RNA molecules which possess highly specific endoribonuclease activity. Hammerhead ribozymes comprise a hybridizing region which is complementary in nucleotide sequence to at least part of the target RNA, and a catalytic region which is adapted to cleave the target RNA. The hybridizing region contains nine or more nucleotides. Therefore, the hammerhead ribozymes of the present invention have a hybridizing region which is complementary to the sequences listed above and is at least nine nucleotides in length. The construction and production of such ribozymes is well known in the art and is described more fully in Haseloff J. and Gerlach W. L., 1988, Nature, 334: 585-591.

The ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug et al., 1984, Science, 224: 574-578; Zaug A. J. and Cech T. R., 1986, Science, 231: 470-475; Zaug, et al., 1986, Nature, 324: 429-433; published International patent application No. WO 88/04300 by University Patents Inc. June, 1988; Been M. D. and Cech T. R., 1986, Cell, 47: 207-216). The Cech endoribonucleases have an eight base pair active site which hybridizes to a target RNA sequence whereafter cleavage of the target RNA takes place. The invention encompasses those Cech-type ribozymes which target eight base-pair active site sequences that are present in a subject polynucleotide but not other polynucleotides for fatty acid enzymes.

The compounds can be administered by a variety of methods which are known in the art including, but not limited to the use of liposomes as a delivery vehicle. Naked DNA or RNA molecules may also be used where they are in a form which is resistant to degradation such as by modification of the ends, by the formation of circular molecules, or by the use of alternate bonds including phosphothionate and thiophosphoryl modified bonds. In addition, the delivery of nucleic acid may be by facilitated transport where the nucleic acid molecules are conjugated to poly-lysine or transferrin. Nucleic acid may also be transported into cells by any of the various viral carriers, including but not limited to, retrovirus, vaccinia, AAV, and adenovirus.

Alternatively, a recombinant nucleic acid molecule which encodes, or is, such antisense, ribozyme, triple helix, or subject polynucleotide molecule can be constructed. This nucleic acid molecule may be either RNA or DNA. If the nucleic acid encodes an RNA, it is preferred that the sequence be operatively attached to a regulatory element so that sufficient copies of the desired RNA product are produced. The regulatory element may permit either constitutive or regulated transcription of the sequence. In vivo, that is, within the cells or cells of an organism, a transfer vector such as a bacterial plasmid or viral RNA or DNA, encoding one or more of the RNAs, may be transfected into cells e.g. (Llewellyn et al., 1987, J. Mol. Biol., 195: 115-123; Hanahan et al., 1983, J. Mol. Biol., 166: 557-580). Once inside the cell, the transfer vector may replicate, and be transcribed by cellular polymerases to produce the RNA or it may be integrated into the genome of the host cell. Alternatively, a transfer vector containing sequences encoding one or more of the RNAs may be transfected into cells or introduced into cells by way of micromanipulation techniques such as microinjection, such that the transfer vector or a part thereof becomes integrated into the genome of the host cell.

Composition, Formulation, and Administration of Pharmaceutical Compositions

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by belus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. Naturally, the proportions of a co-solvent system may be varied considerably without destroying its solubility and toxicity characteristics. Furthermore, the identity of the co-solvent components may be varied.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semi-permeable matrices of solid hydrophobic polymers containing the therapeutic agent. Various of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

Suitable routes of administration may, for example, include oral, rectal, transmucosal, transdermal, or intestinal administration; parenteral delivery, including intramuscular, subcutaneous, intramedullary injections, as well as intrathecal, direct intraventricular, intravenous, intraperitoneal, intranasal, or intraocular injections.

Alternately, one may administer the compound in a local rather than systemic manner, for example, via injection of the compound directly into an affected area, often in a depot or sustained release formulation.

Furthermore, one may administer the drug in a targeted drug delivery system, for example, in a liposome coated with an antibody specific for affected cells. The liposomes will be targeted to and taken up selectively by the cells.

The pharmaceutical compositions generally are administered in an amount effective for treatment or prophylaxis of a specific indication or indications. It is appreciated that optimum dosage will be determined by standard methods for each treatment modality and indication, taking into account the indication, its severity, route of administration, complicating conditions and the like. In therapy or as a prophylactic, the active agent may be administered to an individual as an injectable composition, for example as a sterile aqueous dispersion, preferably isotonic. A therapeutically effective dose further refers to that amount of the compound sufficient to result in amelioration of symptoms associated with such disorders. Techniques for formulation and administration of the compounds of the instant application may be found in Mack E. W., 1990, *Remington's Pharmaceutical Sciences*, Mack Publishing Company, Easton, Pa., 13$^{th}$ edition. For administration to mammals, and particularly humans, it is expected that the daily dosage level of the active agent will be from 0.001 mg/kg to 10 mg/kg, typically around 0.01 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

Thus, the present invention provides a method for screening and selecting compounds, which promote lipid metabolism disorders, and a method for screening and selecting compounds, which treat or inhibit lipid metabolism disorders, as well as diabetic neuropathy. The selected antagonists and agonists may be administered, for instance, to inhibit progressive and acute disorders, such as arterial hypertension, hypercholesterolemia, atherosclerotic heart disease, chronic inflammatory and autoimmune disorders, allergic eczema and other atopic disorders, and cancers, including human pancreatic cancer.

Antagonists, agonists and other compounds of the present invention may be employed alone or in conjunction with other compounds, such as therapeutic compounds. The pharmaceutical compositions may be administered in any effective, convenient manner including, for instance, administration by direct microinjection into the affected area or by intravenous or other routes. These compositions of the present invention may be employed in combination with a non-sterile or sterile carrier or carriers for use with cells, tissues or organisms, such as a pharmaceutical carrier suitable for administration to a subject. Such compositions comprise, for instance, a medium additive or a therapeutically effective amount of antagonists or agonists of the invention and a pharmaceutically acceptable carrier or excipient. Such carriers may include, but are not limited to, saline, buffered saline, dextrose, water, glycerol, ethanol and combinations thereof. The formulation is prepared to suit the mode of administration.

The invention further provides diagnostic and pharmaceutical packs and kits comprising one or more containers filled with one or more of the ingredients of the aforementioned compositions of the invention. Associated with such container(s) can be a notice in the form prescribed by a governmental agency regulating the manufacture, use or sale of pharmaceuticals or biological products, reflecting approval by the agency of the manufacture, use or sale of the product for human administration.

The pharmaceutical compositions generally are administered in an amount effective for treatment or prophylaxis of a specific indication or indications. It is appreciated that optimum dosage will be determined by standard methods for each treatment modality and indication, taking into account the indication, its severity, route of administration, complicating conditions and the like. In therapy or as a prophylactic, the active agent may be administered to an individual as an injectable composition, for example as a sterile aqueous dispersion, preferably isotonic. For administration to mammals, and particularly humans, it is expected that the daily dosage level of the active agent will be from 0.001 mg/kg to 10 mg/kg, typically around 0.01 mg/kg. The physician in any event will determine the actual dosage that will be most suitable for an individual and will vary with the age, weight and response of the particular individual. The above dosages are exemplary of the average case. There can, of course, be individual instances where higher or lower dosage ranges are merited, and such are within the scope of this invention.

It is understood that the present invention is not limited to the particular methodology, protocols, cell lines, vectors, and reagents described herein. Generally, the laboratory procedures in cell culture and molecular genetics described below are those well known and commonly employed in the art. Standard techniques are used for recombinant nucleic acid methods, polynucleotide synthesis, microbial culture, transformation, transfection, etc. Generally, enzymatic reactions and purification steps are performed according to the manufacturer's specifications. Although any methods and materials similar or equivalent to those described herein can be used in the practice or testing of the present invention, the selected methods, devices, and materials are described below.

To facilitate a complete understanding of the invention, the terms defined below have the following meaning:

Agonist refers to any molecule or pharmaceutical agent, such as a drug or hormone, which enhances the activity of another molecule.

Antagonist is any molecule or pharmaceutical agent, such as a drug or hormone, which inhibits or extinguishes the activity of another molecule.

Control region refers to a nucleic acid sequence comprising a gene or a plurality of genes or fragments thereof capable of, or required for, assisting or impeding initiation, termination, or otherwise regulating the transcription of a gene, wherein the control region may include a promoter, enhancer, silencer and/or any other regulatory element. A control region can also include a nucleic acid sequence that may or may not be independently or exclusively sufficient to initiate, terminate, or otherwise regulate transcription, however, is capable of effecting such regulation in association with other nucleic acid sequences.

Desaturase refers to a fatty acid desaturase, which is an enzyme capable of generating a double bond in the hydrocarbon region of a fatty acid molecule.

Fatty Acids are a class of compounds comprising a long saturated or mono or polyunsaturated hydrocarbon chain and a terminal carboxyl group.

Fatty Acid Delta-5-Desaturase (D5D) is an enzyme capable of generating a double bond between carbons 5 and 6 from the carboxyl group in a fatty acid molecule.

Fatty Acid Delta-6-Desaturase is an enzyme capable of generating a double bond between carbons 6 and 7 from the carboxyl group in a fatty acid molecule.

Functional Enzyme, as used herein, refers to a biologically active or non-active protein with a known enzymatic activity.

Enhancer is a nucleic acid sequence comprising a DNA regulatory element that enhances or increases transcription when bound by a specific transcription factor or factors. An enhancer is generally, but not exclusively, located outside the proximal promoter region of a target gene and may be located several kilobases (kb) or more from the transcription start site of the target gene. Moreover, an enhancer may function in either orientation and in any location (upstream or downstream relative to the promoter) to effect and generate increased levels of gene expression when bound by specific factors. In addition, according to the present invention, an enhancer also refers to a compound (i.e. test component) that increases or promotes the enzymatic activity of fatty acid desaturase, and/or increases or promotes the transcription of the gene encoding a fatty acid desaturase.

Gene refers to a nucleic acid molecule or a portion thereof, the sequence of which includes information required for the normal regulated production of a particular protein or polypeptide chain. A "heterologous" region of a nucleic acid construct (i.e. a heterologous gene) is an identifiable segment of DNA within a larger nucleic acid construct that is not found in association with the other genetic components of the construct in nature. Thus, when the heterologous gene encodes a mammalian fatty acid desaturase gene, the gene will usually be flanked by a promoter that does not flank the structural genomic DNA in the genome of the source organism.

Host system may comprise a cell, tissue, organ, organism or any part thereof, which provides an environment or conditions that allow for, or enable, transcription and/or transcription by an exogenous polynucleotide sequence followed by subsequent translation to yield a functional protein or polypeptide.

Inhibitor refers to a substance or compound (i.e. test component) that decreases or prevents the enzymatic activity of fatty acid desaturase or decreases or suppresses the transcription of the gene encoding a fatty acid desaturase.

Identity, similarity or homologous, refer to relationships between two or more polynucleotide sequences, as determined by comparing the sequences. In the art, identity also means the degree of sequence relatedness between polynucleotide sequences, as the case may be, as determined by the match between strings of such sequences. Both identity and similarity can be readily calculated (Lesk A. M., ed., 1988, *Computational Molecular Biology*, Oxford University Press, New York; Smith D. W., ed., 1993, *Biocomputing: Infomatics and Genome Project*, Academic Press, New York; Griffin A. M. and Griffin H. G., eds., 1994, *Computer Analysis of Sequence Data, Part* 1, Humana Press, New Jersey; von Heijne G., 1987, *Sequence Analysis in Molecular Biology*, Academic Press, New York and Gribskov M. and Devereux J., eds., 1991, *Sequence Analysis Primer*, M Stockton Press, New York). While there exist a number of methods to measure identity and similarity between two polynucleotide sequences, both terms are well known to skilled artisans (von Heijne G., 1987, *Sequence Analysis in Molecular Biology*, Academic Press, New York; Gribskov M. and Devereux J., eds., 1991, *Sequence Analysis Primer*, M Stockton Press, New York; Carillo H. and Lipman D., 1988, *SIAM J. Applied Math.,* 48: 1073). Methods commonly employed to determine identity or similarity between sequences include, but are not limited to those disclosed in Carillo H. and Lipman D., 1988, *SIAM J. Applied Math.,* 48: 1073. Methods to determine identity and similarity are codified in computer programs. Computer program methods to determine identity and similarity between two sequences include, but are not limited to, GCG program package (Devereux et al., 1984, *Nucl. Acid Res.,* 12(1): 387-395), BLASTP, BLASTN, and FASTA (Altschul et al., 1990, *J. Molec. Biol.,* 215: 403-410).

Isolated means altered "by the hand of man" from its natural state; i.e., that, if it occurs in nature, it has been changed or removed from its original environment, or both. For example, a naturally occurring polynucleotide naturally present in a living organism in its natural state is not "isolated," but the same polynucleotide separated from coexisting materials of its natural state is "isolated", as the term is employed herein. As part of or following isolation, such polynucleotides can be joined to other polynucleotides, such as DNA, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNA still would be isolated, as the term is used herein, because they would not be in their naturally occurring form or environment. Similarly, the polynucleotides may occur in a composition, such as medium formulations, solutions for introduction of polynucleotides, for example, into cells, compositions or solutions for chemical or enzymatic reactions, for instance, which are not naturally occurring compositions, and therein remain isolated polynucleotides within the meaning of that term as it is employed herein.

Nucleic acid construct refers to any genetic element, including, but not limited to, plasmids and vectors, that incorporate polynucleotide sequences. For example, a nucleic acid construct may be a vector comprising a promoter or control region that is operably linked to a heterologous gene.

Operably linked as used herein indicates the association of a promoter or control region of a nucleic acid construct with a heterologous gene such that the presence or modulation of the promoter or control region influences the transcription of the heterologous gene, including genes for reporter sequences. Operably linked sequences may also include two segments that are transcribed onto the same RNA transcript. Thus, two sequences, such as a promoter and a reporter sequence are operably linked if transcription commencing in the promoter will produce an RNA transcript of the reporter sequence.

Promoter refers to a nucleic acid sequence comprising a DNA regulatory element capable of binding RNA polymerase directly or indirectly to initiate transcription of a downstream (3' direction) gene. In accordance with the present invention, a promoter of a nucleic acid construct that includes a nucleotide sequence, wherein the nucleotide sequence may be linked to a heterologous gene such that the induction of the promoter influences the transcription of the heterologous gene.

Recombinant refers to recombined or new combinations of nucleic acid sequences, genes, or fragments thereof that are produced by recombinant DNA techniques and are distinct from a naturally occurring nucleic acid sequence Regulatory element refers to a deoxyribonucleotide sequence comprising the whole; or a portion of, a nucleic acid sequence to which an activated transcriptional regulatory protein, or a complex comprising one or more activated transcriptional regulatory proteins, binds so as to transcriptionally modulate the expression of an associated gene or genes, including heterologous genes.

Reporter gene is a nucleic acid sequence that encodes a polypeptide or protein that is not otherwise produced by the host cell or host system, or which is produced in minimal or negligible amounts in the host cell or host system, and which is detectable by various known methods such that the reporter gene product may be quantitatively assayed to analyze the level of transcriptional activity in a host cell or host system. Examples include genes for luciferase, chloramphenicol acetyl transferase (CAT), beta-galactosidase, secreted placental alkaline phosphatase and other secreted enzymes.

Silencer refers to a nucleic acid sequence or segment of a DNA control region such that the presence of the silencer sequence in the region of a target gene suppresses the transcription of the target gene at the promoter through its actions as a discrete DNA segment or through the actions of trans-acting factors that bind to these genetic elements and consequently effect a negative control on the expression of a target gene.

Stringent hybridization conditions are those which are stringent enough to provide specificity, reduce the number of mismatches and yet are sufficiently flexible to allow formation of stable hybrids at an acceptable rate. Such conditions are known to those skilled in the art (Sambrook et al., 1989, *Molecular Cloning, 2nd Edition*, Cold Spring Harbor Laboratory Press, Cold Spring Harbour, N.Y.). By way of example only, stringent hybridization with short nucleotides may be carried out at 5-10° C. below the T$_M$ using high concentrations of probe such as 0.01-1.0 pmole/ml. Preferably, the term "stringent conditions" means hybridization will occur only if there is at least 95% and preferably at least 97% identity between the sequences.

Tag refers to a specific short amino acid sequence or a oligonucleotide sequence, wherein said amino acid or nucleic acid sequence may comprise or encode, for example, a V5 epitope recognizable by a commercially available antibody or a string of six histidine residues. In practice, a tag facilitates the subsequent identification and purification of a tagged protein.

Tagged protein as used herein refers to a protein comprising a linked tag sequence. In accordance with the present invention, a tagged protein refers to a mammalian fatty acid desaturase polypeptide linked to a V5 epitope and six histidine residues at the carboxyl terminus of the desaturase amino acid sequence.

Test components as used herein encompass small molecules (e.g. small organic molecules), pharmacological compounds or agents, peptides, proteins, antibodies or antibody fragments, and nucleic acid sequences, including DNA and RNA sequences.

Transcriptionally modulate the expression of an associated gene or genes means to change the rate of transcription of such gene or genes.

Transfection refers to a process whereby exogenous or heterologous DNA (i.e. a nucleic acid construct) is introduced into a recipient eukaryotic host cell. Therefore, in eukaryotic cells, the acquisition of exogenous DNA into a host cell is referred to as transfection. It should be noted that, eukaryotic transfection is analogous to bacterial transformation, whereby bacterial cells acquire exogenous or heterologous DNA. In prokaryotes and eukaryotes (for example, yeast and mammalian cells) introduced DNA may be maintained on an episomal element such as a plasmid or integrated into the host genome. With respect to eukaryotic cells, a stably transfected cell is one in which the introduced DNA has become integrated into a chromosome so that it is inherited by daughter cells through chromosome replication. This stability is demonstrated by the ability of the eukaryotic cell to establish cell lines or clones comprised of a population of daughter cells containing the introduced DNA.

Transfection/transformation as used herein refers to a process whereby exogenous or heterologous DNA (e.g. a nucleic acid construct) has been introduced into a eukaryotic or prokaryotic host cell or into a host system.

Transformation refers to a process whereby exogenous or heterologous DNA (i.e. a nucleic acid construct) is introduced into a recipient prokaryotic host cell. Therefore, in prokaryotic cells, the acquisition of exogenous DNA into a host cell is referred to as transformation. It should be noted that bacterial transformation is analogous to eukaryotic transfection. Moreover, it should also be noted that transformation in eukaryotes refers to the conversion or transformation of eukaryotic cells to a state of unrestrained growth in culture, resembling a tumorigenic condition. In prokaryotes and eukaryotes (for example, yeast and mammalian cells) introduced DNA may be maintained on an episomal element such as a plasmid or integrated into the host genome. With respect to prokaryotic cells, a stably transformed bacterial cell is one in which the introduced DNA has become integrated into a chromosome so that it is inherited by daughter cells through chromosome replication. This stability is demonstrated by the ability of the prokaryotic cell to establish cell lines or clones comprised of a population of daughter cells containing the introduced DNA.

The terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

The present invention is further described and will be better understood by referring to the working examples set forth below. These non-limiting examples are to be considered illustrative only of the principles of the invention. Since numerous modifications and changes will readily occur to those skilled in the art, it is not desired to limit the invention to the exact construction and operation shown and described. Accordingly, all suitable modifications and equivalents may be used and will fall within the scope of the invention and the appended claims.

EXAMPLES

Example 1

Cloning of Rat and Human Desaturase Genes

RNA Extraction: Total RNA was extracted from rat liver or the human cell line Chang (ATCC No. CCL-13), using TRIzol Reagent solution (Gibco BRL) as described by the manufacturer.

Reverse Transcription: About 1 µg of each RNA sample was reverse-transcribed in 3 MM MgCl$_2$, 75 mM KCl, 50 mM Tris-HCl (pH 8.3), 2 ng/µl of random primers (Perkin-Elmer), 1.0 mM each dNTP, 2.0 U/µl of RNase inhibitor (Perkin-Elmer) and 10 U/µl of MuLV reverse transcriptase (Perkin-Elmer). The reactions were carried out at 42° C. for 30 min in a final volume of 20 µl. The enzyme was then inactivated at 94° C. for 5 min.

Amplification of Desaturase Genes by PCR and Cloning in a Yeast Vector: Aliquots (5 µl) of the reverse transcription reactions were amplified by polymerase chain reaction (PCR), using primers designed to generate cDNA corresponding to the coding sequence for the human desaturase gene.

The hD5D gene was amplified in a two step process with two sets of primers for cloning in the pYES2 and pYES2/CT vectors (Invitrogen). The initial forward and reverse primers for the cloning of the hD5D gene into the pYES2 vector were 5'-CACGAC GAATTCCGTCGCCAGGCCAGCTATGG-3' (SEQ ID NO. 5) and 5'-CACTAT CTCGAGCTGGGCAGGGTGGCTGTTGT-3', (SEQ ID NO. 6) respectively. The translation initiation and termination codons (or a part thereof) are indicated by boldface type. The PCR product contained single EcoRI and XhoI sites (underlined) and was cloned into the pYES2 vector at these sites. This construct was named pYh5006.1.

The forward and reverse primers used to amplify the hD5D gene from the vector construct described above (pYh5006.1) were 5'-CACGG AAGCTTAAAAATGGCCCCGACCCGG-3' (SEQ ID NO.

Figure 6:
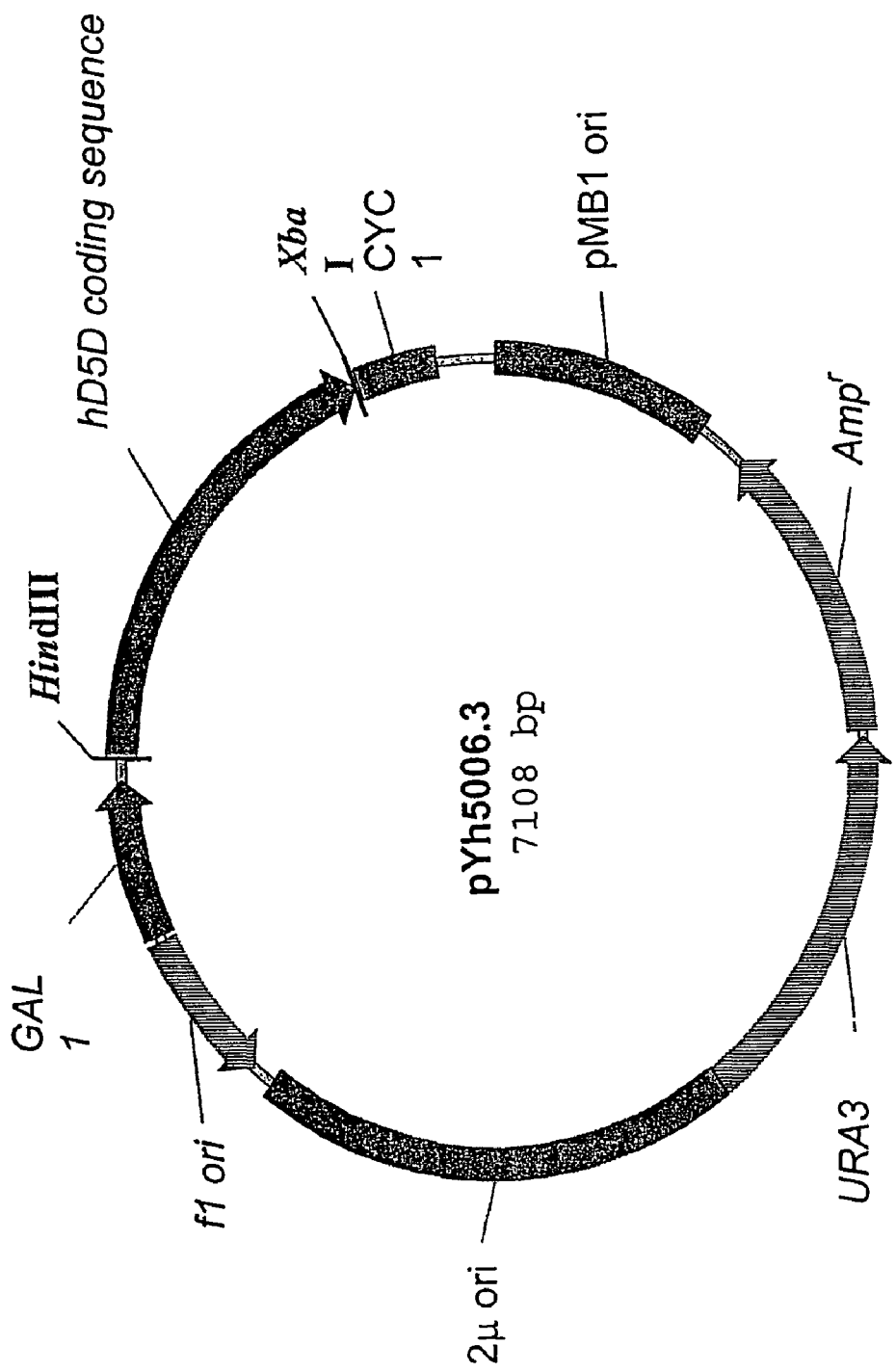
FIG. 6 is a schematic representation of plasmid pYh5006.3 (7108 bp). The human delta-5-desaturase coding sequence is shown between restriction sites for HindIII and XbaI.

7) and 5'-CACGCG TCTAGATTATTGGTGAAGATAGGCATCTAGCCAGC GCT-3' (SEQ ID NO. 8), respectively. The translation initiation and termination codons are shown in boldface type. This PCR product contained single HindIII and XbaI restriction sites (underlined) and was cloned in the pYES2 vector at these sites. The reverse primer for cloning the hD5D gene from pYh5006.1 into the pYES2/CT vector (Invitrogen), which contains a C-terminal tag for protein detection and purification, was 5'-CACGCG TCTAGATTGGTGAAGATAGGCATCTAGCCAGAGC TG-3' (SEQ ID NO. 9); the forward primer was the same as that used for the pYES2 construction. The reverse primer does not have a stop codon, therefore, placing the gene in frame with the C-terminal tag. The pYES2/CT and pYES2 constructs containing the hD5D gene were named pTh5009.1 and pYh5006.3, respectively (FIGS. 5 and 6 respectively).

Figure 7:
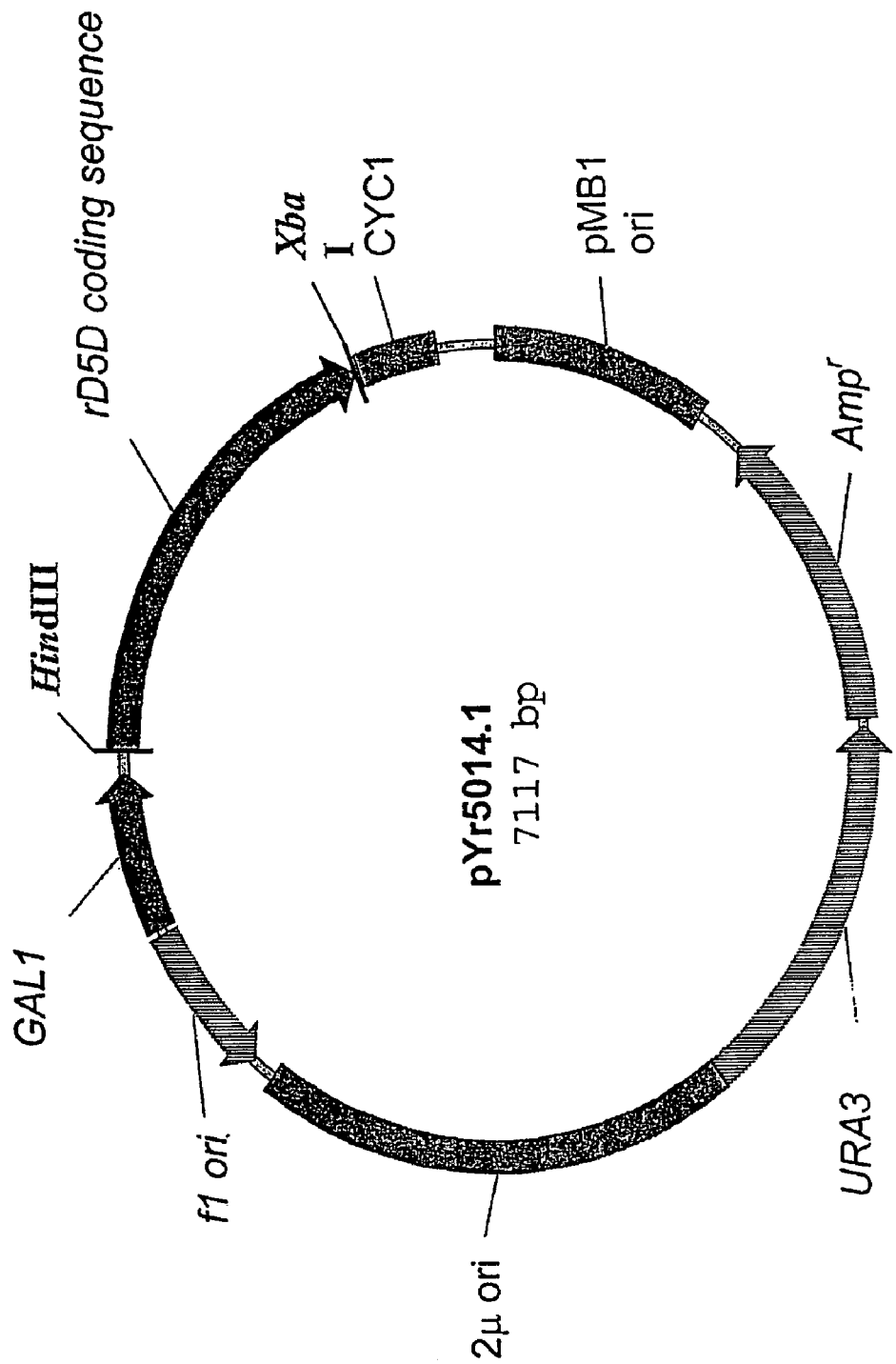
FIG. 7 is a schematic representation of plasmid pYr5014.1 (7117 bp). The rat delta-5-desaturase coding sequence is shown between restriction sites for HindIII and XbaI.

The forward and reverse primers for the rD5D were 5'-CACGCG AAGCTTAAAAATGGCCCCCGACCCGG-3' (SEQ ID NO. 10) and 5'-CACGCG TCTAGATTATTGGTGAAGATAGGCATCTAGCCAGC GCT-3' (SEQ ID NO. 11), respectively, for cloning in the pYES2 vector. Although these primers were designed for the hD5D gene, the rD5D gene was amplified from rat liver cDNA. The PCR product contained single HindIII and XbaI sites (underlined) adjacent to the translation initiation and stop codons, respectively (indicated by boldface type). The rD5D gene construct in the pYES2 vector was named pYr5014.1 (FIG. 7).

PCR was carried out using Advantage-HF polymerase (Clontech) according to the manufacturer's instructions. The PCR products were gel-purified using QIAquick gel extraction kit (Qiagen, Germany).

The purified PCR products and the yeast expression vectors pYES2 and pYES2/CT were digested with specific restriction enzymes according to the restriction sites generated during amplification and purified. The digested vector and PCR products were ligated and transformed into competent *E. coli*, strain INVαF' (for hD5D) or strain TOP10 (for rD5D) (Invitrogen), and selected on LB-agar plates containing ampicillin. Selected colonies were amplified and plasmid DNA was isolated using QIAprep spin miniprep kit (Qiagen). All plasmid constructions were confirmed by DNA sequence analysis. Transformation of *Saccharomyces cerevisiae*, strain INVSc1 (Invitrogen), with the plasmids was done using the lithium acetate method (Invitrogen) and recombinant yeast cells were selected on uracil-deficient synthetic minimal medium (SC-U).

Yeast strain construction: The genotype of INVSc1 is (Mata/Matα his3Δ1/his3Δ1 leu2/leu2 trp1-289/trp1-289 ura3-52/ura3-52). After having transformed *Saccharomyces cerevisiae* with desaturase gene constructs as previously described, the resulting strains were isogenic to INVSc1 except for the presence of desaturase constructs.

Example 2

Cloning and Identification of the Human Desaturase Control Region

The hD5D control region was cloned from human leukocyte genomic DNA by two rounds of PCR reactions. The first PCR reaction used the following primers: a reverse primer starting at position +127 of the hD5D coding sequence (5'-CACCTTACGGTCGATCACTA-3'; SEQ ID NO. 12) and a forward primer starting at position −1357 upstream from the translation initiation codon, ATG (5'-CTCAGTGCTTGGGACAGTTA-3'; SEQ ID NO.13).

The PCR amplification was conducted in a Perkin-Elmer GeneAMP PCR system 9700 instrument in a 50 μl reaction volume containing: 0.5 μg of genomic DNA, 0.4 μM of each primer, 1×dNTP mix (Clontech, Calif.), 1×PCR reaction buffer (Clontech) and 1× Advantage-polymerase mix (Clontech).

The conditions for the PCR reaction were:
7 cycles at 94° C. for 2 seconds, 72° C. for 3 minutes
32 cycles at 94° C. for 2 seconds, 67° C. for 3 minutes
67° C. for 4 minutes The PCR products were gel-purified using QIAquick gel extraction kit (Qiagen) and inserted into the TA cloning vector, pCRII (Invitrogen). The resulting plasmid called pCh4012.1 was used as template in a second PCR reaction aimed at cloning the hD5D control region without part of the coding sequence.

Figure 8:
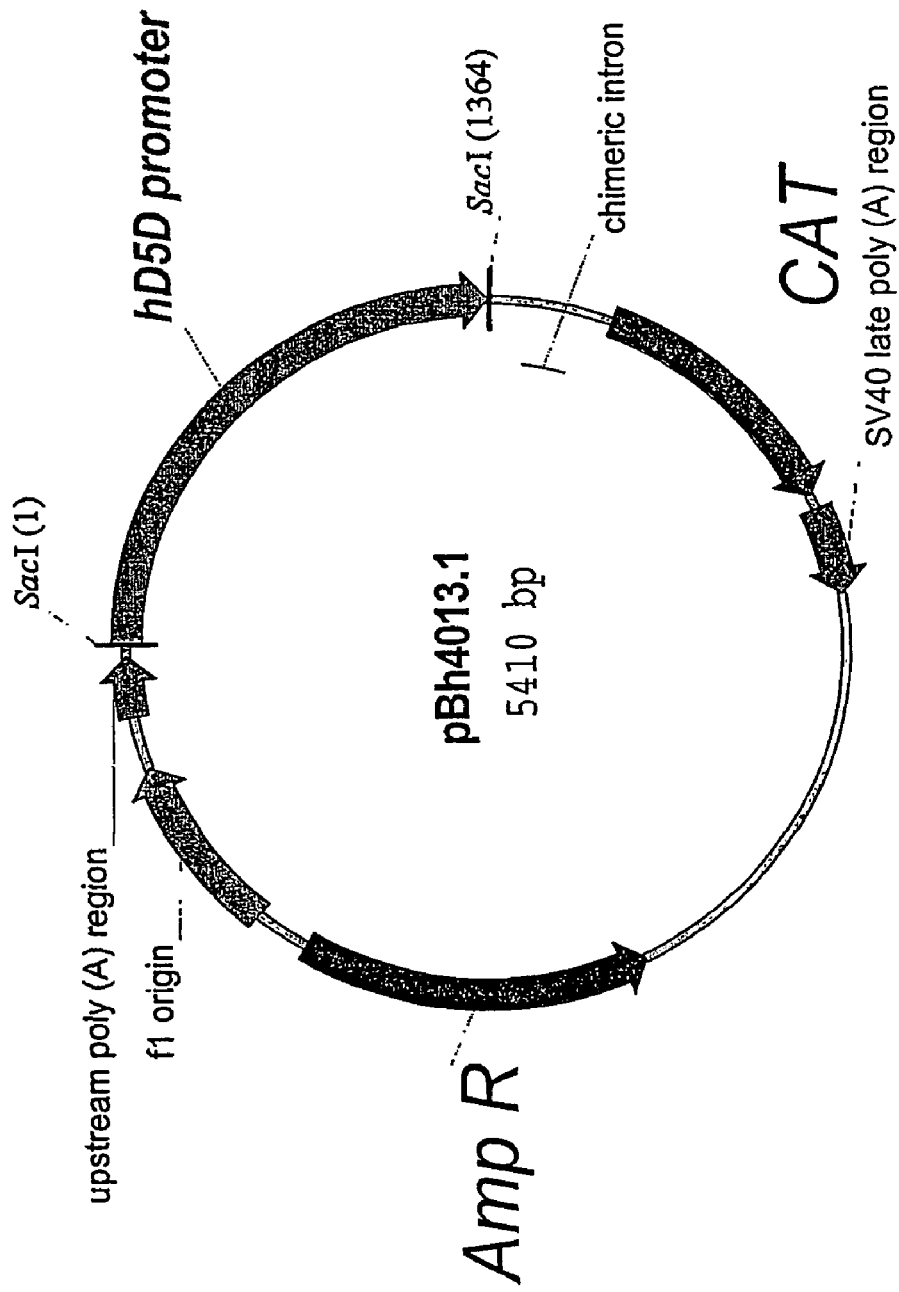
FIG. 8 is a schematic representation of plasmid pBh4013.1 (5410 bp). The human delta-5-desaturase control region is shown between restriction sites for SacI.
Figure 9:
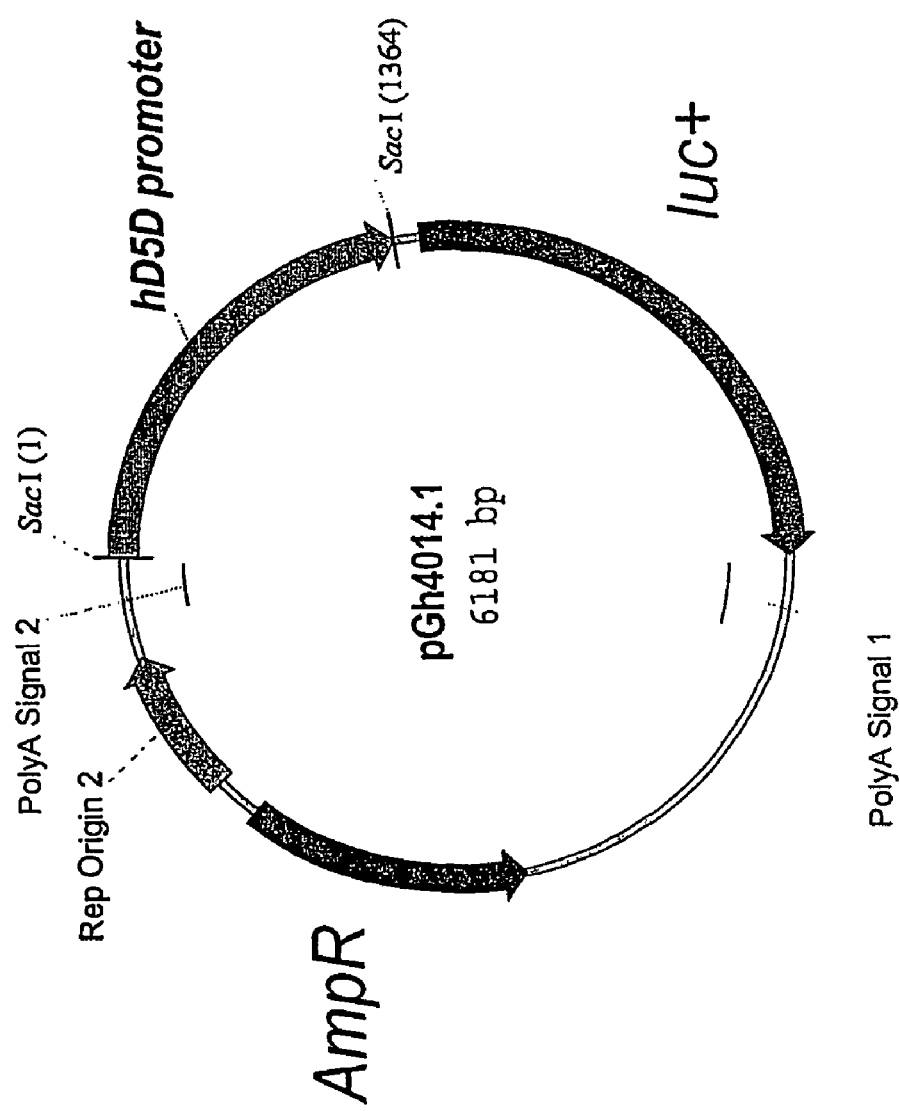
FIG. 9 is a schematic representation of plasmid pGh4014.1 (6181 bp). The human delta-5-desaturase control region is shown between restriction sites for SacI.

The forward and reverse primers used for the second PCR were 5'-GAC GAGCTCCTCAGTGCTTGGGACAGTTATGTTT-3' (SEQ ID NO. 14) and 5'-GAC GAGCTCAGCTGGCCTGGCGA-3' (SEQ ID NO. 15), respectively. The forward primer starts at position −1357 of the hD5D control region and the reverse primer starts at position −1 upstream from the ATG. Both primers contained SacI recognition sites for cloning into the SacI sites of pCAT3-Basic and pGL3-Basic vectors. The PCR conditions were the same as described previously using pCh4012.1. The gel-purified PCR product and the vectors pCAT3-Basic and pGL3-Basic were digested with the SacI restriction enzyme, ligated and transformed into competent *E. coli* strain TOP10 (Invitrogen). Colonies were selected on plates containing ampicillin. Selected colonies were amplified and plasmid DNA was isolated using QIAprep spin miniprep kit (Qiagen). The transformants were screened by restriction analysis and confirmed by DNA sequencing. The 1357 bp hD5D control region cloned in the pCAT3-Basic and pGL3-Basic vectors was named pBh4013.1 (FIG. 8) and pGh4014.1 (FIG. 9), respectively.

Example 3

Cell Tansfection

The cell lines ZR-75-1 and HepG2 are transfected with 5 μg of the plasmids pBh4013.1 and pGh4014.1 using 5 μl of Lipofectamine 2000 Reagent (Gibco BRL) in a 6-well plate as described by the manufacturer. The control plasmids pCAT-3-CTL and pCAT3-Basic or pGL3-CTL and pGL3-Basic are also transfected as positive and negative controls, respectively. In all cases, 5 μg of the plasmid pCMV-β-Gal (pCMV-β-Galactosidase control vector; Clontech) is co-transfected and used as an internal control to standardize the transfection efficiency between each transfection.

Example 4

CAT (Chloramphenicol Acetyl Transferase) Enzyme Assay

For the CAT assays, the transfected cells are harvested 48 h after transfection and cellular protein extracts are prepared using 1× Reporter Lysis Buffer (Promega). The CAT assay is done using the CAT Enzyme Assay System from Promega following the company's protocol. Essentially, about 20 μg of protein extract are incubated with 75 μCi of $[1,2-{}^{14}C]$- chloramphenicol (NEN, MA) and 25 µg of n-butyryl coenzyme A provided in the kit. The reaction mixture is incubated at 37° C. for 1 h. The reaction is then stopped by the addition of 300 µl of mixed xylenes. The xylene phase is extracted twice with 100 µl of 0.25 M Tris-HCl (pH 8.0); 200 µl of the upper xylene phase is combined with 10 ml of scintillation fluid (Ready-Safe, Beckman, Calif.) and radioactivity counted in a liquid scintillation counter. A standard curve is performed with pure CAT enzyme to ensure that the extracts are diluted enough to give a enzymatic reaction that is in the linear range of the standard curve.

The beta-galactosidase enzymatic activity is used as an internal control to standardize the transfection efficiency between transfections. The same protein extract is diluted with 1× Reporter Lysis Buffer to 150 µl and incubated with the same volume of 2× Assay Buffer (Beta-Galactosidase Enzyme Assay System, Promega) which contains 200 mM sodium phosphate buffer, pH 7.3, 2 mM $MgCl_2$, 100 mM beta-mercaptoethanol and 1.33 mg/ml o-nitrophenyl-beta-D-galactopyranoside (ONPG). The reaction mixture is incubated at 37° C. for 30 min to 1 h (until a faint yellow colour develops). The reaction is stopped by addition of 500 µl of 1 M sodium carbonate and the absorbance determined spectrophotometrically at 420 nm. The results of a typical CAT assay are provided in Table 1.

TABLE 1

Basal Activity of D5D and D6D Promoter in ZR-75-1 Cell Line

| Transfection Plasmids | *Percent Activity Compared to Controls |
|---|---|
| pRh4007.1 (D5D) | 49.71 ± 10.87 |
| pRh4002.1 (D6D) | 75.91 ± 2.00 |
| pRh4002.1 + DHA | 19.82 ± 1.41 |
| pRh4002.1 + cAMP | 93.09 ± 6.79 |
| pCat3-Enhancer | 5.80 ± 3.08 |
| pCat3-Control | 100 |

Figure 10:
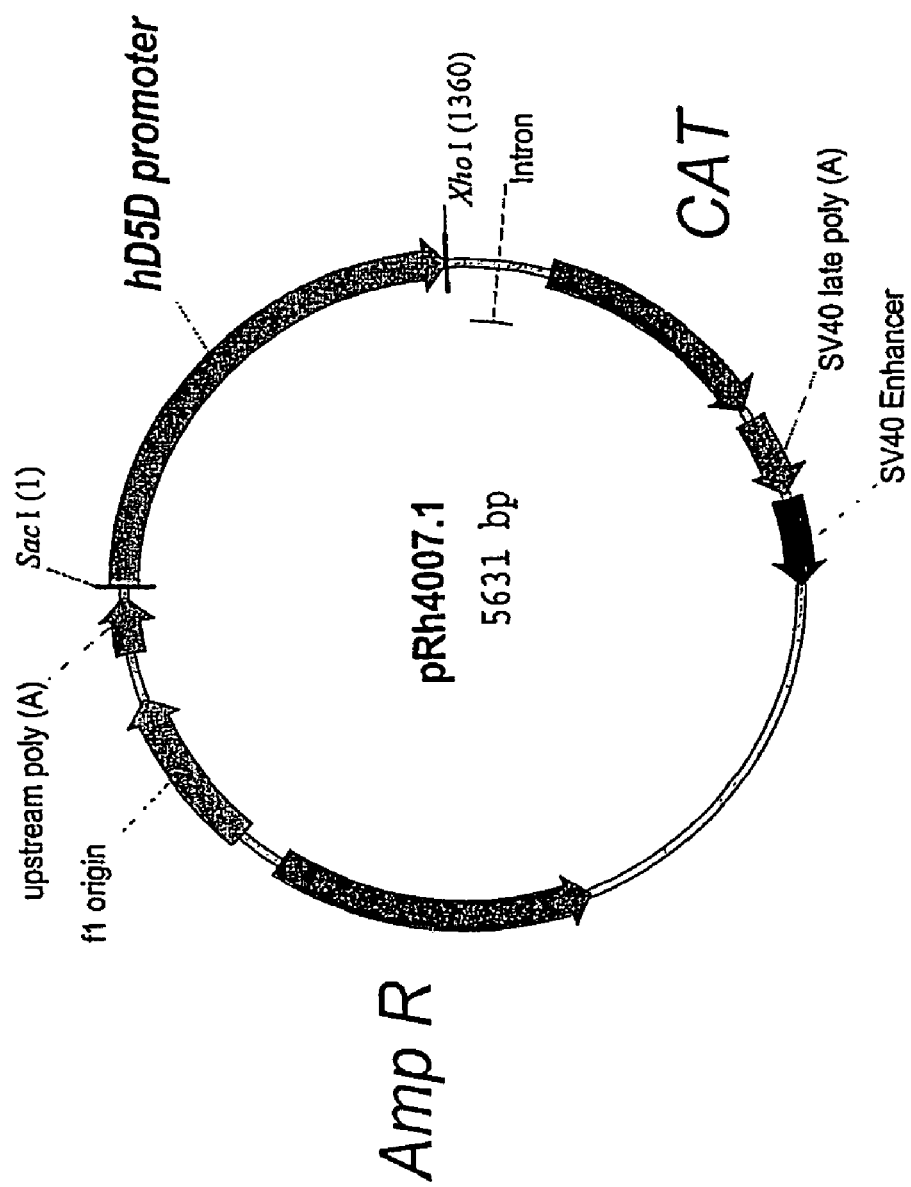
FIG. 10 is a schematic representation of plasmid pRh4007.1 (5631 bp). The human delta-5-desaturase control region is shown between restriction sites for SacI and Xho1.
Figure 11:
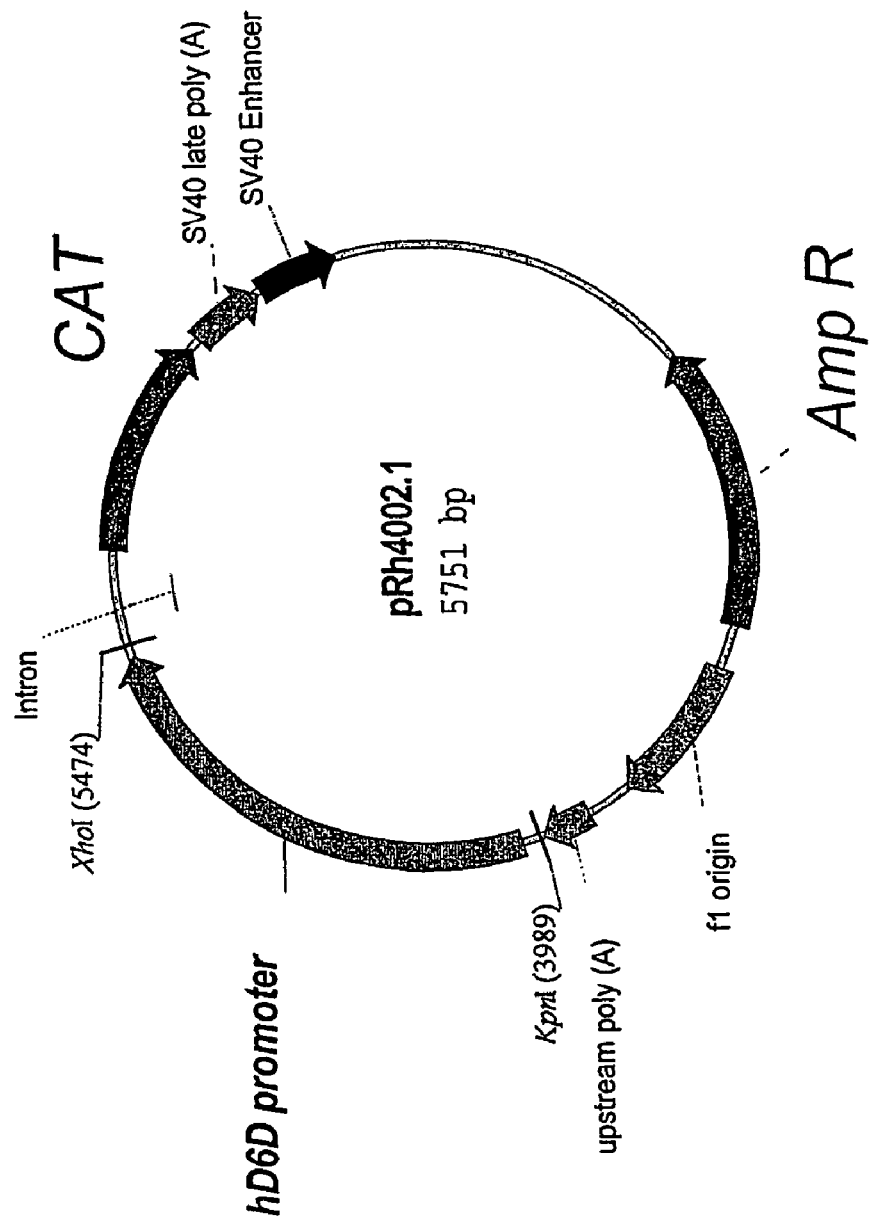
FIG. 11 is a schematic representation of plasmid pRh4002.1 (5751 bp). The human delta-6-desaturase control region is shown between restriction sites for Kpn1 and Xho1.

*Activity normalized to controls.
pRh4007.1 (FIG. 10)
pRh4002.1 (FIG. 11)

Example 5

Luciferase Enzyme Assay

For the luciferase assays, the transfected cells are harvested 48 h after transfection and cellular protein extracts are prepared using 1× Reporter Lysis Buffer (Promega) according to the company's protocol. The luciferase assay is done using the Luciferase Enzyme Assay System (Promega) following the manufacturer's recommendations.

Beta-galactosidase enzymatic activity is used as an internal control to standardize the transfection efficiency between transfections as described in Example 4.

Example 6

Functional Analysis of Delta-5-Desaturase in *Saccharomyces cerevisiae* Transformed with pYr5014.1

Chemicals and radiochemicals: Yeast nitrogen base without amino acids was purchased from Difco (Becton Dickinson Co). Fatty acid free bovine serum albumin, Tris-HCl, tergitol, carbohydrates, amino acids and fatty acids were obtained from Sigma-Aldrich Canada (Oakville, ON, Canada). All organic solvents (HPLC grade) were obtained from Fisher-Scientific (Fair Lawn, N.J.).

[1-$^{14}$C]-alpha-linolenic acid and [1-$^{14}$C]-dihomogamma-linolenic acid (99% radiochemical purity; specific activity: 52 µCi/µmol), were purchased from NEN (Boston, Mass., USA). These fatty acids were saponified with KOH (0.1 M) and dissolved in SC-U medium with 1% tergitol.

Incubation: *Saccharomyces cerevisiae* transformed with pYr5014.1 was incubated in a 125 ml Erlenmeyer containing 10 ml of SC-U medium, 1% tergitol (O.D. 0.4, approximately $3.2 \times 10^6$ cells/ml) and 2 µM (1 µCi) of the potassium salts of either [1-$^{14}$C]-alpha-linolenic or [1-$^{14}$C]-dihomogammalinolenic acids. After 5 h incubation in an orbital incubator at 270 rpm and 30° C., cells reached the log phase and the transgene expression was induced with galactose (2% final concentration). Yeast was further incubated for 19 h until they were harvested by centrifugation at 5000×g for 10 minutes at 4° C.

Cells were washed with Tris-HCl buffer (100 mM, pH 8.0) containing 0.1% BSA and total lipids were extracted as described below. The radioactivity from aliquots of the incubation medium, supernatant and the cells was determined by liquid scintillation counting using a LS6500-Scintillation System (Beckman).

The host yeast transformed with pYES2 vector was used as negative control.

Lipid Extraction: Total lipids were extracted from cells with chloroform/methanol (2:1 v/v) according to the method of Folch et al., 1957, *J. Biol. Chem.*, 226: 497-509. The total lipid extracts were methylated using boron trifluoride in methanol at 90° C. for 30 min. The resultant methyl esters (FAME) were analyzed as described below.

High Performance Liquid Chromatography (HPLC) Analysis: Analyses of radiolabelled FAMEs were carried out on a Hewlett Packard (1090, series II) chromatograph equipped with a diode array detector set at 205 nm, a radioisotope detector (model 171, Beckman, Fullerton, Calif.) with a solid scintillation cartridge (97% efficiency for $^{14}$C-detection) and a reverse-phase ODS (C-18) Beckman column (250 mm×4.6 mm i.d.; 5 µm particle size) attached to a pre-column with a µBondapak C-18 (Beckman) insert. FAMEs were separated isocratically with acetonitrile/water (95:5 v:v) at a flow rate of 1 ml/min and were identified by comparison with authentic standards. Alternatively, fatty acid methyl esters are analyzed by capillary column gas chromatography (GC).

Figure 12:
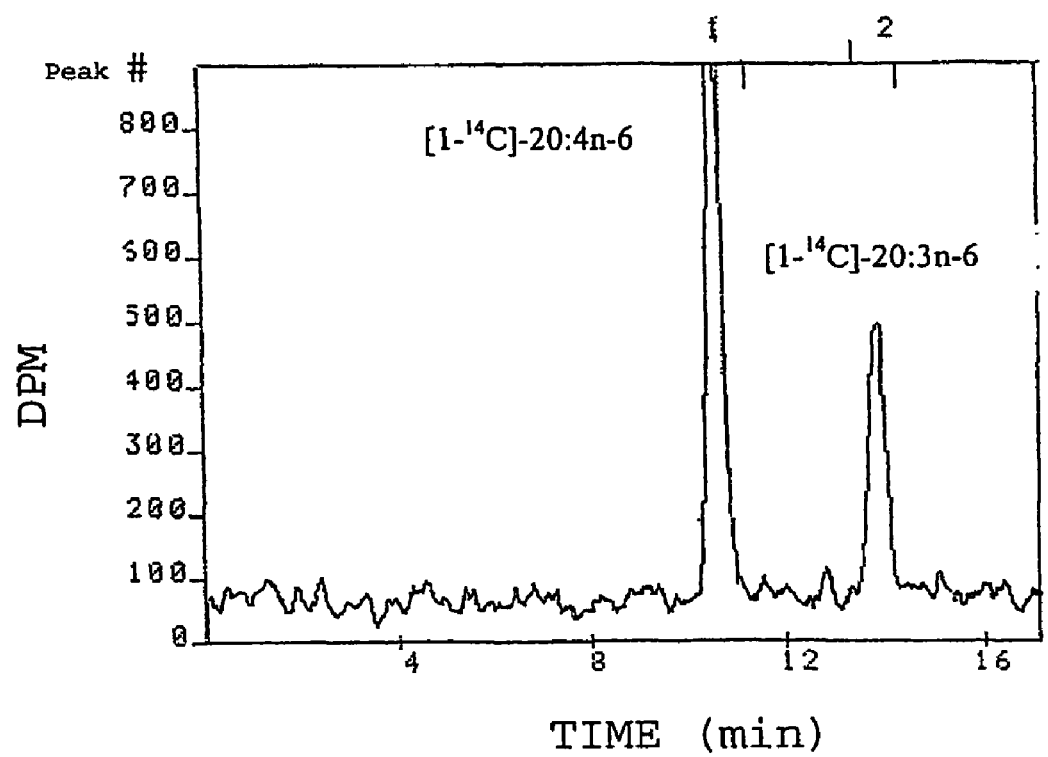
FIG. 12 shows a High Performance Liquid Chromatographic (HPLC) analysis of radiolabelled methyl esters of fatty acids from yeast transformed with pYr5014.1 incubated with dihomogammalinolenic acid, $[1-^{14}C]$-20:3n-6.
Figure 13:
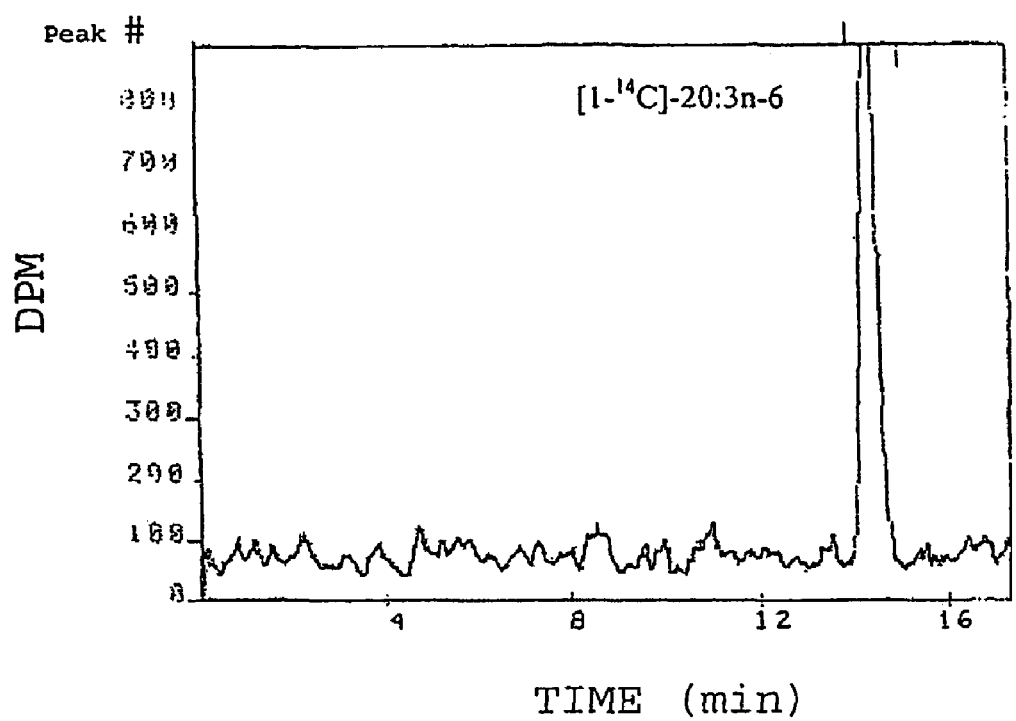
FIG. 13 shows a High Performance Liquid Chromatographic (HPLC) analysis of radiolabelled methyl esters of fatty acids from yeast transformed with pYES2 incubated with dihomogammalinolenic acid, $[1-^{14}C]$-20:3n-6.

Results: The analysis by reverse phase-high performance liquid chromatography (RP-HPLC) revealed that only [1-$^{14}$C]-dihomogammalinolenic acid was converted into arachidonic acid (20:4n-6, AA) in yeast transformed with pYr5014.1 (Example 1, FIG. 12). Such enzyme activity was not detected in the host yeast transformed with pYES2 (FIG. 13). [1-$^{14}$C]-alpha-linolenic acid was not desaturated. This finding confirmed that pYr5014.1 contains a delta-5-desaturase rather than a delta-6-desaturase.

TABLE 2

Percent of substrate conversion and radioactivity recovered in *Saccharomyces cerevisiae* cells transformed with pYr5014.1, 19 h after the induction with galactose.

| % Conversion | | % radioactivity recovered in cells | |
|---|---|---|---|
| 20:3n − 6 → 20:4n − 6 | 18:3n − 3 → 18:4n − 3 | 20:3n − 6 | 18:3n − 3 |
| 66 ± 4 | 0 | 0.6 ± 0.1 | 0.6 ± 0.1 |

Values are the mean ± S.D. of three yeast cultures derived form the same transformed colony.
O.D.$_{600}$: 6.7 ± 1.9

Conclusion: The functional analysis of the rat gene contained in the transgenic plasmid pYr5014.1 confirmed that the gene encodes a fatty acid delta-5-desaturase which is active on dihomogammalinolenic acid (20:3n-6).

Example 7

Functional Analysis of Delta-5-Desaturase Using $\Delta^{8,11,14,17}$ Eicosatetraenoic Acid (20:4n-3, ETA) as Substrate in *Saccharomyces cerevisiae* Transformed With pYr5014.1 or pTh5009.1

Chemicals and radiochemicals: Chemicals and culture medium have been described in Example 6. [1-$^{14}$C]-$\Delta^{8,11,14,17}$ eicosatetraenoic acid (99% radiochemical purity; specific activity: 55 µCi/µmol) was purchased from ARC (St Louis, Mo., USA), saponified with KOH (0.1 M) and dissolved in SC-U medium with 1% tergitol.

Incubation: *Saccharomyces cerevisiae* transformed with pYr5014.1 or pTh5009.1 was incubated in a 125 ml Erlenmeyer containing 10 ml of SC-U medium, 1% tergitol (O.D. 0.4, approximately $3.2 \times 10^6$ cells/ml) and 2 µM (1 µCi) of the potassium salts [1-$^{14}$C]-20:4n-3. The transgene expression was induced with galactose (2% final concentration). After 24 h incubation in an orbital incubator at 270 rpm and 30° C. yeast cells were harvested by centrifugation at 5000×g for 10 minutes at 4° C. Cells were washed with Tris-HCl buffer (100 mM, pH 8.0) containing 0.1% BSA and total lipids were extracted as described in Example 6. The radioactivity from aliquots of the incubation medium, supernatant and the cells was determined by liquid scintillation counting using a LS6500-Scintillation System (Beckman).

The host yeast transformed with pYES2 vector was used as negative control.

Lipid Extraction and HPLC analysis: Total lipids were extracted from cells with chloroform/methanol (2:1 v/v), methylated and analyzed as described in Example 6.

Figure 14:
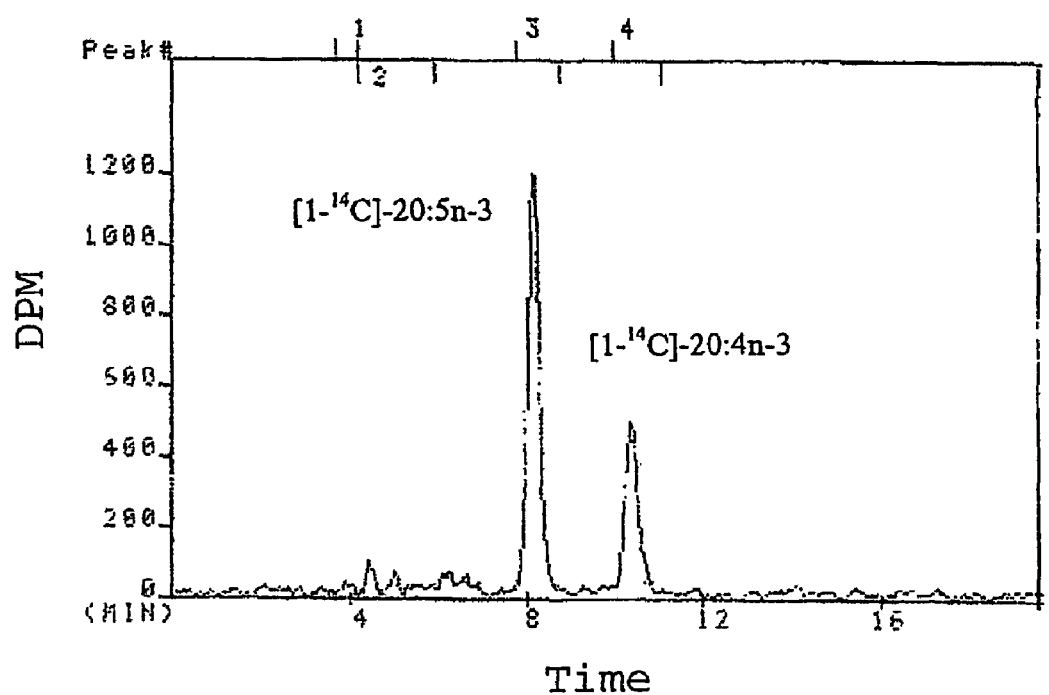
FIG. 14 shows a High Performance Liquid Chromatographic (HPLC) analysis of radiolabelled methyl esters of fatty acids from yeast transformed with pYr5014.1 or pTh5009.1 incubated with eicosatetraenoic acid, $[1-^{14}C]$-20:4n-3.
Figure 15:
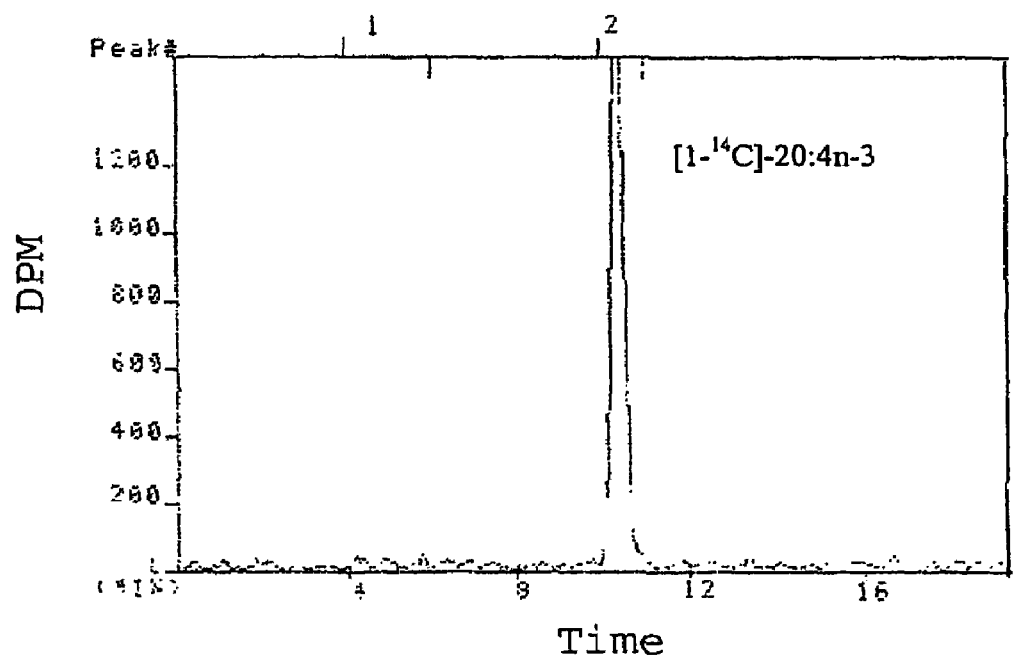
FIG. 15 shows a High Performance Liquid Chromatographic (HPLC) analysis of radiolabelled methyl esters of fatty acids from yeast transformed with pYES2 incubated with eicosatetraenoic acid, $[1-^{14}C]$-20:4n-3.

Results: The analysis by reverse phase-high performance liquid chromatography (RP-HPLC) revealed that 68% of [1-$^{14}$C]-$\Delta^{8,11,14,17}$ eicosatetraenoic acid (20:4n-3; ETA) was converted into eicosapentaenoic acid (20:5n-3, EPA) in yeast transformed with pYr5014.1 or pTh5009.1 (FIG. 14). Such enzyme activity was not detected in the host yeast transformed with pYES2 (FIG. 15).

Conclusion: These findings confirmed and expanded those described in Example 6. The inventors' results are the first to demonstrate the conversion of both, DLL into AA (Example 6) and ETA into EPA, by the same mammalian recombinant delta-5-desaturase.

Example 8

Functional Analysis of Delta-5-Desaturase in Spheroplasts from *Saccharomyces cerevisiae* Transformed with Either pYr5014.1 or pTh5009.1

Chemicals and radiochemicals: DTT (dithiothreitol), lyticase, sorbitol, tergitol, Tris-HCl, fatty acid-free bovine serum albumin, carbohydrates, amino acids and fatty acids were obtained from Sigma-Aldrich Canada. All organic solvents (HPLC grade) were provided by Fisher-Scientific: Yeast nitrogen base without amino acids was purchased from Difco. [1-$^{14}$C]-dihomogammalinolenic acid (99% radiochemical purity; specific activity: 52 µCi/µmol) was purchased from NEN. This fatty acid was saponified with KOH (0.1 M) and dissolved in SC-U medium with 1% raffinose and 1% tergitol.

Spheroplast preparation: Cultures of *Saccharomyces cerevisiae*, transformed with either pYr5014.1 or pTh5009.1 were grown in SC-U medium with 1% raffinose and 2% galactose to induce the expression of the gene that encodes the fatty acid delta-5-desaturase. After 16 h incubation, cells were centrifuged at 2060×g for 5 min at 4° C., washed once with distilled water and centrifuged again. The volume and weight of the cell pellet were measured. Cells were suspended (1:2 w/v) in 0.1 M Tris.SO$_4$ (pH 9.4), 10 mM DTT and incubated at 30° C. After 10 min incubation, the cell pellet was obtained by centrifugation, washed once (1:20 w/v) with 1.2 M sorbitol and suspended (1:1 w/v) in 1.2 M sorbitol, 20 mM phosphate buffer (pH 7.4) as described elsewhere (Daum et al., 1982, *J. Biol. Chem.*, 257: 13028-13033). The 15,800×g (1 min) supernatant of lyticase was added to the cell suspension at a concentration of 2000 U/ml and the suspension incubated at 30° C. with 50 rpm shaking. Conversion to spheroplasts was checked after 40 min incubation by diluting the suspension with distilled water followed by observation under the microscope (Schatz G. and Kovac L., 1974, *Meth. Enymol.*, 31A: 627-632). After 70 min incubation, approximately 90% of the cells were converted to spheroplasts.

Incubation: Spheroplasts were harvested by centrifugation at 2060×g for 5 min at 4° C., washed once with 1.2 M sorbitol and resuspended in SC-U medium with 1% raffinose, 1% tergitol, 1.2 M sorbitol and 2% galactose, to maintain the induction conditions and to give an O.D.$_{600}$ reading of approximately 2.5 to 3. An aliquot of 10 ml of the spheroplast suspension was transferred to 125 ml Erlenmeyer flasks and incubated with 2 µM (1 µCi) of delta-5-desaturase substrate, [1-$^{14}$C]-dihomogammalinolenic acid, at 30° C. in an orbital incubator at 270 rpm. After 150 min incubation cell density was determined (O.D.$_{600}$) and spheroplasts were harvested by centrifugation and washed with Tris-HCl buffer (100 mM, pH 8.0) containing 0.1% BSA. Total lipids were extracted as described below. The radioactivity from aliquots of the cell suspension, the supernatant and spheroplast extracts was determined by liquid scintillation counting using a LS6500-Scintillation System (Beckman).

Lipid extraction and analysis: Total lipids were extracted with chloroform/methanol and fatty acids methylated using BF$_3$ in methanol and analyzed by HPLC as described in Example 6. Alternatively, fatty acid methyl esters are analyzed by capillary column gas chromatography (GC).

Results: A similar percentage of radioactivity from [1-$^{14}$C]-dihomogammalinolenic acid added to the incubation medium was recovered in spheroplasts from yeast transformed with either pYr5014.1 or pTh5009.1 containing delta-5-desaturase genes from rat and human, respectively (Example 1). However, spheroplasts prepared from yeast cells transformed with pYr5014.1 were able to produce 3.5 times more arachidonic acid (20:4n-6) from dihomogammalinolenic acid (20:3n-6) than those transformed with pTh5009.1 (Example 1).

TABLE 3

Percent of substrate conversion and radioactivity recovered in spheroplasts from *Saccharomyces cerevisiae* transformed with pYr5014.1 or pTh5009.1, 2 h after the incubation with [1-$^{14}$C]-dihomogammalinolenic acid

| Plasmid | % Conversion 20:3n − 6 → 20:4n − 6 | % radioactivity recovered |
|---|---|---|
| pYr5014.1 | 26 ± 1 | 11 ± 2 |
| pTh5009.1 | 7.3 ± 0.6 | 9.0 ± 0.8 |

Values are the mean ± S.D. of three determinations.
O.D.$_{600}$ 2.5–3.5.
The gene expression was induced in yeast for 16 h prior the incubation with the 20:3n − 6.

Conclusion: Under these experimental conditions, spheroplasts from *Saccharomyces cerevisiae* transformed with pYr5014.1 or pTh5009.1 are able to desaturate dihomogammalinolenic acid at substantial detection levels within 2 h of incubation with the fatty acid.

Example 9

Detection of Human Delta-5-Desaturase in *Saccharomyces cerevisiae*

Growth and Induction of Expression: Yeast cells were grown under selective pressure in SC-U+2% raffinose at 30° C. in an incubator shaker using a standard procedure (Invitrogen). An overnight pre-culture of each of the transformed yeast cells was prepared, and aliquots taken to inoculate a larger volume used for the experiment. On reaching an optical density (O.D.$_{600}$=0.4–1.0), the cells were divided and harvested at 2060×g for 5 minutes. One part was stored frozen at −20° C. and used as the zero induction time, while the second part was resuspended in SC-U+2% galactose and incubated at 30° C. in an orbital shaker at 200 rpm. A time course for protein induction of the cloned gene was assessed at 0, 4, 8, 24 h by removing an aliquot from the cells grown in the presence of galactose, harvesting and storing them.

Protein extraction was then performed on the samples using cell breaking buffer (50 mM sodium phosphate, pH 7.4, 1 mM EDTA, 5% glycerol) as described by Invitrogen, with slight modifications to prepare spheroplasts. The cells were treated with lyticase (Sigma), to form spheroplasts, a cell wall digesting enzyme, at a final concentration of 2 units/ml of breaking buffer. Spheroplast formation was monitored microscopically. Cells were washed free of lyticase, harvested, weighed and resuspended in a corresponding volume of breaking buffer with 1 mM phenylmethylsulfonyl fluoride. About a half volume of acid washed glass beads approximately 0.5 mm in size was added, and the cells were broken by vortexing 3 times in a cold room (30 sec vortex and 30 sec on ice). The crude protein extract was recovered at 700×g for 3 minute. Crude extract was used for sodium dodecyl sulfate-polyacrylamide gel electrophoresis (SDS-PAGE) analysis and Western blotting.

SDS-PAGE and Western Blotting: Equal amounts of crude protein extract were mixed with sample loading buffer (50 mM Tris-HCl pH 8.0, 2% SDS, 10 mM DTT, 0.1% bromophenol blue, 10% glycerol) and boiled at 100° C. for 5 minutes. The samples, molecular weight standards (Cruz Marker from Santa Cruz Biotechnology, Inc.) and controls were loaded on 10% pre-cast SDS-polyacrylamide gels using a standard procedure (Sambrook et al., 1989, *Molecular Cloning, A Laboratory Manual*, 2$^{nd}$ edition, Cold Spring Harbour Press, Cold Spring Harbour, N.Y.). Protein samples were separated using electrophoresis buffer at constant voltage of 100 V. After electrophoresis, the gel was either stained with Coomassie Blue to assess the presence of protein, or the protein was electrophoretically transferred onto a PVDF membrane (Bio-Rad). After the transfer, the membrane was blocked with a blocking solution and incubated with a 1:10,000 dilution of anti V5-HRP antibody as described by the supplier (Invitrogen). The membrane was washed and the horseradish peroxidase reaction was detected with the Enhanced Chemiluminescence reagent ECL (Amersham-Pharmacia Biotech.). The membrane was exposed to Hyperfilm-ECL film (Amersham) in a cassette for 1-20 minutes. The film was developed and the signals scanned using Agfa DualScan 1200T (Agfa). Quantification was performed using the Gel Doc 2000 (BioRad).

Results

TABLE 4

Time course of protein expression of the human delta-5-desaturase

| | 0 time | 4 hours | 8 hours | 12 hours | 24 hours |
|---|---|---|---|---|---|
| pTh5009.1 | ND | 41% | 69% | 90% | 100% |
| pYES2/CT | ND | ND | ND | ND | ND |

Table 6 shows the relative percent of hD5D tagged protein (from pTh5009.1) in transformed yeast cells under galactose induction during a 24 hour time course. As expected, the tagged enzyme is not detectable at 0 time. The protein is detected after 4 hours and accumulates through 24 hours. The control plasmid (pYES2/CT) did not show any detectable protein (ND) during the course of the experiment.

Example 10

Inhibition of Delta-5-Desaturase Activity in Whole Cells and Spheroplasts of *Saccharomyces cerevisiae* Transformed with pYr5014.1 and pTh5009.1

Fungi, microalgae and rat liver microsomes have been used in different laboratories to test inhibitors of fatty acid delta-5-desaturase. Kawashima et al., 1996, *Biosci. Biotech. Biochem.*, 60: 1672-1676 have described a variety of compounds such as alkyl esters of gallic acid, sesamin, episesamin, sesaminol, sesamolin, diferuloyl methane, nicardipine and nifedipine that modulate the activity of delta-5-desaturase on dihomogamma-linoleic acid. More recently, p-isopentoxyaniline (Obukowicz et al., 1998, *Biochem. Pharmacol.*, 55: 1045-1058) has been also used to inhibit fatty acid delta-5-desaturase in rat liver microsomes.

3,4,5-Trihydoxybenzoic acid propyl ester (n-propyl gallate) is a noncompetitive inhibitor of fatty acid desaturases (Kawashima et al., 1996, *Biosci. Biotech. Biochem.*, 60: 1672-1676) which is commonly added as an antioxidant in fats and oils. It was selected for this example due to its substantial inhibitory effects on delta-5-desaturase and its high solubility in water or ethanol.

In the present example, *Saccharomyces cerevisiae* containing rat or human fatty acid delta-5-desaturases is used as a novel model for inhibitor (or enhancer) screening of mammalian fatty acid delta-5-desaturase. Rat liver microsomes were used to corroborate these assays.

Chemicals and radiochemicals: Propyl ester of 3,4,5-trihydroxybenzoic acid (n-propyl gallate) and other chemicals needed for spheroplasts production were obtained from Sigma-Aldrich Canada as previously described in Example 8. [1-$^{14}$C]-dihomogammalinolenic acid (DLL, 99% radiochemical purity; specific activity: 52 µCi/µmol), was purchased from NEN. This fatty acid was saponified with KOH (0.1 M) and dissolved in SC-U medium with 1% tergitol.

Spheroplast preparation: Cultures of *Saccharomyces cerevisiae* transformed with either pYr5014.1 or pTh5009.1 were grown in SC-U medium with 1% raffinose and 2% galactose to induce the expression of the gene that encodes the fatty acid delta-5-desaturase. After 16 h incubation, spheroplasts were prepared as previously described in Example 8.

Incubation of Spheroplasts: Spheroplasts were harvested by centrifugation at 2060×g for 5 min at 4° C. and washed once with 1.2 M sorbitol. Spheroplasts were suspended in SC-U medium with 1% tergitol, 1.2 M sorbitol and 2% galactose to maintain the induction conditions and to give an $O.D._{600}$ reading of approximately 2.5-3.0. A 10 ml aliquot of the spheroplast suspension was transferred to a 125 ml Erlenmeyer flask and incubated with 200 µl of n-propyl gallate in ethanol (final concentration in the culture ranged between 0.25 and 8.00 mM) at 30° C. in an orbital incubator at 270 rpm. After 30 min incubation 1 µCi of $[1-^{14}C]$-dihomogammalinolenic acid was added to the cultures to a final concentration of 2 µM and further incubated for 120 min. At this time point, turbidity readings at $O.D_{600}$ were taken, spheroplasts were harvested by centrifugation and washed with Tris-HCl buffer (100 mM, pH 8.0) containing 0.1% BSA. Total lipids were extracted and analyzed as described in Example 6.

Incubation of Whole Yeast: *Saccharomyces cerevisiae* transformed with either pYr5014.1 or pTh5009.1 were incubated in a 125 ml Erlenmeyer flask containing 9 ml of SC-U medium with 1% tergitol ($O.D._{600}$ 0.4, approximately 3.2× $10^6$ cells/ml) and 200 µl of n-propyl gallate in ethanol (final concentration in the culture ranged between 1.7-14.0 mM). After I h incubation in an orbital incubator at 270 rpm and 30° C., 1 µCi of potassium salt of $[1-^{14}C]$-dihomogammalinolenic acid (dissolved in SC-U medium and 1% tergitol) was added to the cell suspension to a final concentration of 2 µM. After 5 h incubation with the inhibitor, cells reached the log phase and the transgene expression was induced with the addition of 1 ml of galactose to a final concentration of 2%. Yeast were further incubated for 19 h ($O.D._{600}$ range: 5-10) until they were harvested by centrifugation at 5000×g for 10 minutes at 4° C. Cells were washed with Tris-HCl buffer (100 mM, pH 8.0) containing 0.1% BSA and total lipids were extracted and analyzed as described in Example 6.

Calculations: The delta-5-desaturase activity was determined by measuring the conversion of radiolabelled dihomogammalinolenic acid to arachidonic acid (20:3n-6 to 20:4n-6). The percent inhibition was calculated as described elsewhere (Kawashima et al., 1996, *Biosci. Biotech. Biochem.*, 60:1672-1676):

% Inhibition=100(activity without the inhibitor−activity with the inhibitor)/activity without the inhibitor Results: The conversion of dihomogammalinolenic acid to arachidonic acid (20:3n-6 to 20:4n-6) in spheroplasts from *Saccharomyces cerevisiae* transformed with plasmids that encode the delta-5-desaturase was inhibited by n-propyl gallate at the concentrations shown in Tables 4 and 5. The consistent $O.D._{600}$ readings (i.e. constant number of cells) and the similar levels of radioactivity recovered in cells at concentrations of n-propyl gallate between 0.7-4.0 mM indicate that the inhibitor was not affecting the uptake of substrate and that it was not cytotoxic. However, at concentrations >4.0 mM, the cell number was slightly decreased and the radioactivity recovered in those cells from the fatty acid substrate was substantially reduced demonstrating that those concentrations may be toxic for the spheroplasts.

TABLE 5

Inhibition of human delta-5-desaturase in spheroplasts of *Saccharomyces cerevisiae* transformed with pTh5009.1 and incubated with $[1-^{14}C]$-dihomogammalinolenic acid and n-propyl gallate

| Inhibitor conc. (mM) | % inhibition | $O.D._{600}$ | % radioactivity recovered |
|---|---|---|---|
| 0.00 | 0.0 | 2.6 | 9.0 |
| 0.25 | 14.6 | 2.4 | 9.5 |
| 0.50 | 17.6 | 2.5 | 9.5 |
| 1.00 | 24.0 | 2.5 | 9.8 |
| 2.00 | 41.0 | 2.2 | 9.3 |
| 4.00 | 100.0 | 2.4 | 8.9 |
| 8.00 | 100.0 | 1.2 | 4.9 |

Values are the mean of three determinations.

TABLE 6

Inhibition of rat delta-5-desaturase in spheroplasts of *Saccharomyces cerevisiae* transformed with pYr5014.1 and incubated with $[1-^{14}C]$-dihomogammalinolenic acid and n-propyl gallate

| Inhibitor conc. (mM) | % inhibition | $O.D._{600}$ | % radioactivity recovered |
|---|---|---|---|
| 0.00 | 0.0 | 3.2 | 10.7 |
| 0.25 | 4.3 | 2.8 | 9.0 |
| 1.00 | 7.0 | 2.9 | 8.3 |
| 2.00 | 20.5 | 2.7 | 8.6 |
| 4.00 | 50.4 | 2.9 | 7.6 |
| 8.00 | 81.9 | 2.8 | 3.6 |

Values are the mean of three determinations.

The induction of desaturase gene expression for 16 h prior to the addition of the inhibitor guaranteed that the observed reduction in substrate conversion was not due to an inhibition of transcription or translation for the genes.

The inhibitory effect of n-propyl gallate was also detected in whole yeast in which the desaturase gene was induced after the addition of the inhibitor (Tables 7 and 8).

TABLE 7

Inhibition of human delta-5-desaturase in whole cells of *Saccharomyces cerevisiae* transformed with pTh5009.1 and incubated with $[1-^{14}C]$-dihomogammalinolenic acid and n-propyl gallate

| Inhibitor conc. (mM) | % inhibition | $O.D._{600}$ | % radioactivity recovered |
|---|---|---|---|
| 0.0 | 0.0 | 10.9 | 0.5 |
| 1.7 | 25.0 | 9.0 | 0.5 |
| 3.5 | 63.3 | 9.9 | 0.8 |
| 7.0 | 100.0 | 10.5 | 0.7 |

Values are the mean of three determinations.

TABLE 8

Inhibition of rat delta-5-desaturase in whole cells of
Saccharomyces cerevisiae transformed with pYr5014.1 and
incubated with [1-$^{14}$C]-dihomogammalinolenic acid
and n-propyl gallate

| Inhibitor conc. (mM) | % inhibition | O.D.$_{600}$ | % radioactivity recovered |
|---|---|---|---|
| 0.0 | 0.0 | 6.7 | 0.5 |
| 7.0 | 38.9 | 6.5 | 0.9 |
| 14.0 | 68.5 | 5.4 | 0.6 |

Values are the mean of three determinations.

Conclusions: Yeast spheroplasts containing delta-5-desaturases should be considered as the model of choice for desaturase assays since lower concentrations of inhibitors (than those used with the whole yeast) are required to obtain detectable changes in the enzyme activity. In this model, the solubility restrictions of the inhibitors are reduced. Furthermore, the uptake of the desaturase substrates is higher than in whole yeast which helps to increase the threshold of detection (Tables 2-5). These assays should be performed using concentrations of the inhibitors below the cytotoxic levels. The strength of this novel model for drug screening using mammalian desaturases in yeast is supported by the results obtained using the traditional method of rat liver microsomes (see Example 13).

In summary, spheroplasts from *Saccharomyces cerevisiae* containing mammalian delta-5-desaturases are useful for screening inhibitors and enhancers of the enzymes.

Although embodiments of the invention have been disclosed for illustrative purposes, it will be appreciated that variations or modifications of the disclosed apparatus lie within the scope of the present embodiments.

Example 11

Screening Delta-5-Desaturase Modulators Using Microsomes From *Saccharomyces cerevisiae* Containing Human or Mammalian Desaturases Yeast microsome preparation: Two to 51 of *Saccharomyces cerevisiae* transformed with pYr5014.1 or pTh5009.1 are started with a cell density of approximately 3.2×10$^5$ cells/ml (O.D.$_{600}$ 0.4) using SC-U medium. After 8 h of incubation at 30° C. in an orbital incubator at 270 rpm, galactose is added to a final concentration of 2%. Yeast are further incubated for 12 h, harvested by centrifugation at 2060×g for 10 minutes at 4° C. and washed with water. The cell pellet is resuspended in 1/3 of its volume in isolation buffer containing 80 mM Hepes-KOH (pH 7.2) and 10 mM KCl and 320 mM of sucrose, 2 mM phenylmethylsulfonyl fluoride and an EDTA-free tablet of protease inhibitor cocktail (one tablet per 10 g cell pellet; Complete, Roche, Germany). The cell suspension is poured into a mortar containing liquid N$_2$ and ground with sand using a ceramic pestle. The yeast powder is transferred to a conical test tube, to which isolation buffer is added (2/3 of the pellet volume). The sand is removed by centrifugation at 57×g for 1 min and the suspension is further centrifuged at 10,000×g for 20 min to separate cell debris, nuclei, and mitochondria. The supernatant is then centrifuged at 106,000×g for 1 h to obtain the microsome pellet which is resuspended in 700 μl of isolation buffer. The protein concentration of the microsome suspension is measured by any technique known in the art.

Incubation of delta-5-desaturase modulators with yeast microsomes: The activity of delta-5-desaturase is determined by measuring the conversion of [1-$^{14}$C]20:3n-6 (dihomogammalinolenic acid) to [1-$^{14}$C]20:4n-6 (arachidonic acid). Reactions are started by adding 500 μg of yeast microsomal protein, to pre-incubated tubes containing 0.20 μCi of the substrate fatty acid at a final concentration of 33 μM in 0.25 ml of the incubation solution, containing 80 mM Hepes-KOH (pH 7.2) and 43.2 mM MgCl$_2$, ATP (1.0 mM), NADH (500 μM) and coenzyme A (10 μM) and a range of concentrations of the enzyme modulators. The tubes are vortexed vigorously and after 15 min incubation in a shaking water bath (37° C.), the reactions are stopped by the addition of 2 ml of 10% (w/v) KOH in ethanol. Lipids in the incubation mixture are saponified at 80° C. for 45 min under N$_2$. The samples are left in ice for 5 min and then acidified with HCl. The fatty acids are extracted with hexane and esterified with BF$_3$/methanol at 90° C. for 30 min. The fatty acid methyl esters, substrate and product of the enzymatic reaction, are analyzed by HPLC as described in Example 6. Results are expressed in pmol of arachidonic acid produced per mg microsomal protein per minute. Alternatively, fatty acid methyl esters are analyzed by capillary column gas chromatography (GC).

Example 12

Screening Delta-5-Desaturase Modulators Using Purified Enzymes Obtained from *Saccharomyces cerevisiae* Expressing Human or Mammalian Desaturases Isolation of the delta-5-desaturase from yeast microsomes: Yeast microsomes containing delta-5-desaturase tagged with 6× His are stirred with Zwittergent 3-14 or mixtures of deoxycholate/Triton X-100 (2%, w/w) for 2 h at 4° C. to solubilize the delta-5-desaturase. Alternatively, yeast microsomes can be treated with 2.5% (v/v) water in acetone to improve the solubilizing power of the detergents. The mixture is centrifuged at 106,000×g for 1 h. The supernatant containing the enzyme is loaded onto a pre-equilibrated HiTrap chelating (Ni$^{++}$ charged iminodiacetate) column (Pharmacia) attached to a fast protein liquid chromatography system (Pharmacia). The column is washed with 50 mM sodium phosphate (pH 8.0). The tagged protein is eluted with sodium phosphate buffer containing imidazole (0-500 mM) and concentrated by ultrafiltration using Centriprep (Amicon, Mass.) concentrators.

Incubation of delta-5-desaturase modulators with purified enzyme: The concentrated enzyme is incubated at 30-37° C. in Tris-HCl buffer (pH 7.2) containing 1 mM NADH, 80 μM of cytochrome b$_5$, 4 μM of NADH-cytochrome b$_5$ reductase, 6 mM egg phosphatidylcholine, 2% Triton X-100, 0.4% sodium deoxycholate, radiolabelled dihomogammalinolenyl-CoA as the enzyme substrate and a range of concentrations of each enzyme modulator. After 15-90 min of incubation, the reaction is stopped and fatty acids, substrate and product of the enzymatic reaction, are analyzed as described in Example 6.

Alternatively, the enzyme activity and the effect of modulators of the enzyme activity can be measured by the rate of NADH oxidation in the presence and absence of dihomogammalinolenyl-CoA.

Example 13

Validation of Assays Described in Examples 9 to 11 Using Rat Liver Microsomes

Preparation rat liver microsomes: Wistar rats under light halothane (15% in mineral oil) anesthesia were sacrificed by exsanguination during periods of high enzyme activity. Livers are immediately rinsed with cold 0.9% NaCl solution, weighed and minced with scissors. All procedures are performed at 4° C. unless specified otherwise. Livers are homogenized in a solution (1:3 w/v) containing 0.25 M sucrose, 62 mM. potassium phosphate buffer (pH 7.0), 0.15 M KCl, 1.5 mM N-acetylcysteine, 5 mM $MgCl_2$, and 0.1 mM EDTA using 4 strokes of a Potter-Elvehjem tissue homogenizer. The homogenate is centrifuged at 10,400×g for 20 min to eliminate mitochondria and cellular debris. The supernatant is filtered through a 3-layer cheesecloth and centrifuged at 105,000×g for 60 min. The microsomal pellet is gently resuspended in the same homogenization solution with a small glass/teflon homogenizer and stored at −70° C. The absence of mitochondrial contamination is enzymatically assessed. The protein concentration is measured using bovine serum albumin as the standard.

Incubation of rat liver microsomes with delta-5-desaturase modulators: Reactions are started by adding 2 mg of microsomal protein to pre-incubated tubes containing 0.20 µCi of the substrate fatty acid (DLL) at a final concentration of 33.3 µM in 1.5 ml of homogenization solution, containing NaF (42 mM), niacinamide (0.33 mM), ATP (1.57 mM), NADH (1.0 mM), coenzyme A (0.09 mM) and a range of concentrations of the enzyme modulators. N-propyl gallate was added to the incubation medium to a final concentration of 0.02-0.32 mM. The tubes are vortexed vigorously and after 15 min incubation in a shaking water bath (37° C.), the reactions are stopped and fatty acids are analyzed as described in Example 6. Alternatively, fatty acid methyl esters are analyzed by capillary column gas chromatography (GC).

Table 11 shows the in vitro inhibition of delta-5-desaturase with different concentrations of n-propyl gallate in rat liver microsomes. A plateau was reached at concentration of the inhibitor that ranged between 0.08-0.32 mM.

TABLE 9

Inhibition of delta-5-desaturase activity in rat liver microsomes incubated with [1-$^{14}$C]-dihomogammalinolenic acid and n-propyl gallate.

| Inhibitor conc. (mM) | % of inhibition |
|---|---|
| 0.00 | 0.0 |
| 0.02 | 62.9 |
| 0.04 | 74.9 |
| 0.08 | 86.4 |
| 0.16 | 88.7 |
| 0.32 | 100.0 |

Values are the mean of three determinations. Enzyme activity without inhibitor: 394 pmol/mg microsomal protein/min.

Example 14

Screening of Delta-5 and Delta-6 Desaturase Modulators Using *Saccharomyces cerevisiae* Whole Cells, Spheroplasts or Microsomes Containing Human or Mammalian Delta-5 and Delta-6-Desaturases This method is suitable for simultaneous drug screenings of both fatty acid desaturases under the same experimental conditions. The specificity of each drug for each enzyme is rapidly determined by this method.

Co-expression of human or mammalian delta-5 and delta-6-desaturases in yeast: Delta-6 and delta-5 desaturase genes are cloned in 2 separate yeast vectors (constitutive or inducible), having different nutritional selection markers, for examples, URA3 and LEU2 genes which confer uracil and leucine prototrophy for selection in yeast. A yeast strain having an auxotrophic requirement for uracil and leucine is transformed with the two plasmids. Yeast cells containing the plasmids are selected on synthetic minimal medium lacking both uracil and leucine. The activity of the two desaturases is then assayed and used for screening of modulators.

Alternatively, bi-directional yeast vectors, for example the pBEVY plasmids (Miller et al., 1998, *Nucl. Acid Res.* 26:3577-3583), are used to co-express the desaturase genes. The pBEVY plasmids provide for either constitutive or galactose-induced expression of exogenous genes.

The fatty acid desaturase genes are cloned downstream of the constitutive glyeraldehyde-3-phosphate dehydrogenase (GPD) and the alcohol dehydrogenase 1 (ADH1) promoters, respectively, using methods known to those skilled in the art. Alternatively, the genes are cloned on both sides of the bi-directional galactose inducible promoter GAL1/GAL10. A suitable yeast strain (auxotrophic for a nutritional requirement, e.g. uracil) is transformed with desaturase constructs (for example, which confer uracil prototrophy). Such yeast transformants are selected in SC-U medium. The selected transformants are grown in appropriate media to allow constitutive or inducible expression of the two proteins.

The present method utilizes bi-directional vectors expressing mammalian fatty acid delta-5 and delta-6-desaturases to screen simultaneously for unique modulators of both or either activities that may have therapeutic, diagnostic or nutritional function.

Whole yeasts or spherorlasts: The enzymatic assay with modulators of both enzymes is similar to that described above (Example 10). In this model, the radiolabelled substrates for delta-6 and delta-5-desatuases, alpha-linolenic (18:3n-3) and DLL (20:3n-6) acids, respectively, are both added in the incubation medium. After 2-19 h of incubation the remnant radiolabelled substrates and products (stearidonic acid, 18:4n-3, and arachidonic acid, 20:4n-6, respectively) of the enzymatic reaction are analyzed by HPLC as described in Example 6. Alternatively, fatty acid methyl esters are analyzed by capillary column gas chromatography (GC).

Microsomes: Microsomes from yeast containing human delta-6- and delta-5-desaturases or both mammalian (e.g. rat) delta-6- and delta-5-desaturases are obtained as previously described (Example 11). The incubation is similar to that used with microsomes containing only one human or mammalian desaturase with the exception that radiolabelled alpha-linolenic acid (18:3n-3) and DLL (20:3n-6), substrates for delta-5 and delta-6-desaturases, respectively, are both added to the incubation medium along with a range of different concentrations of desaturase modulators. The products of the enzymatic reaction are analyzed by HPLC as described in Example 6. Alternatively, fatty acid methyl esters are analyzed by capillary column gas chromatography (GC).

Example 15

Generation of Polyclonal Antibody Against the Subject Polynucleotide

Segments of the subject polynucleotide coding sequence are expressed as fusion protein in *E. coli*. The over-expressed protein is purified by gel elution and used to immunize rabbits and mice using a procedure similar to the one described by Harlow E. and Lane D. (eds.), 1988, *Antibodies: A Laboratory Manual*, Cold Harbour Press, Cold Harbour, N.Y. This procedure has been shown to generate antibodies against various other proteins (Kraemer et al., 1993, *J. Lipid Res.*, 34: 663-671).

Briefly, a stretch of coding sequence selected from the subject polynucleotide is cloned as a fusion protein in plasmid PETSA (Novagen, Inc., Madison, Wis.). After induction with IPTG, the over-expression of a fusion protein with the expected molecular weight is verified by SDS/PAGE. Fusion protein is purified from the gel by electro-elution. The identification of the protein as the subject polypeptide fusion product is verified by protein sequencing at the N-terminus. Next, the purified protein is used as immunogen in rabbits. Rabbits are immunized with 100 µg of the protein in complete Freund's adjuvant and boosted twice in 3 week intervals, first with 100 µg of immunogen in incomplete Freund's adjuvant followed by 100 µg of immunogen in PBS. Antibody containing serum is collected two weeks thereafter.

This procedure is repeated to generate antibodies against the mutant forms of the subject polypeptide. These antibodies, in conjunction with antibodies to wild type subject polypeptide, are used to detect the presence and the relative level of the mutant forms in various tissues and biological fluids.

Example 16

Generation of Monoclonal Antibodies Specific for the Subject Polypeptide

Monoclonal antibodies are generated according to the following protocol. Mice are immunized with immunogen comprising intact subject polypeptide or its peptides (wild type or mutant) conjugated to keyhole limpet hemocyanin using glutaraldehyde or EDC as is well known.

The immunogen is mixed with an adjuvant. Each mouse receives four injections of 10 to 100 µg of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (Harlow E. and Lane D. (eds.), 1988, *Antibodies: A Laboratory Manual*, Cold Harbour Press, Cold Harbour, N.Y.). Cell fusions are performed essentially as described by Kohler G. and Milstein C., 1975, *Nature*, 256: 495-497. Briefly, P3.65.3 myeloma cells (American Type Culture Collection, Rockville, Md.) are fused with immune spleen cells using polyethylene glycol as described by Harlow E. and Lane D. (eds.), 1988, *Antibodies: A Laboratory Manual*, Cold Harbour Press, Cold Harbour, N.Y. Cells are plated at a density of $2 \times 10^5$ cells/well in 96 well tissue culture plates. Individual wells are examined for growth and the supernatants of wells with growth are tested for the presence of subject polypeptide specific antibodies by ELISA or RIA using wild type or mutant target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development

Example 17

Sandwich Assay for the Subject Polypeptide

Monoclonal antibody is attached to a solid surface such as a plate, tube, bead, or particle. Preferably, the antibody is attached to the well surface of a 96-well ELISA plate. 100 µl sample (e.g., serum, urine, tissue cytosol) containing the subject polypeptide/protein (wild-type or mutant) is added to the solid phase antibody. The sample is incubated for 2 hrs at room temperature. Next the sample fluid is decanted, and the solid phase is washed with buffer to remove unbound material. 100 µl of a second monoclonal antibody (to a different determinant on the subject polypeptide/protein) is added to the solid phase. This antibody is labeled with a detector molecule (e.g., $^{125}$I, enzyme, fluorophore, or a chromophore) and the solid phase with the second antibody is incubated for two hrs at room temperature. The second antibody is decanted and the solid phase is washed with buffer to remove unbound material.

The amount of bound label, which is proportional to the amount of subject polypeptide/protein present in the sample, is quantitated. Separate assays are performed using monoclonal antibodies, which are specific for the wild-type subject polypeptide, as well as monoclonal antibodies specific for each of the mutations identified in subject polypeptide.

REFERENCES

U.S. Pat. No. 3,817,837, June, 1974, Rubinstein et al.
U.S. Pat. No. 3,850,752, November, 1974, Schuurs et al.
U.S. Pat. No. 3,939,350, February, 1976, Kronick et al.
U.S. Pat. No. 3,996,345, December, 1976, Ullman et al.
U.S. Pat. No. 4,277,437, July, 1981, Maggio
U.S. Pat. No. 4,275,149, June, 1981, Litman et al.
U.S. Pat. No. 4,366,241, December, 1982, Tom et al.
U.S. Pat. No. 4,816,567, March, 1989, Cabilly et al.
International Patent Application No. WO 88/04300, June, 1988, Cech et al.
Patent Cooperation Treaty International Publication No. WO 93/05182, March, 1993, Bruice, T. W.
Aki et al., 1999, *Biochem. Biophys. Res. Commun.*, 255: 575-579
Altschul et al., 1990, *J. Molec. Biol.*, 215: 403-410
Anderson et al., 1998, *Anticancer Res.*, 18: 791-800
Arisaka et al., 1986, *J. Paediatr. Gastroenterol Nutr.*, 5: 878-882
Ausubel et al., 1994-, *Current Protocols in Molecular Biology*, John Wiley & Sons, New York, N.Y.
Been M. D. and Cech T. R., 1986, *Cell*, 47: 207-216
Booyens et al., 1985, *Med. Hypotheses*, 18: 53-60
Brenner et al., 1968, *Am. J. Physiol.*, 215: 63-70
Calder P. C., 1998, *Braz. J. Med. Biol. Res.*, 4: 467-490
Calviello et al., 1998, *Int. J. Cancer*, 75: 699-705

Copsey D. N. and Delnatte S. Y. J., 1988, *Genetically Engineered Human Therapeutic Drugs*, Stockton Press, New York.
Carillo H. and Lipman D., 1988, *SIAM J. Applied Math.*, 48: 1073
Chavali S. R. and Forse R. A., 1999, *Prostaglandins Leukot. Essent. Fatty Acids*, 61: 347-352
Cho et al., 1999a, *J. Biol. Chem.*, 274: 471-477
Cho et al., 1999b, *J. Biol. Chem.*, 274: 37335-37339
Coste et al., 1999, *J. Nutr. Biochem.*, 10: 411-420
Curtis et al., 2000, *J. Biol. Chem.* 275: 721-724
Dang et al., 1989, *Lipids*, 24: 882-889
Das U., 1995, *Prostaglandins Leukot. Essent. Fatty Acids*, 52: 387-391
Daum et al., 1982, *J. Biol. Chem.*, 257: 13028-13033
de Antueno et al., 1994, *Lipids*, 29: 327-331
Deutcher M., (editor), 1990, *Guide to Protein Purification*, Meth in Enzymol, 182
Devereux et al., 1984, *Nucl. Acid Res.*, 12(1): 387-395
Dobner P. and Engelmann B., 1998, *Am. J. Physiol.*, 275: E777-E784
du Toit et al., 1994, *Prostaglandins Leukot. Essent. Fatty Acids*, 51: 121-124
Faas F. H. and Carter W. J., 1980, *Lipids*, 15: 953-961
Falconer et al., 1994, *Br. J. Cancer*, 69: 826-832
Folch et al., 1957, *J. Biol. Chem.*, 226: 497-509
Fujiwara et al., 1983, *Biochem. Biophys. Res. Commmun.*, 110: 36-41
Fujiwara et al., 1984, *Arch. Biochem. Biophys.*, 233: 402-407
Gadek et al., 1999, *Crit. Care Med.* 27: 1409-1420
Goding J. W., 1996, *Monoclonal Antibodies: Principles and Practice: Production and Application of Monoclonal Antibodies in Cell Biology, Biochemistry and Immunology*, $3^{rd}$ edition, Academic Press, New York;
Gribskov M. and Devereux J., eds., 1991, *Sequence Analysis Primer*, M Stockton Press, New York
Griffin A. M. and Griffin H. G., eds., 1994, *Computer Analysis of Sequence Data, Part 1*, Humana Press, New Jersey
Guthrie C. and Fink G., 1991, *Meth. Enzymol*, 194
Hanahan et al., 1983, *J. Mol. Biol.*, 166: 557-580
Hansen A. E., 1933, *Proc. Soc. Exp. Biol. Med.* 31: 1160-1161
Harbige L. S., 1998, *Proc. Nutr. Soc.*, 4: 555.562
Harlow E. and Lane D. (eds.), 1988, *Antibodies: A Laboratory Manual*, Cold Harbour Press, Cold Harbour, New York
Haseloff J. and Gerlach W. L., 1988, *Nature*, 334: 585-591
Huse et al., 1989, *Science*, 246: 1275-1281
Izant J. G. and Weintaub H., 1984, *Cell*, 36:1007-1015
James et al., 2000, *Am J. Clin. Nutr.*, 71: 343S-348S
Jiang et al., 1995a, *Cancer Res.*, 55: 5043-5048
Jiang et al., 1995b, *Br. J Cancer*, 71: 744-752
Jiang et al., 1997, *Prostaglandins Leukot. Essent. Fatty Acids*, 56: 307-316
Jiang et al., 1998a, *Br. J. Cancer*, 77: 731-738
Jiang et al., 1998b, *Biochem. Biophys. Res. Commun.*, 244: 414-420
Jiang et al., 2000, *Prostaglandins Leukot. Essent. Fatty Acids*, 62: 119-127
Johnston M., 1987, *Microbiol. Rev.*, 51: 458-476
Julu P., 1998, in *Essential Fatty Acids and Eicosanoids*, AOCS Press, Ill., U.S.A. pp.168-175
Kawashima et al., 1996, *Biosci. Biotech. Biochem.*, 60: 1672-1676
Keen et al., 1993, *Diabetes Care*, 16: 8-15
Khan et al., 1995, *Cell. Signal.*, 7: 171-184
Kohler G. and Milstein C., 1975, *Nature*, 256: 495-497
Kraemer et al., 1993, *J. Lipid Res.*, 34:.663-671
Lai et al., 1996, *Br. J. Cancer*, 74: 1375-1383
Leonard et al., 2000, *Biochem. J.*, 347: 719-724
Lesk A. M., ed., 1988, *Computational Molecular Biology*, Oxford University Press, New York
Lippiello et al., 1991, *Metabolism* 40: 571-576
Llewellyn et al., 1987, *J. Mol. Biol.*, 195: 115-123
Lue et al., 1987, *Mol. Cell. Biol.*, 7: 3446-3451
Mack E. W., 1990, *Remington's Pharmaceutical Sciences*, Mack Publishing Company, Easton, Pa., $13^{th}$ edition
Manku et al., 1984, *Br. J. Dermatol.*, 110: 643-680
Margolskee et al., 1988, *Mol. Cell. Biol.*, 8: 2837-2847
Marquardt et al., 2000, *Genomics*, 66: 175-183
Mayser et al., 1998, *J. Am. Acad. Dermatol.* 38: 539-547
McLaughlin et al., 1988, *J. Virol.*, 62: 1963-1973
Miller et al., 1998, *Nucl. Acid Res.*, 26: 3577-3583
Mimouni V. and Poisson J. P., 1992, *Biochem. Biophys. Acta*, 1123: 296-302
Moss et al., 1987, *Annu. Rev. Immunol.*, 5: 305-324
Navarro et al., 2000, *J. Rheumatol.*,27:-298-303
Nishi et al., 2000, *Biochim. Biophys. Acta*, 1490: 106-108
Obukowicz et al., 1998, *Biochem. Pharmacol.*, 55:1045-1058
Okano et al., 1988, *EMBO J.*, 7: 3407-3412
Orkin et al., 1988, *Prog. Med. Genet.*, 7: 130-142
Plumb et al., 1993, *Br. J. Cancer*, 67: 728-733
Rasmussen et al., 1987, *Meth. Enzymol.*, 139: 642-654
Rosenberg et al., 1985, *Nature*, 313: 703-706
Russo et al., 1997, *Hypertension*, 4: 1058-1063
Sambrook et al., 1989, *Molecular Cloning, 2nd Edition*, Cold Spring Harbor Laboratory Press, Cold Spring Harbour, N.Y.
Schatz G. and Kovac L., 1974, *Meth. Enzymol.*, 31A: 627-632
Seegers et al., 1997, *Prostaglandins Leukot. Essent. Fatty Acids*, 56: 271-280
Smith D. W., ed., 1993, *Biocomputing: Informatics and Genome Project*, Academic Press, New York
Takeda et al., 1993, *Anticancer Res.*, 13: 193-199
Tilvis R. S. and Miettinen T. A., 1985, *J. Clin. Endocrinol. Metab.*, 61: 741-745
Todd et al., 1999, *Plant J.*, 17: 119-130
van Doormaal et al., 1988, *Diabetologia*, 31: 576-584
von Heijne G., 1987, *Sequence Analysis in Molecular Biology*, Academic Press, New York
Waldmann T. A., 1991, *Science*, 252: 1657-1662
Watanabe T. and Kuroda Y., 1999, *J. Med. Invest.*, 46: 173-177
Weber et al., 1994, *J. Nat. Cancer Inst.*, 86: 638-639
Wigmore et al., 1997, *Clin. Sci.*, 92; 215-221
Wright S. and Burton J. L., 1982, *Lancet*, 2:1120-1122
Zaug et al., 1984, *Science*, 224: 574-578
Zaug A. J. and Cech T. R., 1986, *Science*, 231: 470-475
Zaug et al., 1986, *Nature*, 324: 429-433

We claim:

1. A method of screening for a modulator which is capable of modulating or regulating the transcriptional expression of a human delta-5-desaturase enzyme gene, comprising the steps of:
   (a) providing a host system containing a nucleic acid consisting of a nucleic acid sequence of SEQ ID NO: 1 and a reporter gene operably associated therewith, wherein said nucleic acid is effective to initiate, terminate or regulate a level of transcription of the reporter gene;
   (b) contacting the host system with a test compound;
   (c) evaluating the level of transcription of the reporter gene, wherein a measurable difference in the level of transcription of the reporter gene in the presence of the test compound compared to a control under identical conditions but in the absence of the test compound is an indicator of an ability of the test compound to transcriptionally modulate or regulate expression of the delta-5-desaturase gene; and
   (d) selecting as said modulator the test compound which exhibits said ability.

2. A method of screening for a modulator according to claim 1, wherein the screening method is an assay for identifying modulators that modulate lipid metabolism.

3. A method of screening for a modulator according to claim 1, wherein the screening method is an assay for identifying modulators that modulate diabetic neuropathy.

4. The method of claim 2, wherein the screening method is an assay for identifying modulators that modulate the n-3 lipid metabolic pathway, conversion of 18:3n3 to 22:6n3.

5. The method of claim 2, wherein the screening method is an assay for identifying modulators that modulate the n-9 lipid metabolic pathway, conversion of 16:0 to 22:4n9.

6. The method of claim 2, wherein the screening method is an assay for identifying modulators that modulate the n-6 lipid metabolic pathway, conversion of 8:2n6 to 22:5n6.

* * * * *

UNITED STATES PATENT AND TRADEMARK OFFICE
CERTIFICATE OF CORRECTION

PATENT NO. : 7,256,028 B2
APPLICATION NO. : 10/415232
DATED : August 14, 2007
INVENTOR(S) : Winther et al.

Page 1 of 1

It is certified that error appears in the above-identified patent and that said Letters Patent is hereby corrected as shown below:

Title Page, (73) Assignee, please replace "Xenon Genetics Inc." with --Xenon Pharmaceuticals Inc.--

Signed and Sealed this

First Day of September, 2009

David J. Kappos
*Director of the United States Patent and Trademark Office*